US010871467B2

(12) United States Patent
Adelman et al.

(10) Patent No.: US 10,871,467 B2
(45) Date of Patent: Dec. 22, 2020

(54) CANNABINOID PROFILING USING NANOPORE TRANSDUCTION

(71) Applicant: Cannaptic Biosciences, LLC, Santa Cruz, CA (US)

(72) Inventors: Robert Adelman, Santa Cruz, CA (US); Stephen Winters-Hilt, Gunnison, CO (US)

(73) Assignee: CANNAPTIC BIOSCIENCES, LLC, Santa Cruz, CA (US)

( * ) Notice: Subject to any disclaimer, the term of this patent is extended or adjusted under 35 U.S.C. 154(b) by 62 days.

(21) Appl. No.: 16/219,182

(22) Filed: Dec. 13, 2018

(65) Prior Publication Data
US 2019/0376929 A1    Dec. 12, 2019

Related U.S. Application Data

(60) Provisional application No. 62/598,173, filed on Dec. 13, 2017, provisional application No. 62/598,154, filed on Dec. 13, 2017, provisional application No. 62/598,033, filed on Dec. 13, 2017, provisional application No. 62/598,161, filed on Dec. 13, 2017,
(Continued)

(51) Int. Cl.
| | | |
|---|---|---|
| *G01N 27/327* | (2006.01) | |
| *G01N 27/447* | (2006.01) | |
| *G01N 33/94* | (2006.01) | |
| *G01N 33/487* | (2006.01) | |

(52) U.S. Cl.
CPC ... *G01N 27/4473* (2013.01); *G01N 27/44791* (2013.01); *G01N 33/48721* (2013.01); *G01N 33/948* (2013.01)

(58) Field of Classification Search
None
See application file for complete search history.

(56) References Cited

U.S. PATENT DOCUMENTS

| | | |
|---|---|---|
| 2008/0097502 A1 | 4/2008 | Winters-Hilt et al. |
| 2013/0071837 A1 | 3/2013 | Winters-Hilt et al. |
| 2015/0344944 A1 | 12/2015 | Reid et al. |

OTHER PUBLICATIONS

Hiroyuki Tanaka, "Immunochemical Approach Using Monoclonal Antibody against Δ9-Tetrahydrocannabinolic Acid (THCA) to Discern Cannabis Plants and to Investigate New Drug Candidates," Current Drug Discovery Technologies, 2011, 8, 3-15 (Year: 2011).*

(Continued)

*Primary Examiner* — Alexander S Noguerola
(74) *Attorney, Agent, or Firm* — Potomac Law Group, PLLC

(57) ABSTRACT

Embodiments profile cannabinoids using a nanopore detector. Embodiments use an applied potential to electrophoretically draw a nanopore blockade reporter molecule into a nanopore channel to establish an electrophoretic molecular channel-capture for the reporter molecule. The reporter molecule includes one of an aptamer or a monoclonal antibody and has a specific binding to at least one of: a specific cannabinoid, a particular cannabinoid isoform; or a specific cannabinoid family. Embodiments receive a blockade channel current signal in response to a nanoscale membrane channel of the nanopore detector being partially blockaded by a presence of the reporter molecule non-covalently bonded to the membrane channel. Embodiments receive a blockade signal for the reporter molecule that is toggling between more than one level.

18 Claims, 25 Drawing Sheets

Specification includes a Sequence Listing.

Related U.S. Application Data provisional application No. 62/598,190, filed on Dec. 13, 2017, provisional application No. 62/598,145, filed on Dec. 13, 2017, provisional application No. 62/598,187, filed on Dec. 13, 2017, provisional application No. 62/598,168, filed on Dec. 13, 2017.

(56) References Cited

OTHER PUBLICATIONS

S. Winters-Hilt et al.; "Characterization of Fish Stock Diversity via EST-Based miRNA Trans-Regulation Profiling"; Nov. 27, 2017; Sci forschen; ISSN2471-4968; vol. 3.1.

S. Winters-Hilt; Biological system analysis using a nanopore transduction detector: from miRNA validation, to viral monitoring, to gene circuit feedback studies ; Mar. 23, 2017; Advanced Studies in Medical Sciences, vol. 5, 2017, No. 1, 13-53; HIKARI Ltd, www.m-hikari.com; http://dx.doi.org/10.12988.

S. Winters-Hilt; "Channel current cheminformatics and stochastic carrier-wave signal processing"; Jul. 15, 2018; International Journal of Computing and Optimization, vol. 4, 2017, No. 1, 155-157; HIKARI Ltd, www.m-hikari.com; http://dx.doi.org/10.12988/.

S. Winters-Hilt; "Clustering via Support Vector Machine boosting with simulated annealing"; International Journal of Computing and Optimization, vol. 4, 2017, No. 1, 53-89; HIKARI Ltd, www.m-hikari.com; http://dx.doi.org/10.12988/.

S. Winters-Hilt; "Distributed SVM Learning and Support Vector Reduction"; Jul. 18, 2017; International Journal of Computing and Optimization, vol. 4, 2017, No. 1, 91-114; HIKARI Ltd, www.m-hikari.com; http://dx.doi.org/10.12988/.

S. Winters-Hilt; "Finite State Automaton based signal acquisition with Bootstrap Learning"; Jul. 18, 2017; International Journal of Computing and Optimization, vol. 4, 2017, No. 1, 159-186; HIKARI Ltd, www.m-hikari.com; http://dx.doi.org/10.12988/.

S. Winters-Hilt; "Isomer-specific trace-level biosensing using a nanopore transduction detector"; Apr. 20, 2017; Clinical and Experimental Medical Sciences, vol. 5, 2017, No. 1, 35-66; HIKARI Ltd, www.m-hikari.com; http://dx.doi.org/10.12988.

S. Winters-Hilt; "Nanopore Transducer Engineering and Design"; 2017; SciForschen; International Journal of Molecular Biology and Medicine; Open Access.

S. Winters-Hilt; "RNA-dependent RNA polymerase encoding artifacts in eukaryotic transcriptomes"; Jan. 2017; pp. 1-27.

* cited by examiner

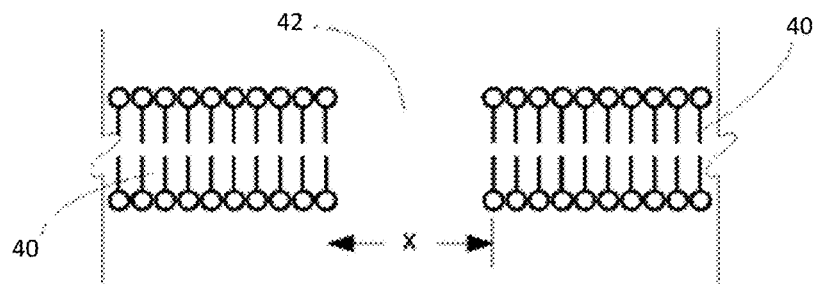
Fig. 1F
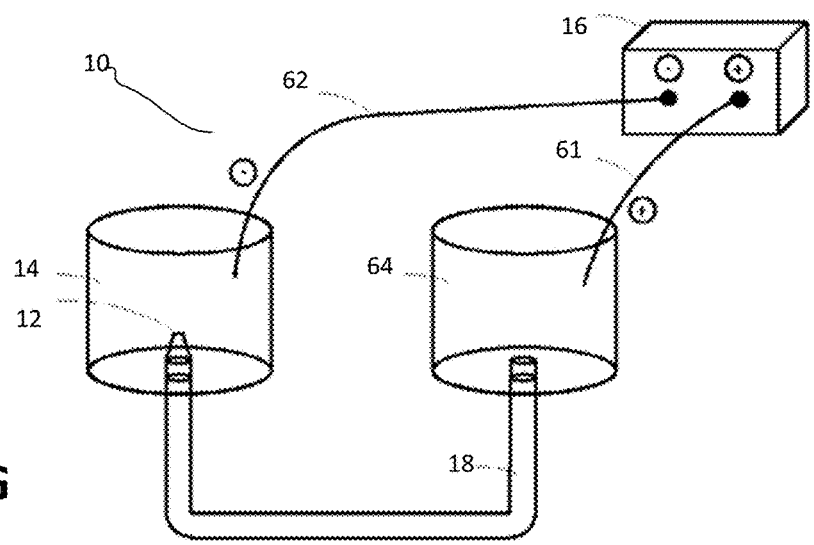
Fig. 1G
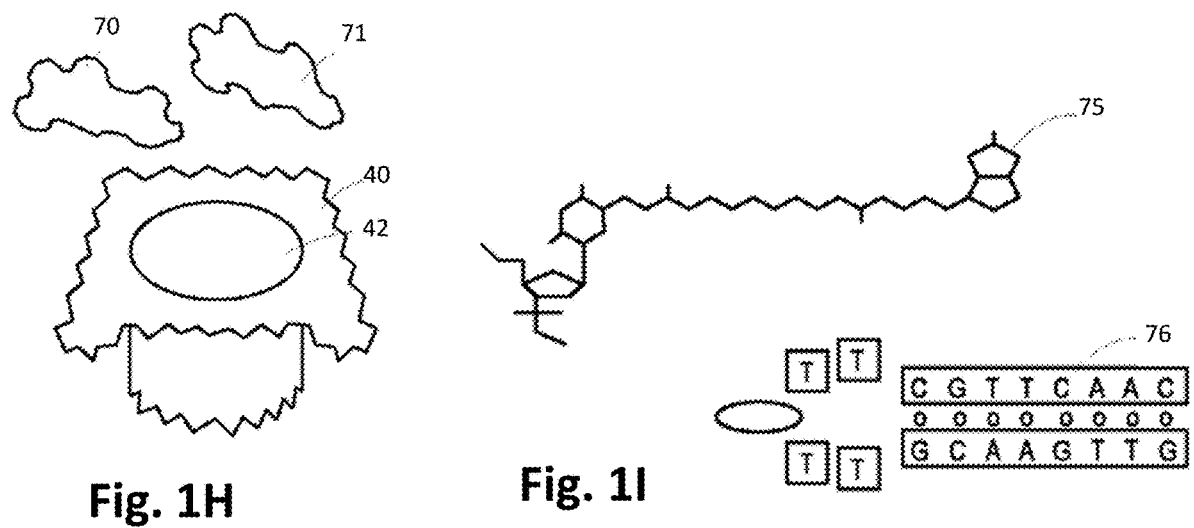
Fig. 1H
Fig. 1I

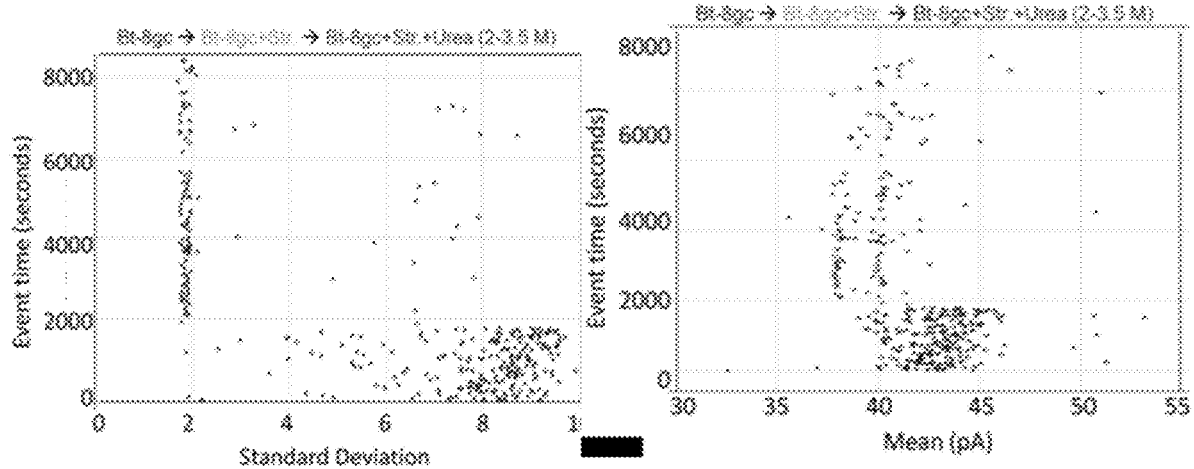
Fig. 2A  Fig. 2B
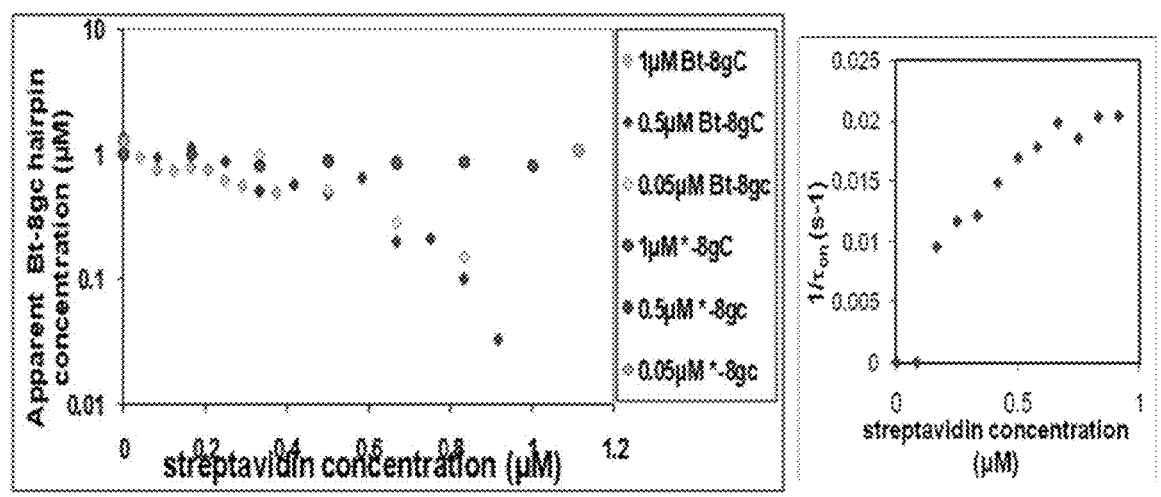
Fig. 3A  Fig. 3B

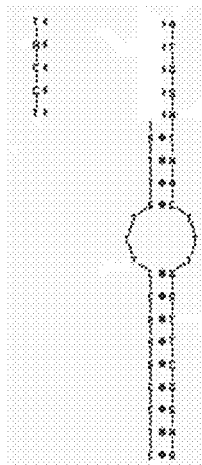 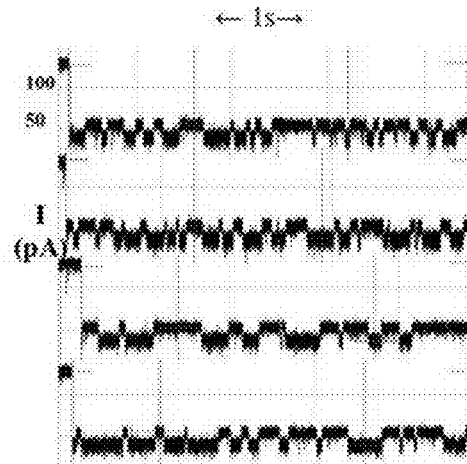 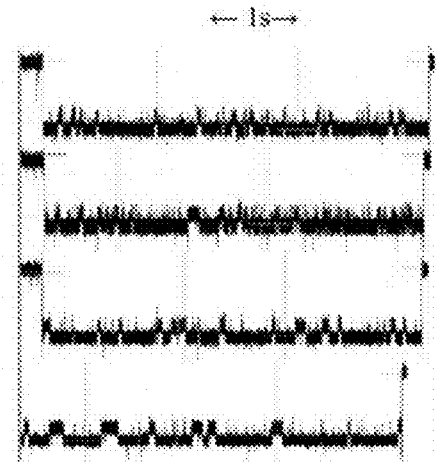
Fig. 4A      Fig. 4B      Fig. 4C
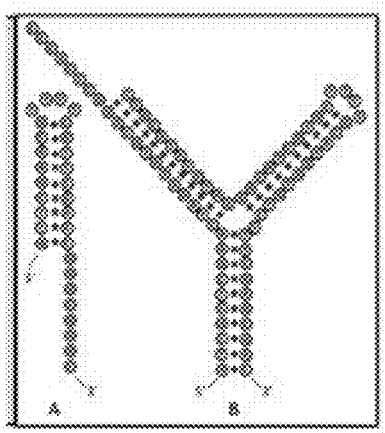 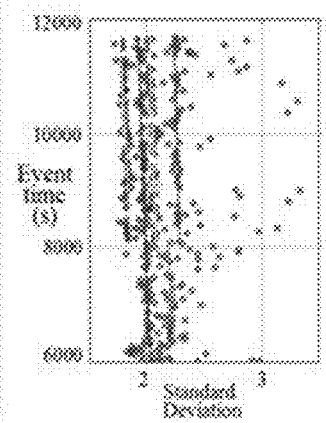 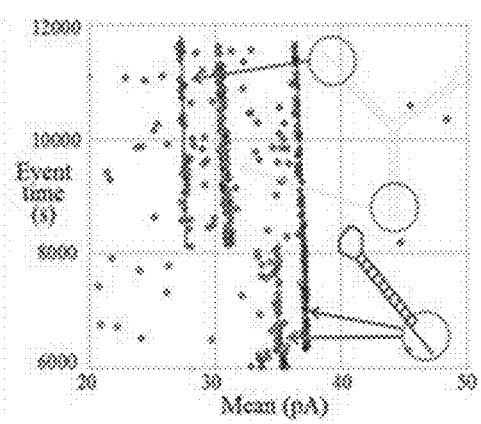
Fig. 5A      Fig. 5B      Fig. 5C
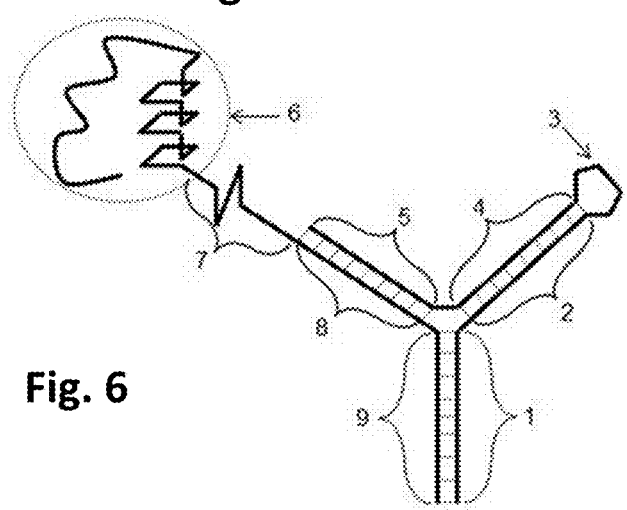
Fig. 6

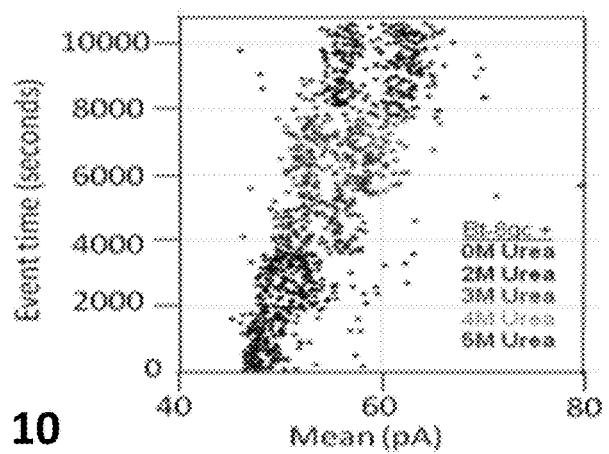
Fig. 10
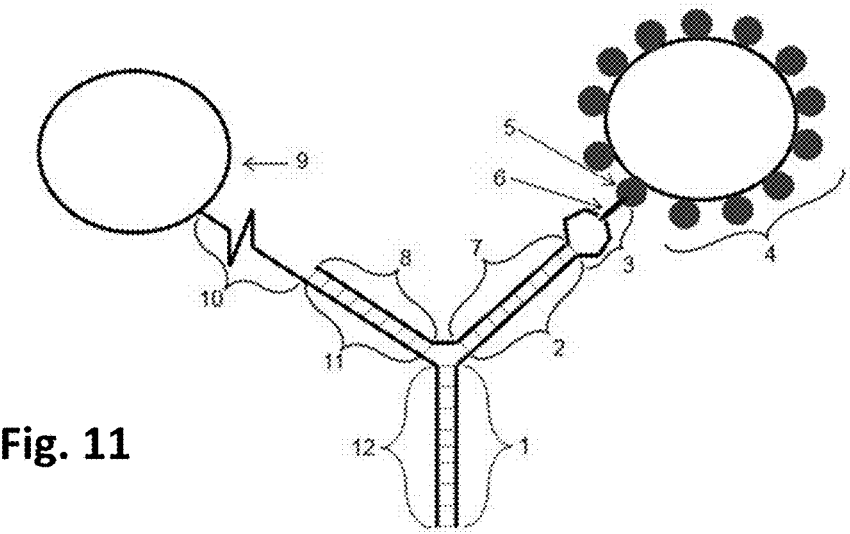
Fig. 11
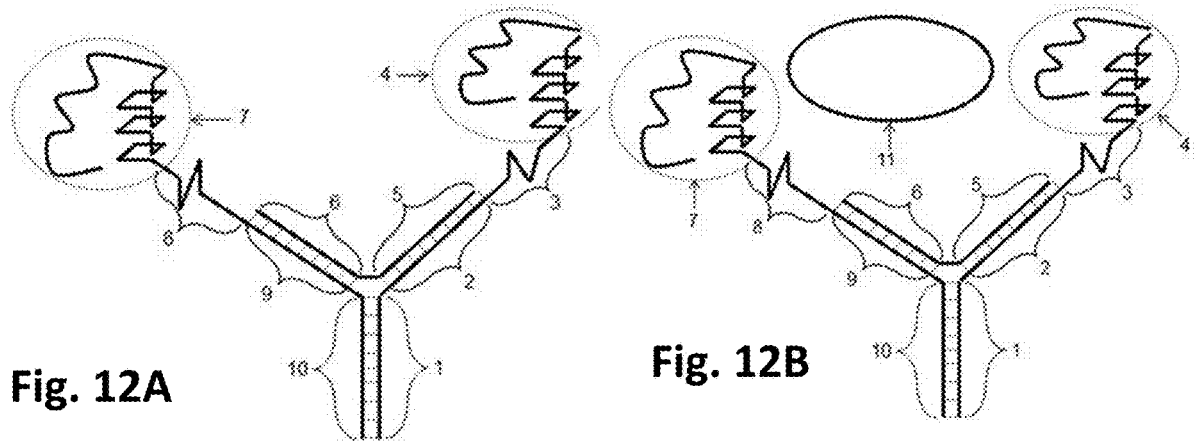
Fig. 12A
Fig. 12B

Painted Transcriptome Sequence

Fig. 64 (caption) — Painted Genome Sequence

CANNABINOID PROFILING USING NANOPORE TRANSDUCTION

CROSS REFERENCE TO RELATED APPLICATIONS

This application claims priority of the following U.S. Provisional Patent Applications, each of which was filed on Dec. 13, 2017 and the disclosure of each of which is hereby incorporated by reference: 62/598,168; 62/598,173; 62/598,161; 62/598,154, 62/598,190, 62/598,145, 62/598,187; and 62/598,033.

SEQUENCE LISTING

The instant application contains a Sequence Listing which has been filed electronically in ASCII format and is hereby incorporated by reference in its entirety. Said ASCII copy, created on Aug. 21, 2019, is named 2264-0010US01_SL.txt and is 6,432 bytes in size.

FIELD

One embodiment is directed generally to a nanopore transduction, and in particular to using nanopore transduction to profile molecules.

BACKGROUND INFORMATION

Nanopore sequencing, using nanopore transduction detection ("NTD"), in general uses electrophoresis to transport an unknown sample through an orifice. A nanopore system includes an electrolytic solution so that when a constant electric field is applied, an electric current can be observed in the system. The magnitude of the electric current density across a nanopore surface depends on the nanopore's dimensions and the composition of deoxyribonucleic acid ("DNA") or ribonucleic acid ("RNA") that is occupying the nanopore. Sequencing is made possible because, when close enough to nanopores, samples cause characteristic changes in electric current density across nanopore surfaces. The total charge flowing through a nanopore channel is equal to the surface integral of electric current density flux across the nanopore unit normal surfaces between times $t_1$ and $t_2$.

Further, a nanopore filter, or channel detection device, can be used to detect one or more molecules of interest through unique signals on a nanopore blockage current. One example of such a system has been referred to as a "Coulter Counter", and has been used to count pulses to measure the bacterial cells passing through the aperture using hydrostatic pressure.

Often the molecule of interest in a channel detection device is attached to another molecule (referred to as a "carrier molecule") through a chemical bond. The carrier molecule and the molecule to which it is attached are sensed as they pass together as a single unit through a channel or nanopore in a filter system.

Some of the detection systems use a pore or channel which is large enough to allow the molecule of interest and a carrier molecule to pass completely through the pore and measure signals as a result of that passage, with the passage through the pore being referred to as a "translocation". Such translocations often occur very quickly, at an uncontrolled rate and at a random orientation, and therefore may not provide a signal with enough information to indicate the structure of the molecules translocating.

BRIEF DESCRIPTION OF THE DRAWINGS

FIGS. 1A-1K illustrate examples and details of a nanopore transduction detection ("NTD") device. FIGS. 1C and 1I disclose SEQ ID NO: 11.

FIGS. 2A and 2B illustrate streptavidin.

FIGS. 3A and 3B illustrate the apparent Bt-8gc concentration upon exposure to streptavidin.

FIGS. 4A-C illustrate a five-base annealing using a pseudo-aptamer NTD transducer. FIG. 4A discloses SEQ ID NO: 12.

FIGS. 5A-5C illustrate an eight-base annealing using a NTD Y-transducer.

FIG. 6 illustrates a DNA Y-transducer for high-specificity aptamer binding detection and biosensing.

FIG. 10 illustrates a 8GC-Bt transducer blockade signals in the presence of high urea concentrations.

FIG. 11 illustrates a Y-laser transducer for high-specificity binding detection or individual protein binding and conformational change study.

FIGS. 12A-12B illustrate a Y-transducer for high-specificity dual-aptamer binding detection.

FIG. 64 illustrates results of high-frequency motif UC Painter on EST and noisy genomic cDNA data. FIG. 64 discloses SEQ ID NOS 13-15, respectively, in order of appearance.

DETAILED DESCRIPTION

Figures 1A, 1B, 1C:
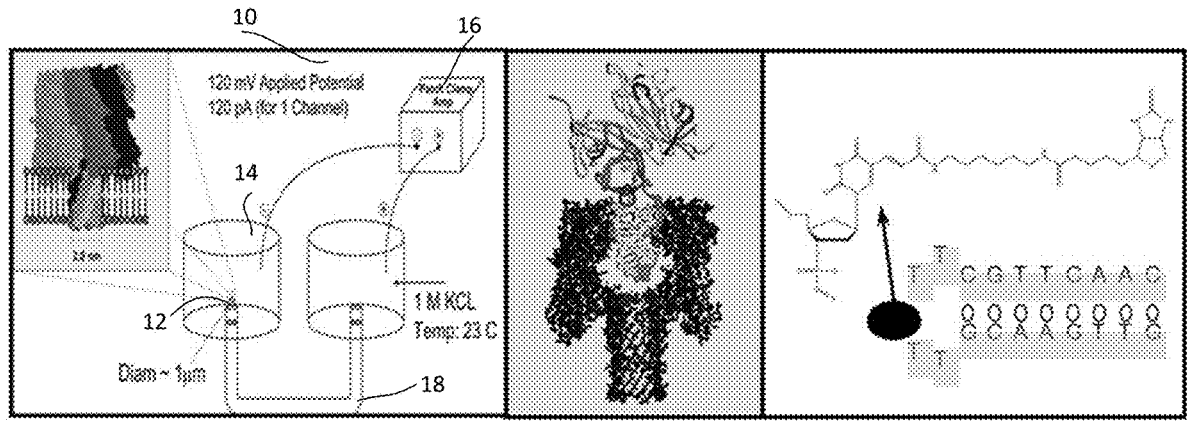

Embodiments profile cannabinoids using nanopore transduction detection ("NTD"). Over 100 different cannabinoids have been isolated from *Cannabis* and many are known to have significant therapeutic benefits. However, different *Cannabis* plants can have very different cannabinoid profiles.

A variety of monoclonal antibodies and aptamers have been developed with binding to tetrahydrocannabinol ("THC"), the psycho-active cannabinoid, with varying degrees of specificity to differentiate from the other cannabinoids. Little has been developed, however, to assay the specific presence and amounts of the other hundred or so cannabinoids.

In contrast, embodiments allow for a relatively inexpensive assaying of *Cannabis* profiles that provides not only the ability to specifically bind a particular cannabinoid with high affinity, but also generates a multiplex profile a mixture of cannabinoids with high accuracy. Embodiments use NTD where the aptamer or monoclonal antibody selected for the specific cannabinoid binding of interest is linked to a NTD transducer for direct quantification on the relative abundances of the different cannabinoids.

Nanopore transduction of events has been implemented with a single-modulated-channel thin film, or membrane, device. The modulated-single-channel thin film is placed across a horizontal aperture, providing a seal such that a cis and trans chamber are separated by the modulated single-channel connection. In some embodiments an applied potential is used to establish current through the single, modulated ion-current, channel. In other embodiments periodic laser modulations are used to induce channel-state dependent stochastic modulations in the channel current. In other embodiments multiple channels resident in the membrane are made possible, where only one or a few channels are modulated with a modulating channel blockade, and where any other channels present only offer a steady, unmodulated, noisy, current source that is easily filtered out by the use of the effective stochastic carrier wave heterodyning capabilities from hidden Markov model with binned duration model ("HMMBD") and meta-hidden Markov model ("HMM") methods.

In general, with embodiments, the NTD devices can be made "smarter" according to use of their "noise" information. Consider, for example, a device that has two states, A and B, and associated noise profiles N(A) and N(B). A "noise profile" for a device state includes observations of device operational parameters while in that state. Using this information it is possible to track device operational state according to learning and classification of the device noise state. Part of the engineering task when enabling such a system is to establish a device with observational parameters that reveal system noise in a useful manner, such that noise "tracks on state". This noise is provided in NTD devices where a large variety of biomolecules are found to blockade the channel in a modulatory manner highly sensitive to their molecular state. In other complex systems, such as a car, this is possible too, such as what a good mechanic can do by simply listening to the car (noise) under different test conditions.

However, the system noise may not be significantly strong or distinctively tracking on states of interest. In this instance, injection of modulatory signal (periodic or stochastic) can be used to induce distinctive system noise as desired.

Assume it is desired to observe and classify (track) the state of a complex system. Assume there is a means to couple a signal generator to that complex system such that signal generation, or signal noise, is different according to complex system state. Then, state tracking is accomplished by pattern recognition and classification of the different signal types seen.

The communication aspect of the signal processing can be taken to a further extreme, where noise states A and B are 0 and 1 bit encodings, for example, and the streaming A and B noise states correspond to a $\{0,1\}$ bit stream. Decoding is an identification of the A and B noise phases in the signal. This type of communication has steganographic utility in that if it is not known which noise textures to look for (and differentiate) then seeing the signal can be very difficult. This is because significant white noise can be added to the $\{A,B\}$ stream of noise phases and the $\{A,B\}$ noise phases still resolved. This is similar to the time-integration signal boosting inherent in AM-radio heterodyning to extract signal from (periodic) carrier wave, except that here the heterodyning is not accomplished by a mixing signal with the known carrier frequency and using some simple (time) integral calculus, instead of an HMMBD or meta-HMM is used to extract the signal using the known stochastic carrier's stationary signal (statistical) parameters.

A simple signal with a standard periodic carrier is easily spotted via power spectral density analysis. A known signal reveals that there is communication, the timing and volume of that communication, and, over time, the physical origination site of that communication. Jamming a known signal can be focused on the known carrier of that signal. Jamming an unknown signal, however, requires just blasting with white noise and other brute force methods. For the stochastic carrier wave encodings, or "whisper channel" messaging, the carrier is not known, thus its presence can't be ascertained, and the communication can't be directly jammed, and yet it still has the heterodyning benefits of the standard carrier-based methods. Thus, even if extra white noise is added, the communication channel can be designed with sufficient integration time (sufficient durations of noise texture phases) such that the whisper channel remains open.

Nanopore Transduction Detection Platform

An NTD device/platform in accordance with embodiments includes a single nanometer scale channel that allows a single ionic current flow across a membrane and an engineered, or selected, channel blockading molecule. The channel blockading molecule is engineered or selected such that it provides a current modulating blockade in the detector channel when drawn into the channel, and held, by electrophoretic means. The channel is chosen such that it has inner diameter at the scale of that molecule or one of its molecular-complexes. For most biomolecular analysis implementations this leads to a choice of channel that has inner diameter in the range of 0.1-10 nm to encompass small and large biomolecules and molecular complexes, where the inner diameter of 1.5 nm is utilized in the alpha-hemolysin protein based channel disclosed below. The channel is generally referred to as a "nanopore" based on its size. Other known devices, sometimes also referred to as nanopores, include 100-1000 nm range channels, and hereafter are appropriately referred to as "micropores."

In order to have a capture state in the channel with a single molecule, a true nanopore is needed, not a micropore, and to establish a coherent capture-signal exhibiting non-trivial stationary signal statistics, which is the modulating-blockade desired, the nanopore's limiting inner diameter typically needs to be sized at approximately 1.5 nm for duplex DNA channel modulators (i.e., what is found for the alpha-hemolysin channel). The modulating-blockader is captured at the channel for the time-interval of interest by electrophoretic means, which is established by the applied potential that also establishes the observed current flow through the nanopore.

FIG. 1A illustrates an NTD device 10. NTD 10 includes a single pore 12 in a lipid bilayer which is created by the oligomerization of the staphylococcal alpha-hemolysin toxin in a left chamber 14, and a patch clamp amplifier 16 capable of measuring pico Ampere channel currents, and a U-tube 18. FIG. 1B illustrates a biotinylated DNA hairpin molecule captured in the channel's cis-vestibule, with streptavidin bound to the biotin linkage that is attached to the loop of a DNA hairpin in accordance with one embodiment. FIG. 1C illustrates the biotinylated DNA hairpin molecule (Bt-8gc).

Figure 1D:
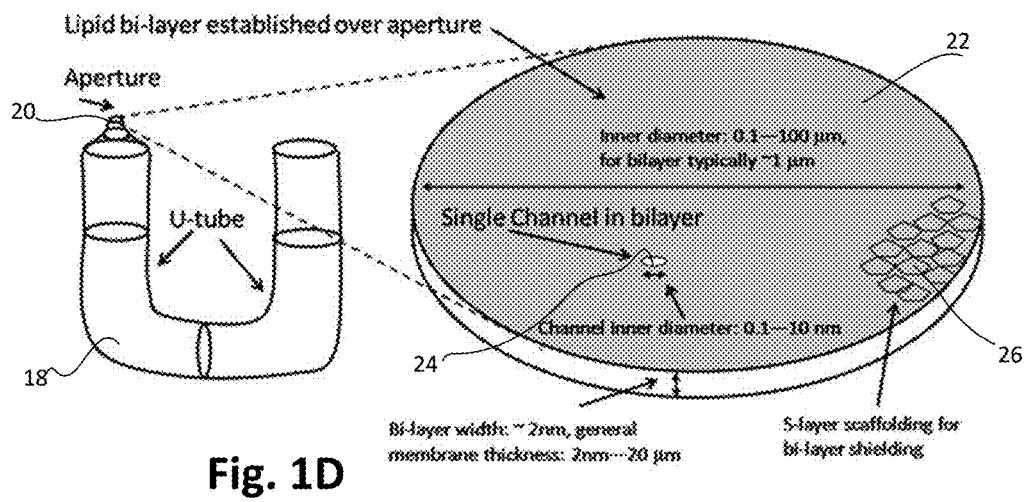

FIG. 1D illustrates additional details of the U-tube 18 of FIG. 1A. U-tube 18 includes aperture 20, a bilayer 22, and a single channel 24, with possible S-layer modifications 26 to bi-layer 22.

Figure 1E:
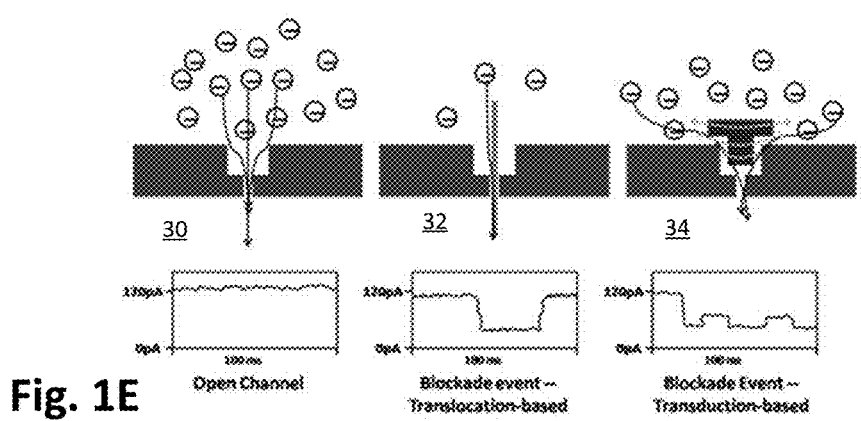

FIG. 1E illustrates translocation information and transduction information. At 30, an open channel 30 and a representative resultant electrical signal is shown below. At 32, a channel blockade event is shown with feature extraction that is typically dwell-time based and its representative resultant electrical signal is shown below. This may represent a single-molecule coulter counter. At 34, a single-molecule transduction detection is shown with a transduction molecule modulating current flow. The current flow typically switches between a few dominant levels of blockade. The dwell time of the overall blockade is not typically a feature—many blockade durations will not translocate in the time-scale of the experiment, for example, active ejection control is often involved, where "active ejection control" is a systematic release of the molecule after a certain specified time or upon recognizing a certain condition.

FIG. 1F illustrates a lipid bilayer side-view 40 with a simple "cut-out" channel 42. FIG. 1G is another illustration of NTD device 10. Patch-clamp amplifier 16 is connected to a positive electrode 61 and a negative electrode 62, with negative electrode 62 in the cis-chamber 14 of electrolyte solution and with positive electrode 61 in the trans-chamber 64 of electrolyte solution. The two electrolyte chambers have a conductance path via U-tube 18 and via the aperture restriction feeding into the cis-chamber, where the bilayer 12 is established.

FIG. 1H is another view of NTD device 10. The cis-side of the channel 42 is shown embedded in a bilayer 40, with possible channel interactants or modulators shown at 70 and 71. FIG. 1I illustrates a biotinylated 75 and DNA hairpin 76.

Figure 1J:
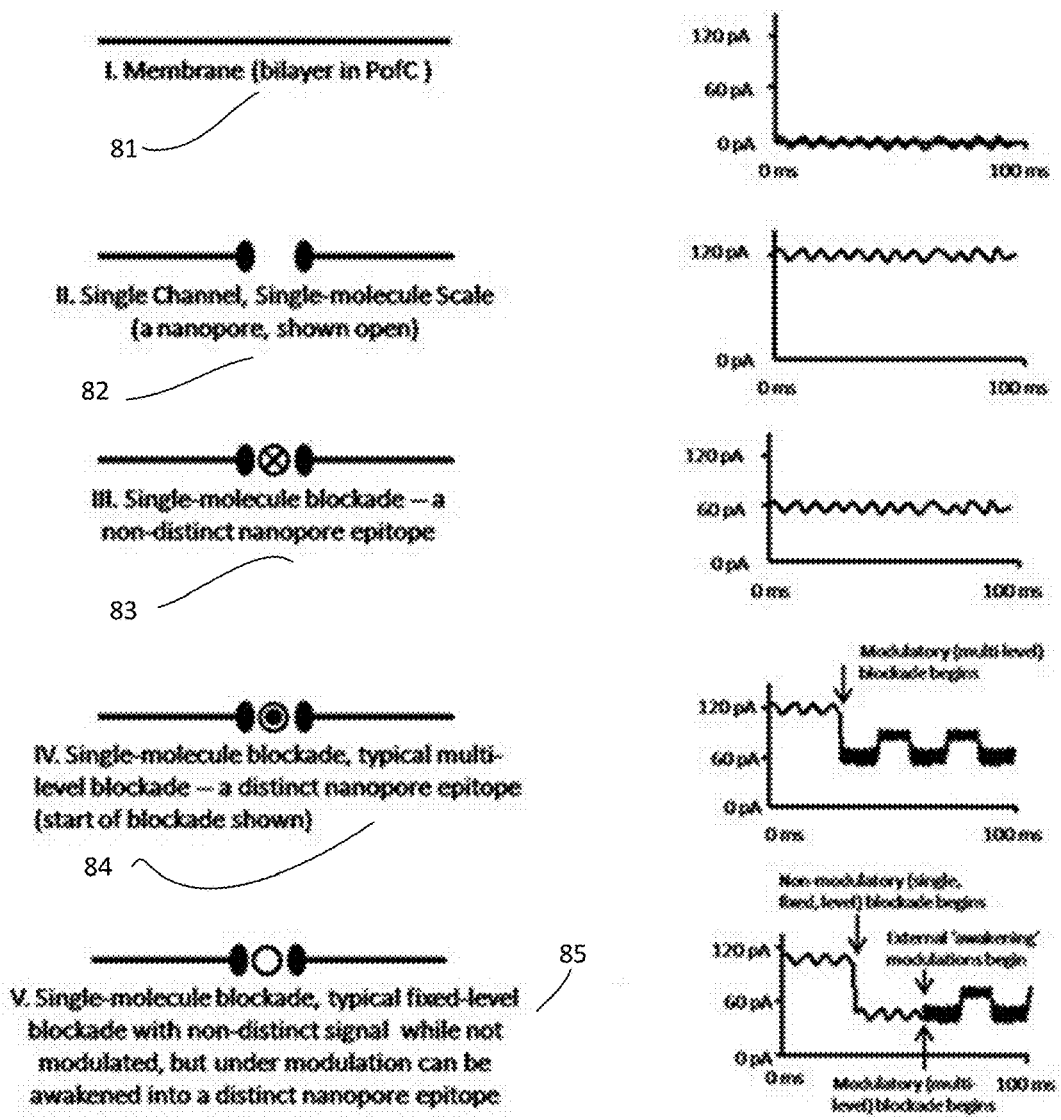

FIG. 1J illustrates examples of various modes of channel blockade, along with a representative electrical signals. Example 81 illustrates no channel—e.g., a Membrane (bilayer). Example 82 illustrates a single channel, single-molecule scale (a nanopore, shown open). Example 83 illustrates a single-molecule blockade, a brief interaction or blockade with fixed-level with non-distinct signal—a non-modulatory nanopore epitope. IV. Example 84 illustrates a single-molecule blockade, typical multi-level blockade with distinct signal modulations (typically obeying stationary statistics or shifts between phases of such). Example 85 illustrates a single-molecule blockade, typical fixed-level blockade with non-distinct signal while not modulated, but under modulation can be awakened into distinct signal, with distinct modulations.

Figure 1K:
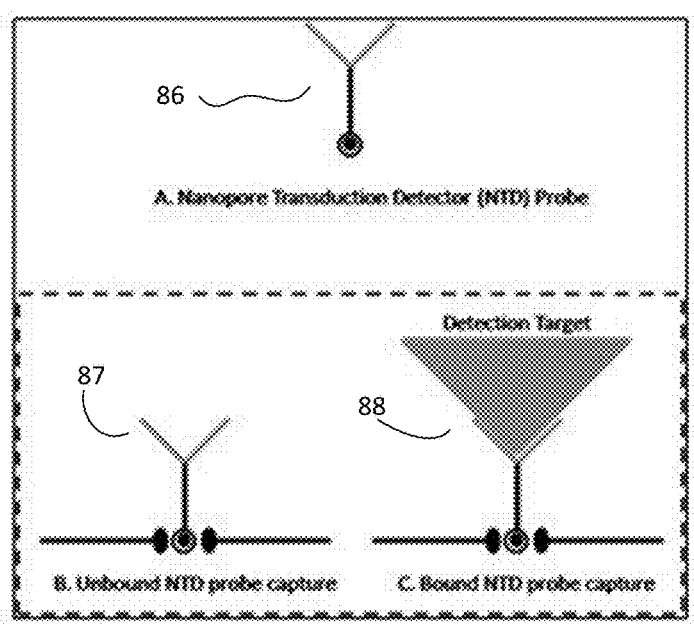

FIG. 1K illustrates an example NTD probe in accordance to embodiments. A bifunctional molecule 86, includes one end channel-modulatory upon channel-capture (and typically long-lived), the other end multi-state according to the event detection of interest, such as the binding moieties (antibody and aptamer, schematically indicated in bound and unbound configurations in 87 and 88), to enable a biosensing and assaying capability.

FIGS. 2A and 2B illustrate streptavidin. As shown in FIG. 2A, observations of individual blockade events are shown in terms of their blockade standard deviation (x-axis) and labeled by their observation time (y-axis). The standard deviation provides a good discriminatory parameter in this instance since the transducer molecules are engineered to have a notably higher standard deviation than typical noise or contaminant signals. At T=0 seconds, 1.0 µM Bt-8gc is introduced and event tracking is shown on the horizontal axis via the individual blockade standard deviation values about their means At T=2000 seconds, 1.0 µM Streptavidin is introduced. Immediately thereafter, there is a shift in blockade signal classes observed to a quiescent blockade signal, as can be visually discerned. The new signal class is due to (Streptavidin)-(Bt-8gc) bound-complex captures.

As shown in FIG. 2B, a marked change in the Bt-8gc blockade observations is shown immediately upon introducing streptavidin at T=2000 seconds, but with the mean feature two distinctive and equally frequented (racemic) event categories can be clearly seen. The introduction of chaotropic agents degrades first one, then both, of the event categories, as 2.0 M urea is introduced at T=4000 seconds and steadily increased to 3.5 M urea at T=8100 seconds.

FIGS. 3A and 3B illustrate the apparent Bt-8gc concentration upon exposure to streptavidin. As shown in FIG. 3A, the vertical axis describes the counts on unbound Bt-8gc blockade events and the above-defined mapping to "apparent" concentration is used. In the dilution cases, a direct rescaling on the counts is done, to bring their "apparent" concentration to 1.0 µM concentration (i.e., the 0.5 µM concentration counts were multiplied by 2). For embodiments with no biotin (denoted '*-8gc'), the *-8gc concentration shows no responsiveness to the streptavidin concentration.

FIG. 3B shows the increasing frequency of the blockades of a type associated with the streptavidin-Bt-8gc bound complex. The background Bt-8gc concentration is 0.5 µM, and the lowest clearly discernible detection concentration is at 0.17 µM streptavidin.

The NTD molecule providing the modulating blockade has a second functionality, typically to specifically bind to some target of interest such that its blockade modulation is discernibly different according to binding state, such as with the DNA annealing examples shown in FIG. 4 and FIG. 5, described below. Thus, the NTD modulators are engineered to be bifunctional in that one end is meant to be captured, and modulate the channel current, while the other, extra-channel-exposed end, is engineered to have different states according to the event detection, or event-reporting, of interest. Examples include extra-channel ends linked to binding moieties such as antibodies, antibody fragments, or aptamers. Examples also include "reporter transducer" molecules with cleaved/uncleaved extra-channel-exposed ends, with cleavage by, for example, UV or enzymatic means. Embodiments then use signal processing to process the channel current blockade modulations, and thereby track the molecular states engineered into the transducer molecules, to function as a biosensor or assayer. By tracking transduced states of a coupled molecule undergoing conformational changes, such as an antibody, or a protein with a folding-pathway associated with disease, direct examination of co-factor, and other, influences on conformation can also be assayed at the single-molecule level.

Fundamentally, the weaknesses of the known standard ensemble-based binding analysis methods are directly addressed with this single-molecule approach. The role of conformational change during binding, in particular, could potentially be directly explored in this setting. Embodiments also offer advantages over other translation-based nanopore detection approaches in that the transduction-based apparatus introduces two strong mechanisms for boosting sensitivity on single-molecule observation: (i) engineered sensitivity in the transduction molecule itself; and (ii) machine learning based signal stabilization and highly sensitive state resolution. NTD used in conjunction with novel pattern recognition informed sampling capabilities greatly extends the usage of the single-channel apparatus (including learning the avoidance of blockades associated with channel failure, when contaminants necessitate; and nanomanipulation, where we have a single-molecule under active control in a nanofluidics-controlled environment). For medicine and biology, NTD methods in accordance with embodiments can aid in understanding multi-component interactions (with co-factors or adjuvants), and aid in designing co-factors according to their ability to result in desired binding or modified state.

NTD works at a scale where physics, chemistry, and biomedicine methodologies intersect. In some applications the NTD platform functions like a biosensor, or an artificial nose, at the single-molecule scale, e.g., a transducer molecule rattles around in a single protein channel, making transient bonds to its surroundings, and the binding kinetics of those transient bonds is directly imprinted on a surrounding, electrophoretically driven, flow of ions. The observed channel current blockade patterns are engineered or selected to have distinctive stationary statistics, and changes in the channel blockade stationary statistics are found to occur for a transducer molecule's interaction moiety upon introduction of its interaction target. In other applications the NTD functions like a "nanoscope", e.g., a device that can observe the states of a single molecule or molecular complex. With embodiments of the NTD apparatus the observation is not in the optical realm, such as with the microscope, but in the molecular-state classification realm. NTD, thus, provides an unprecedented new technology for characterization of transient complexes. Embodiments include machine learning methods for pattern recognition that can be implemented on a distributed network of computers for real-time experimental feedback and sampling control.

NTD Transducer/Reporter Molecules and the Use of Laser Excitation

It is known that with a nanopore transduction detector the presence of a specific five base length nucleic acid can be ascertained, and that an eight base sequence of DNA can be ascertained with very high specificity with the introduction of urea as a chaotrope. In known methods, the DNA annealing based detection was performed with a Y-shaped DNA transduction molecule engineered to have an eight-base overhang where a DNA hairpin with complementary 8 base overhang was used as the binding partner.

FIGS. 4A-C illustrate a five-base annealing using a pseudo-aptamer NTD transducer. FIG. 4A illustrates aptamer experiments based on a DNA molecule obtained from annealing ssDNA1: 5'-CAAGCTTGGTTTCGA-TAGGTA-3' (SEQ ID NO: 1) with ssDNA2: 5'-ATCGTTTCCAAGCTTG-3' (SEQ ID NO: 2). For the pseudo-aptamer binding experiment a solution of annealed ssDNA1 and SSDNA2 molecules was exposed to ssDNA3: 5'-TACCT-3' (which anneals to the remaining AGGTA complement on ssDNA1). The target 5-base ssDNA is introduced subsequent to obtaining a toggler-type capture of the aptamer molecule (properly annealed). The transducer is referred to as a pseudo-aptamer experiment due to its simplification to a DNA annealing based detection. FIG. 4B illustrates a collection of toggle signals from the captured pseudo-aptamer. FIG. 4C illustrates a collection of toggle signals from the pseudo-aptamer solution upon exposure to the ssDNA3 five-base target sequence. A distinctive blockade feature only observed in the blockade signals after ssDNA3 is introduced, aside from the level dwell-time changes, are the much higher frequency of upward "spike" transitions, from the lower level to the upper level.

FIGS. 5A-5C illustrate an eight-base annealing using a NTD Y-transducer. In FIGS. 5A-C, the binding results at the population-level where numerous single-molecule events are sampled and identified in FIG. 5A shows the DNA hairpin and DNA Y-nexus transducer secondary structures with sequence information. In FIGS. 5B and 5C, the Y-shaped DNA transducer with overhang binding to DNA hairpin with complementary overhang is shown. Only a portion of a repetitive validation experiment is shown, thus time indexing starts at the 6000th second. From time 6000 to 6300 seconds (the first 5 minutes of data shown) only the DNA hairpin is introduced into the analyte chamber, where each point in the plots corresponds to an individual molecular blockade measurement. At time 6300 a second urea is introduced into the analyte chamber at a concentration of 2.0 M. The DNA hairpin with overhang is found to have two capture states (clearly identified at 2 M urea). The two hairpin channel-capture states are marked with the green and red lines, in both the plot of signal means and signal standard deviations. After 30 minutes of sampling on the hairpin+urea mixture (from 6300 to 8100 seconds), the Y-shaped DNA molecule is introduced at time 8100. Observations are shown for an hour (8100 to 11700 seconds). A number of changes and new signals now are observed: (i) the DNA hairpin signal class identified with the green line is no longer observed—this class is hypothesized to be no longer free, but annealed to its Y-shaped DNA partner; (ii) the Y-shaped DNA molecule is found to have a bifurcation in its class identified with the yellow lines, a bifurcation clearly discernible in the plots of the signal standard deviations; (iii) the hairpin class with the red line appears to be unable to bind to its Y-shaped DNA partner, an inhibition currently thought to be due to G-quadruplex formation in its G-rich overhang; (iv) The Y-shaped DNA molecule also exhibits a signal class (blue line) associated with capture of the arm of the 'Y' that is meant for annealing, rather than the base of the 'Y' that is designed for channel capture.

In known examples, work 8 and 9 base-pair DNA hairpins were used as channel modulators, where the modulator had a covalently attached binding moiety (biotin or linked antibody) that was tracked as to its binding state according to the channel modulation exhibited by their channel-captured DNA hairpin ends. For example, FIGS. 1-3 illustrate a known biotin-streptavidin binding example. Further developments along these lines without as complicated a linker arrangement, where a more commoditized immuno-PCR tagging methodology is used, led to the known DNA "Y-transducer" platform, details of which are illustrated in FIGS. 6-8 below.

FIG. 6 illustrates a DNA Y-transducer for high-specificity aptamer binding detection and biosensing. In FIG. 6 the Y-transducer is meant to have a high-specificity aptamer attached by a single stranded, possibly abasic (non-base-pairing), nucleic acid linker, region 7, to an aptamer in region 6. The sketch of the aptamer in region 6 is meant to suggest the 3D conformational aspect of the aptamer, where stacking of G-quadruplexes is a common, but not necessary, feature of aptamers. The Y-transducer is comprised of two, possibly RNA/DNA chimeric, nucleic acids, where the first single stranded nucleic acid is indicated by regions 1-5 and the second nucleic acid is indicated by regions 6-9. The paired regions {1, 9}, {2, 4}, and {5, 8} are meant to be complements of one another (with standard Watson-Crick base-pairing), and designed such that the annealed Y-transducer molecule is meant to be dominated by one folding conformation (as shown). Region 3 is a loop, typically 4 dT in size, that is designed to be too large for entry and capture in the alpha-hemolysin channel, such that the annealed Y-transducer only has one orientation of capture in the nanopore detector. The base region, comprising regions {1, 9}, is designed to form a duplex nucleic acid that produces a toggling blockade when captured in a nanopore detector. The typical length of the base-paired regions is usually 8-10 base-pairs.

Figure 7A:
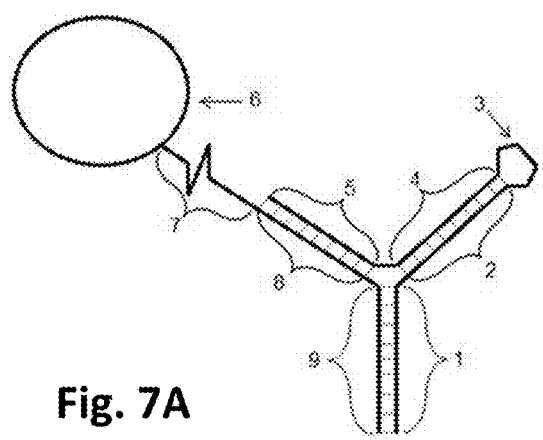
FIGS. 7A-7B illustrate a DNA Y-transducer for high-specificity monoclonal antibody, mAb, biosensing.
Figure 7B:
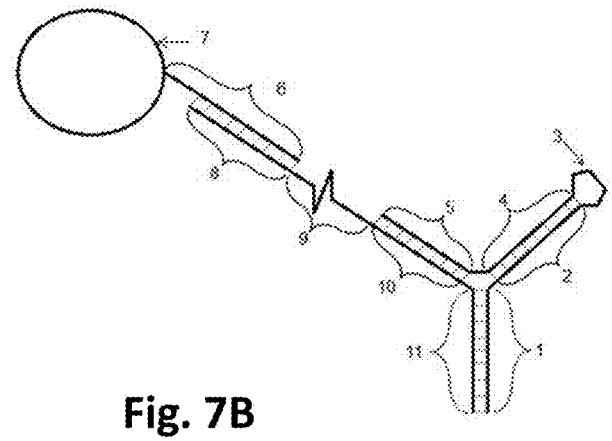

FIGS. 7A-7B illustrate a DNA Y-transducer for high-specificity monoclonal antibody, mAb, biosensing. In FIG. 7A the Y-transducer is meant to have an antibody, region 6, attached by a single stranded nucleic acid linker, region 7, that is possibly abasic (non-base-pairing), that is linked to a single stranded nucleic acid region, region 6, that is meant to anneal to a second nucleic acid to create the Y-shaped nucleic acid construct shown. The annealed Y-transducer is comprised of two, possibly RNA/DNA chimeric, nucleic acids, where the first single stranded nucleic acid is indicated by regions 1-5 and the second nucleic acid is indicated by regions 7-9. The paired regions {1,9}, {2,4}, and {5,8} are meant to be complements of one another (with standard Watson-Crick base-pairing), and designed such that the annealed Y-transducer molecule is meant to be dominated by one folding conformation (as shown). Region 3 is a loop, typically 4 dT in size, that is designed to be too large for entry and capture in the alpha-hemolysin channel, such that the annealed Y-transducer only has one orientation of capture in the nanopore detector. The base region, comprising regions {1,9}, is designed to form a duplex nucleic acid that produces a toggling blockade when captured in a nanopore detector. The typical length of the base-paired regions is usually 8-10 base-pairs. The antibody linkage to single stranded nucleic acid is a commoditized process due to the immuno-PCR industry so is an inexpensive well-established manufacturing approach for the molecular construction. The Y-transducer of FIG. 7A will not form if the "immuno-PCR tagged" antibody is not present, which provides an additional level of event detection validation. The Y-transducer of FIG. 7B is designed to form with or without the immune-PCR tagged antibody present and involved three parts: two single-stranded nucleic acid parts, comprising regions 1-5 and 8-11, and an immune-PCR antibody part, with the nucleic acid portion shown as region 6, and the linked antibody shown as region 7. As with FIG. 7A, the molecule of FIG. 7B is designed to have paired regions {1,11}, {2,4}, {5,10}, and {6,8} that are complements of one another, and designed such that the annealed Y-transducer molecule is meant to be dominated by one folding conformation (as shown). Region 3 is a loop as before, typically 4 dT in size, that is designed to be too large for entry and capture in the alpha-hemolysin channel. The base region, comprising regions {1,11}, is designed to form a duplex nucleic acid that produces a toggling blockade when captured in a nanopore detector.

Figure 8A:
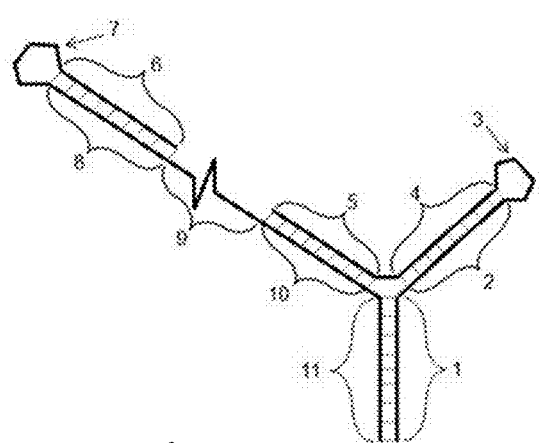
FIGS. 8A-8B illustrate Y-transducers for testing hypothesized microRNA ("miRNA") binding sites and/or miRNA interactions with a known miRNA binding site.
Figure 8B:
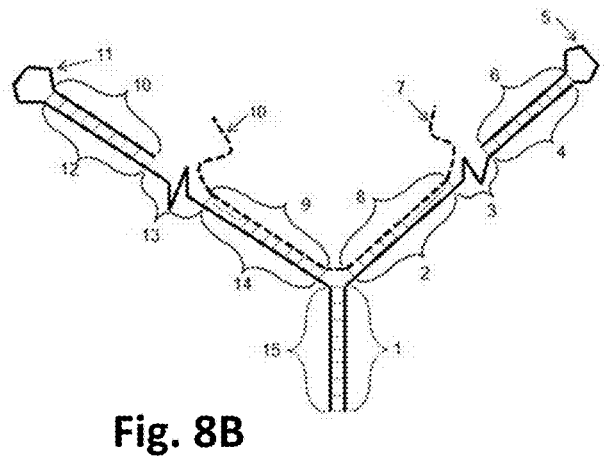

FIGS. 8A-8B illustrate Y-transducers for testing hypothesized microRNA ("miRNA") binding sites and/or miRNA interactions with a known miRNA binding site. In FIG. 8A, the Y-transducer is meant to have a ssRNA miRNA binding site encoded in region 9. This could be the RNA complement to a 7-8 base miRNA seed region, or a RNA complement to a full 21-25 base miRNA, with abasic (non-base-pairing) bases padding the target sequence on either side as needed to avoid steric interference with regions 6/8 and 5/10 (especially if the miRNA is complexed with argonaute proteins). The Y-transducer is comprised of two, possibly RNA/DNA chimeric, nucleic acids, where the first single stranded nucleic acid is indicated by regions 1-5 and the second nucleic acid is indicated by regions 6-11. The paired regions {1,11}, {2,4}, {5,10}, and {6,8} are meant to be complements of one another (with standard Watson-Crick base-pairing), and designed such that the annealed Y-transducer molecule (without miRNA binding) is meant to be dominated by one folding conformation (as shown). The regions 3 and 7 are loops, typically 4 dT in size, that are designed to be too large for entry and capture in the alpha-hemolysin channel, such that the annealed Y-transducer only has one orientation of capture in the nanopore detector. The base region, comprising regions {1,11}, is designed to form a duplex nucleic acid that produces a toggling blockade when captured in a nanopore detector. The typical length of the base-paired regions in {1,11}, {2,4}, {5,10}, and {6,8} is usually 8-10 base-pairs. In FIG. 8B, the Y-transducer has its ssRNA miRNA binding region at the Y-nexus, comprising regions 2 and 14, where the miRNA sequence being probed, shown annealed as nucleic acid regions 7-10, crosses and completes the Y-nexus, completing the Y-transducer construct only when the target miRNA is present, and where any minor variation or mismatch is strongly discernible as in prior SNP analysis (where the SNP being probed was also designed to occur at the nexus region). As with FIG. 8A, the paired regions {1,15}, {4,6}, and {10,12} are meant to be complements of one another, with one dominant fold given the miRNA target sequence in regions 2 and 14, and the loop regions (5 and 11) are meant to ensure only one possible capture orientation, via the base region {1,15}.

A Y-transducer was used in known experiments showing DNA-DNA annealing on 5-9 base nucleic acids, and in transducing DNA-protein (HIV integrase, TBP) binding events. A limitation in all of these efforts was that the critical length of duplex nucleic acid needed for modulation, even in an unbound state, ranged from 8 to 10 base-pairs for the alpha-hemolysin nanopore platform that was being used. The short duplex lengths meant that the reporter molecule could only be observed for seconds or minutes before melting, forcing the NTD to operate in a rapid-sampling "ensemble" detection mode on the transducer/reporter molecules, and less in the single-molecule event-tracking mode that might otherwise be optimal for some applications, like those disclosed herein.

Figures 9A, 9B, 9C:
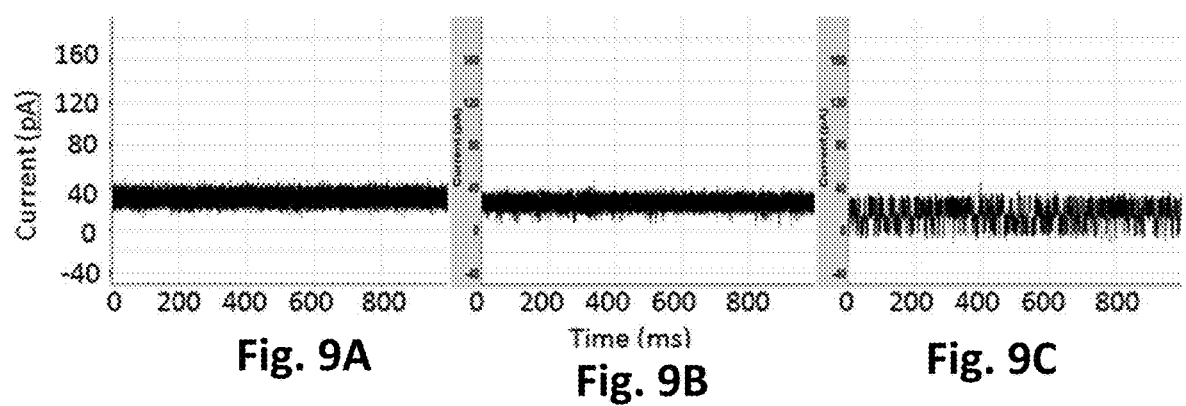
FIGS. 9A-9C illustrate a 9GC-ext-mag transducer.

Often the bound state of the transducer/reporter molecule in known solutions was found to not transduce to a different toggling ionic current flow blockade, but to a fixed-level blockade (i.e., the transducer provides distinctive channel modulation when unbound, but not so distinctive fixed-level channel blockades when bound). It is highly desirable for both the bound and unbound transducers to provide distinctive channel modulations in order to have automated high-precision state identification and tracking (and allow for multiplex assaying). The switch to a fixed-level blockade was thought to be an effect of the large bound complex forcing the channel-captured end to reside in one blockade state. This was explored in known solutions where a streptavidin-coated magnetic bead was attached to biotinylated DNA hairpins that were known to be good modulators (if 8-10 base-pairs in length) or poor channel modulators (if greater than 12 bps in length). Once a streptavidin coated magnetic bead was attached to the biotinylated hairpins, it was found that gently pulsing the nanopore channel environment with a chopped laser beam (a laser-tweezer tugging) allowed a distinctive channel modulation to result such as shown in FIG. 9. FIGS. 9A-9C illustrate a 9GC-ext-mag transducer. FIG. 9A illustrates a channel current blockade signal where the blockade is produced by 9GC DNA hairpin with 20 bp stem. FIG. 9B illustrates a channel current blockade signal where the blockade is produced by 9GC 20 bp stem with magnetic bead attached. FIG. 9C illustrates a channel current blockade signal where the blockade is produced by c9GC 20 bp stem with magnetic bead attached and driven by a laser beam chopped at 4 Hz. Each of 9A-9C shows the level of current in picoamps over time in milliseconds.

FIG. 10 illustrates a 8GC-Bt transducer blockade signals in the presence of high urea concentrations. In FIG. 10 sufficiently strong Urea concentration (5M) results in racemization of the two loop capture-variants, while weaker urea (<2M) does not. The results show Bt-8gc measurements at 30 minute intervals (1800 s on vertical axis) with urea concentration 0, 2, and 3M, 45 minutes at 4M, and 60 minutes at 5 M, with signal blockade mean on the x-axis, with results consistent with the two-state loop hypothesis, and consistent with the observation of such in FIG. 1 not due to zero or weak urea content but due to high strain due to mass and charge effects upon binding to the large streptavidin molecule.

FIG. 11 illustrates a Y-laser transducer for high-specificity binding detection or individual protein binding and conformational change study. In FIG. 11 the Y-transducer is meant to have a study molecule, region 9, attached by a single stranded nucleic acid linker, region 10, that is possibly abasic (non-base-pairing), that is linked to a single stranded nucleic acid region, region 11 & 12, that is meant to anneal to a second nucleic acid to create the Y-shaped nucleic acid construct shown. The annealed Y-transducer is comprised of two, possibly LNA/RNA/DNA chimeric, nucleic acids, where the first single stranded nucleic acid is indicated by regions 1-3 and 7-8 and the second nucleic acid is indicated by regions 10-12. The paired regions {1,12}, {2,7}, and {8,11} are meant to be complements of one another (with standard Watson-Crick base-pairing), and designed such that the annealed Y-transducer molecule is meant to be dominated by one folding conformation (as shown). Region 3 is a biotin-modified thymidine loop, typically 4-5 dT in size (here 5dT shown with 2 dT, a biotinylated dT, then another 2 dTs), that is designed to be too large for entry and capture in the alpha-hemolysin channel, such that the annealed Y-transducer only has one orientation of capture in the nanopore detector (without bead, region 4, attached). Region 4 is a streptavidin coated magnetic bead (that is susceptible to laser-tweezer impulses). The base region, comprising regions {1,9}, is designed to form a duplex nucleic acid that produces a toggling blockade when captured in a nanopore detector. The typical length of the base-paired regions is usually 8, 9 or 10 base-pairs. The study molecule (region 9), an antibody for example, has linkage to single stranded nucleic acid via a commoditized process due to the immuno-PCR industry so is an inexpensive well-established manufacturing approach for the molecular construction. The Y-transducer on the left will not form if the 'immuno-PCR tagged' antibody is not present (see FIG. 7B for a variant without this limitation), which provides an additional level of event detection validation. If region 9 is a DNA enzyme that is progressively acting on a DNA substrate this provides a new means for nucleic acid sequencing.

FIGS. 12A-12B illustrate a Y-transducer for high-specificity dual-aptamer binding detection. In FIG. 12A the Y-transducer is meant to have two high-specificity aptamers attached by single stranded, possibly abasic (non-base-pairing), nucleic acid linkers, with region 8 for the left arm linker to the left arm aptamer in region 7 and region 3 for the right arm linker to the right arm aptamer in region 4. The sketch of the aptamers in regions 4 and 7 is meant to suggest the 3D conformational aspect of the aptamer, where stacking of G-quadruplexes is a common, but not necessary, feature of aptamers. The Y-transducer is comprised of three, possibly RNA/DNA chimeric, nucleic acids, where the first single stranded nucleic acid is indicated by regions 1-4, the second single stranded nucleic acid is indicated by regions 5 and 6, and the third nucleic acid is indicated by regions 7-10. The paired regions {1,10}, {2,5}, and {6,9} are meant to be complements of one another (with standard Watson-Crick base-pairing), and designed such that the annealed Y-transducer molecule is meant to be dominated by one folding conformation (as shown). The base region, comprising regions {1,10}, is designed to form a duplex nucleic acid that produces a toggling blockade when captured in a nanopore detector. The typical length of the base-paired regions is usually 9 or 10 base-pairs. The same Y-transducer is shown in FIG. 12B, but with a binding target, object 11, positioned for a chelation-type binding configuration, this in addition to any possible chelation binding on the part of the individual aptamers during their individual binding to object 11.

Figure 13:
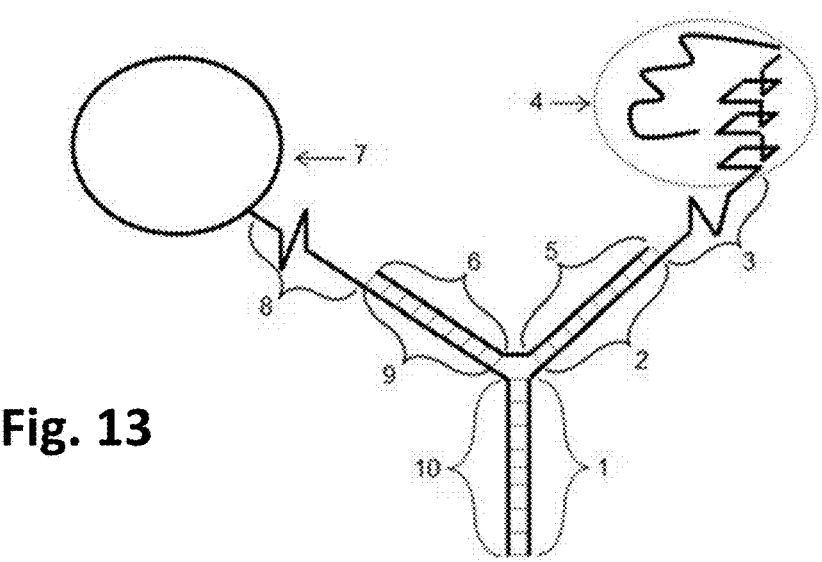
FIG. 13 illustrates a Y-transducer for high-specificity dual aptamer/antibody binding detection.

FIG. 13 illustrates a Y-transducer for high-specificity dual aptamer/antibody binding detection. In FIG. 13 the Y-transducer is meant to have an aptamer and an antibody attached by single stranded, possibly abasic (non-base-pairing), nucleic acid linkers, with region 8 for the left arm linker to the left arm antibody in region 7 and region 3 for the right arm linker to the right arm aptamer in region 4. The sketch of the aptamer in region 4 is meant to suggest the 3D conformational aspect of the aptamer, where stacking of G-quadruplexes is a common, but not necessary, feature of aptamers. The Y-transducer is comprised of three, possibly RNA/DNA chimeric, nucleic acids, where the first single stranded nucleic acid is indicated by regions 1-4, the second single stranded nucleic acid is indicated by regions 5 and 6, and the third nucleic acid is indicated by regions 8-10 is linked to the antibody shown as region 7. The antibody linkage to single stranded nucleic acid is a commoditized process due to the immuno-PCR industry so is an inexpensive well-established manufacturing approach for the molecular construction. The paired regions {1,10}, {2,5}, and {6,9} are meant to be complements of one another (with standard Watson-Crick base-pairing), and designed such that the annealed Y-transducer molecule is meant to be dominated by one folding conformation (as shown). The base region, comprising regions {1,10}, is designed to form a duplex nucleic acid that produces a toggling blockade when captured in a nanopore detector. The typical length of the base-paired regions is usually 9 or 10 base-pairs.

Figure 14:
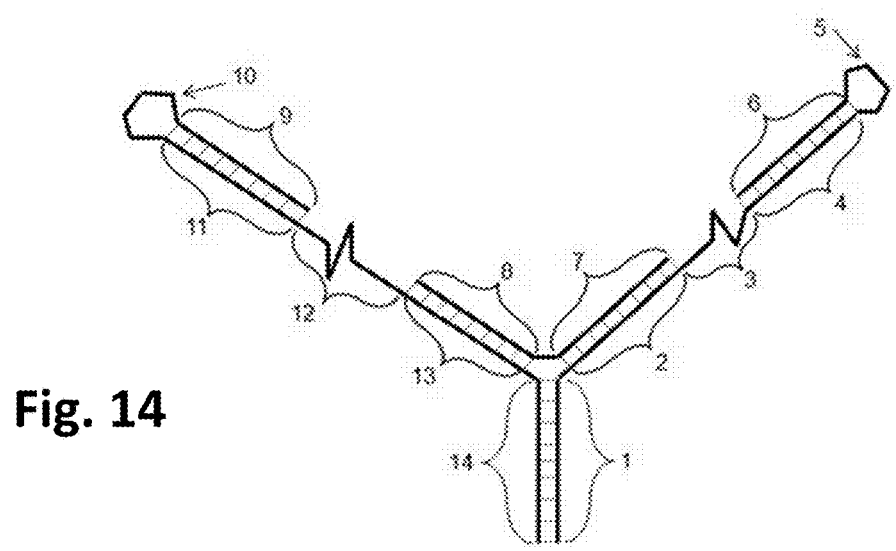
FIG. 14 illustrates a Y-transducer for dual testing for presence of specified viral digests.

FIG. 14 illustrates a Y-transducer for dual testing for presence of specified viral digests. In FIG. 14 the Y-transducer shown is meant to have the complementary single stranded nucleic acid annealing-based binding site encoded in region 3 for a specified viral digest sequence target. Region 12 is another such binding-site, for the same or a different viral digest sequence target. The Y-transducer is comprised of three, possibly RNA/DNA chimeric, nucleic acids, where the first single stranded nucleic acid is indicated by regions 1-6, the second nucleic acid is indicated by regions 7-8, and the third nucleic acid is indicated by regions 9-14. The paired regions {1,14}, {2,7}, {4,6}, {8,13} and {9,11} are meant to be complements of one another (with standard Watson-Crick base-pairing), and designed such that the annealed Y-transducer molecule (without miRNA binding) is meant to be dominated by one folding conformation (as shown). The regions 5 and 10 are loops, typically 4 dT in size, that are designed to be too large for entry and capture in the alpha-hemolysin channel, such that the annealed Y-transducer only has one orientation of capture in the nanopore detector. The base region, comprising regions {1,14}, is designed to form a duplex nucleic acid that produces a toggling blockade when captured in a nanopore detector. The typical length of the base-paired regions is usually 9 or 10 base-pairs.

Two twist conformations, due to different configurations in the hairpin loop and stem duplex conformation (such as B, B*, or A/B conformation duplex DNA), have been suspected from results on the DNA hairpins under other strain conditions, such as high voltage settings. Thus, it is consistent that two types of DNA hairpin channel blockade modes appear in the laser-tweezer experiments. The two modes are thought to be rigid-body configuration changing, or 'toggling', and internal configuration changing, or 'twisting'. Although the resulting toggle/twist mode signal analysis is more complicated when working with channel modulators, especially if induced by laser-tweezer, this is actually a highly favorable result. This is because a bound transducer that can provide a modulatory state by use of a bead attachment with laser excitation, even with two types of modulation signal resulting, is still a very manageable situation. Thus, the stochastic carrier wave analysis can proceed as before, only with more training data needed to 'learn' the more complicated background 'carrier wave' signal's characteristics. This is good news because the new mode types don't appear to proliferate beyond the new twist modes seen, and, thus, the transducer problem remains tractable with laser-tweezer generalized (ubiquitous) transducer design. Also, there is the ability to turn the twist mode type of internal signaling to our advantage in specialized transducer designs, as will be seen in the following.

The problem with the DNA transducers that are too easily melted, and the internal mode transmission (excessive twist mode) transducers, is they have too much internal freedom. If it was possible to lock-up' some of the internal twist motion, then a stronger hairpin might result, and one less likely to have twist modulations on top of toggle modulations. Such nucleic acid variants exist and are known as locked nucleic acid nucleosides ("LNA"s). They are a nucleic acid analogue where the ribose ring is locked into a highly favorable configuration for Watson-Crick base-pairing. The locking is accomplished by forming a methylene bridge from the 2'-O atom to the 4'-C atom of the ribose ring. LNA oligonucleotides can be synthesized using standard phosphoamidite chemistry (e.g., is compatible with standard enzymatic processes) and can be incorporated into chimeras with RNA and DNA. The high affinity of LNA for complementary RNA provides improved specificity and stability, and is resistant to exo- and endonucleases for use in both in vivo and in vitro settings. The increased affinity leads to much more stable LNA hairpin and other LNA duplex configurations. This has special significance in the NTD setting where specially designed DNA hairpin and Y-transducer molecules have already been identified for use as event transduction molecules, and minor alterations on these transducers for the LNA form are disclosed herein that will retain the transduction properties, but now with the long-lived and improved specificity and affinity attributes of LNAs. LNA versions of the biotinylated hairpins are disclosed herein, where streptavidin binding occurs where one twist appears to dominate, and the lifetimes of the LNA/DNA chimeric transducer molecules in the high-strain capture environment of the nanopore is now on the order of hours instead of minutes.

Figure 15:
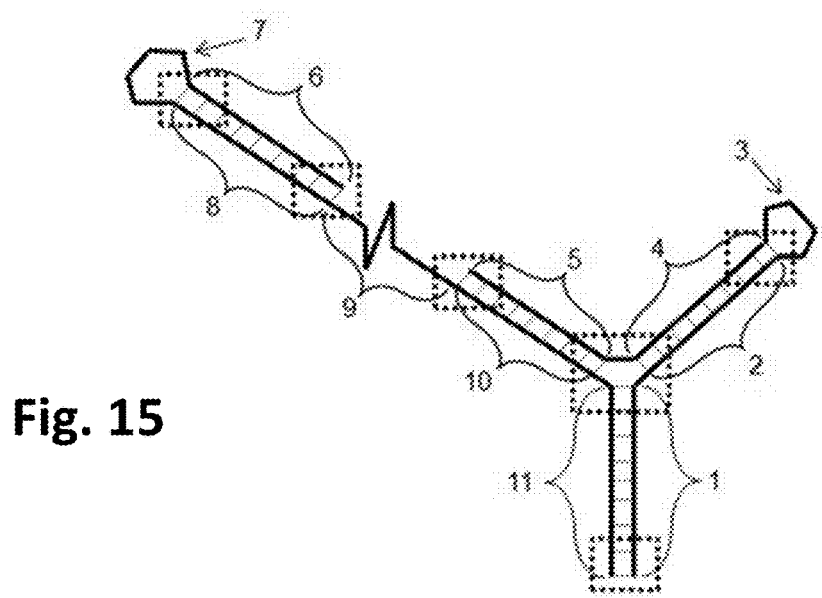
FIG. 15 illustrates a Y-transducer for annealing-detection for presence of specified viral digests.

The generic Y-transducer for annealing-based detection with no laser-tweezer needed could, thus, have a form shown in FIG. 15, where the regions with high LNA content are shown in dashed boxes, so as to protect the molecule in those regions from terminus fraying, loop opening, or nexus opening. FIG. 15 illustrates a Y-transducer for annealing-detection for presence of specified viral digests. The boxed regions indicate favorable areas for LNA substitution to protect the molecule in those regions from base-pair fraying at the terminus, loop-opening, or nexus-branchings.

Figure 16:
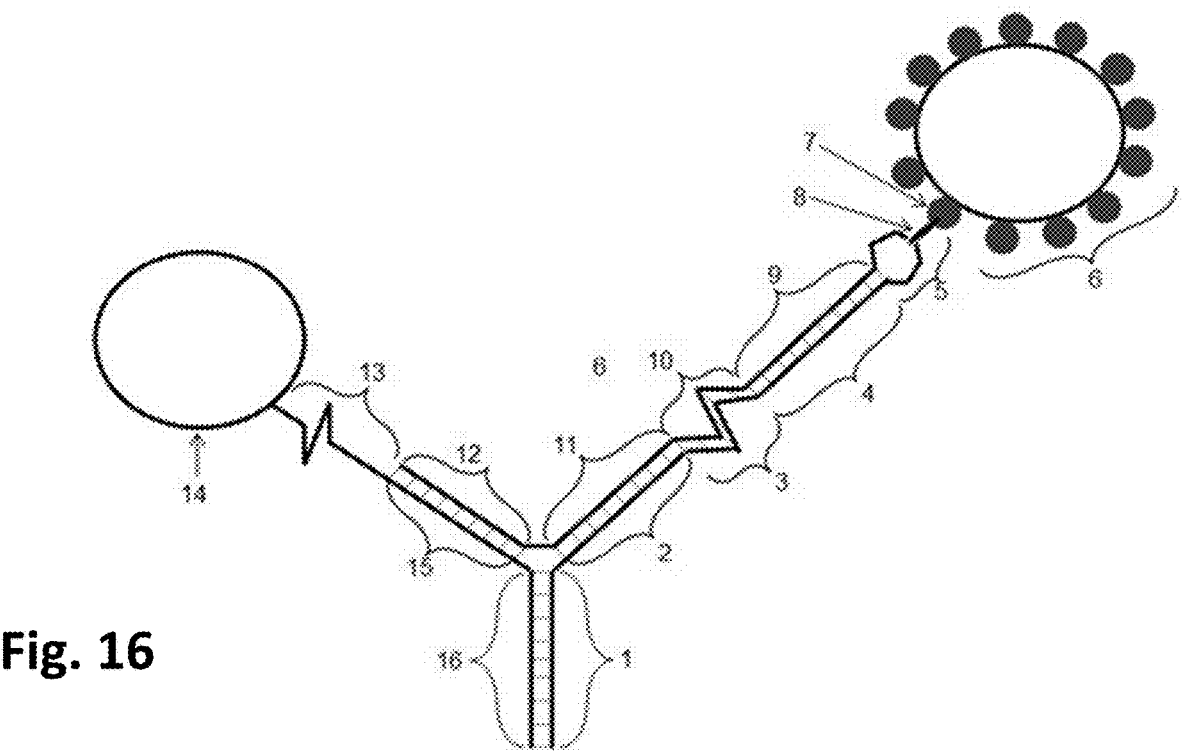
FIG. 16 illustrates a Y-transducer for single molecule studies using twist mode modulations.
Figure 17:
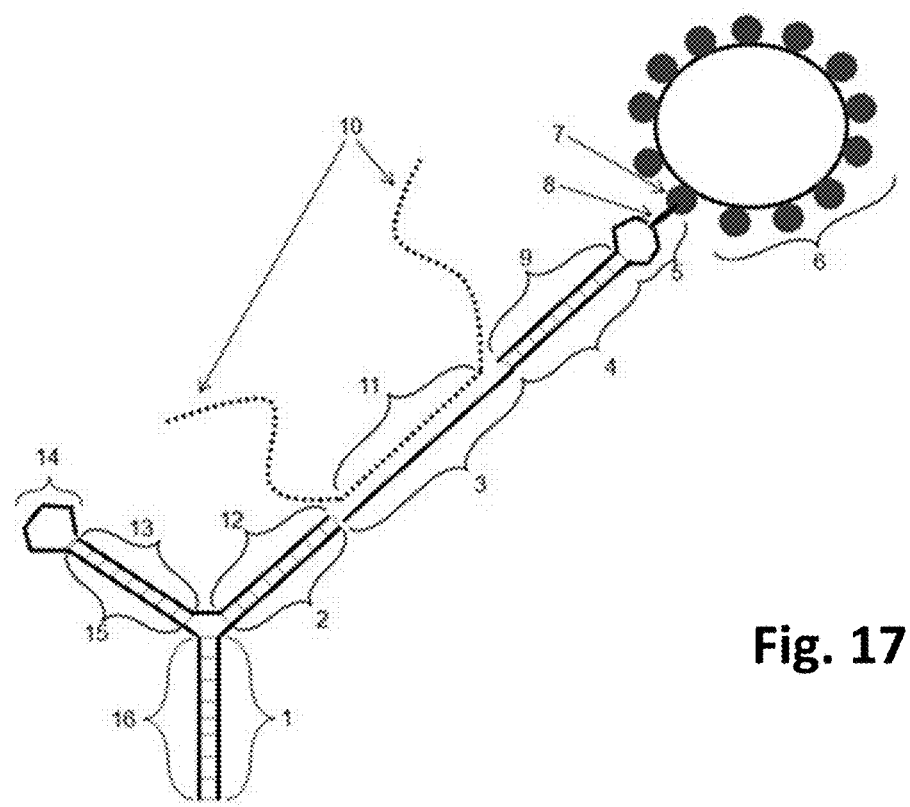
FIG. 17 illustrates a Y-transducer for single molecule annealing studies using twist mode modulations.
Figure 18:
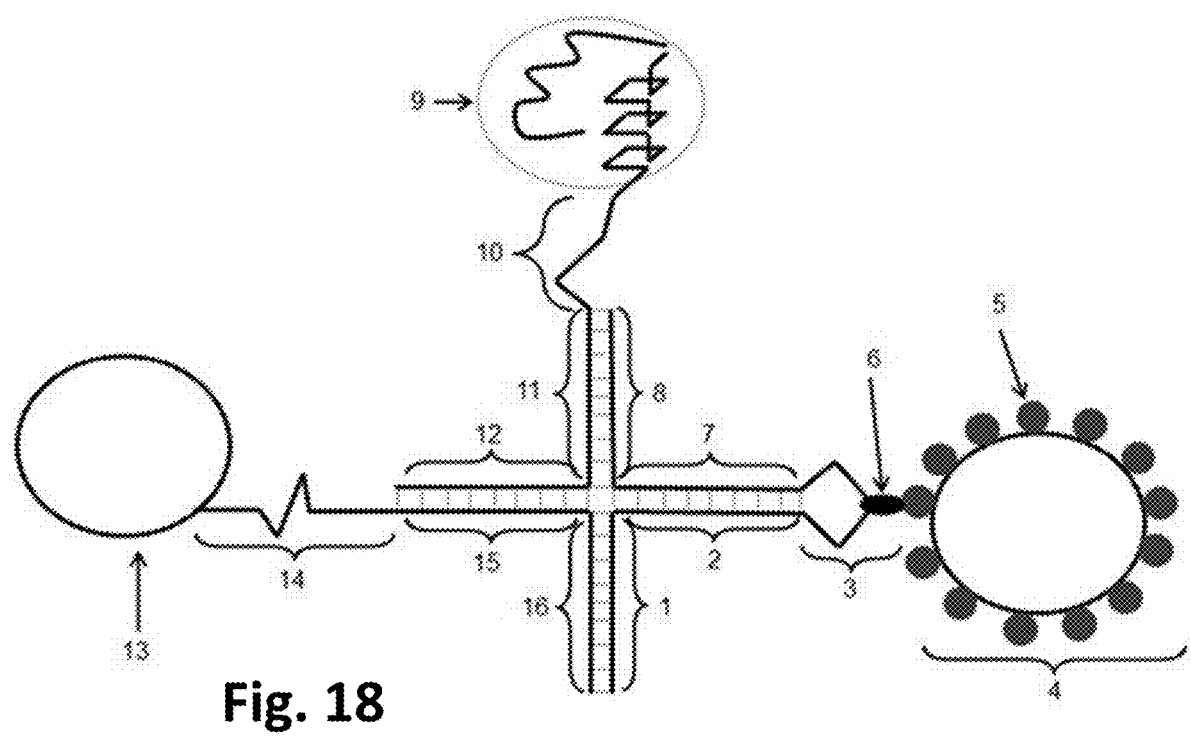
FIG. 18 illustrates a 4-way transducer.

FIG. 16 illustrates a Y-transducer for single molecule studies using twist mode modulations. FIG. 17 illustrates a Y-transducer for single molecule annealing studies using twist mode modulations. FIG. 17 shows an even more 'twist mode' specialized Y-transducer for single molecule annealing studies using twist mode modulations. Nucleic acids can be arranged in other useful geometries than the three-way 'Y' junctions used thus far. FIG. 18 illustrates a 4-way transducer (a.k.a, a Holliday Junction transducer), or X-transducer, for dual aptamer/antibody tissue-targeting functional aptamer delivery studies, where a modulatory transducer is enabled by laser-tweezer coupling. Details on the Y-transducer constructs shown in FIGS. 16-17 are disclosed as follows.

In FIG. 16 the Y-transducer region 14 indicates the study molecule of interest (an antibody for antibody-detection or a protein for conformation/binding studies), where a magnetic bead is attached for laser-tweezer modulation (region 6), where the transducer is designed with sufficient LNA substitutions to allow laser-tweezer excitations to be transmitted as a twist-mode impulse (shown in regions numbered {3,10}) while maintaining discernibly different signals according to the study molecules state. Paired regions {1,16}, {2,11}, {4,9}, {12,15} are designed to anneal with the dominant conformation shown, and are typically a minimum of 8 or 9 base-pairs in length. The linker arm in Region 13 and Region {12,15}, is whatever is needed to provide sufficient steric clearance between region 14 and region 6 when the stem (region {1,16}) is captured and held at the nanopore.

In FIG. 17 the Y-transducer region 10 indicates the single stranded nucleic acid study molecule of interest: a nucleic acid whose region 10 section is annealed to region 3 of the transducer; where a magnetic bead is attached for laser-tweezer modulation (region 6), where the transducer is designed with sufficient LNA substitutions to allow laser-tweezer excitations to be transmitted as a twist-mode impulse through the annealed-target region. A twist mode will only transmit if the annealing-target is bound, giving rise to very different channel modulation signals. Paired regions {1,16}, {2,12}, {4,9}, {13,15} are designed to anneal with the dominant conformation shown, and are typically a minimum of 8 or 9 base-pairs in length. The loop in Region 14 is designed to not favor channel capture and strongly favor a single conformation for the Region 13-15 stem-loop region.

The Y-shaped DNA transduction molecule is also a versatile construct to test for as an intermediate annealed complex, as evidenced in single nucleotide polymorphism SNP detection efforts. Highly accurate SNP detection with the Y-shaped DNA transduction molecule was possible by designing the Y-transducer to anneal to nucleic acid target sequence such that the SNP variant occurs in the Y-nexus region, giving rise to a clear difference in the annealed Y-transducer's channel modulation. The NTD method provided a means to perform SNP variant detection to very high accuracy, and will likely be improved further when using the higher specificity LNA form of the transducers indicated by the LNA improvements disclosed below.

Use of Chaotropes to Improve Signal Resolution

In the nucleic acid annealing studies on the NTD platform described in FIG. 5, the critical role of chaotropes for robust nucleic acid annealing studies on the NTD platform was revealed. The ability of the NTD apparatus to tolerate high chaotrope concentration, up to 5M urea, was demonstrated more recently, where the DNA hairpin control molecules demonstrated a manageable amount of isoform variation even at 5M urea, as shown in FIG. 10.

Managing Common Interference Agents and Antibodies as Easily Identifiable Interference or Transducer The electrophoretic mechanism of the NTD detector operation in embodiments provides a large advantage over known solutions when dealing with possible contaminants. Electrophoresis is used to drive strong negative charges to the nanopore detector during normal operation. This means that nucleic acids will be separated and driven to the detector, along with certain proteins and other molecules that have a low pI. Most proteins with low pI are found to have very little interaction with the nanopore channel, however, the main exception being antibodies. To take a stringent set of conditions as an example, consider the common level of interference agents used to demonstrate robust medical testing applications, shown in Table 1 below. Actual levels of interference agents seen in (healthy) human blood samples are far lower, shown in Table 2 below.

TABLE 1

| | |
|---|---|
| Bilirubin: | 10 mg/dL = 0.10 mg/mL |
| Cholesterol: | 800 mg/dL = 8.00 mg/mL |
| Hemoglobin: | 250 mg/dL = 2.50 mg/mL |
| Triglyceride: | 500 mg/dL = 5 mg/mL |

TABLE 2

| | |
|---|---|
| Bilirubin | 5 mg/L (10 uM) |
| Cholesterol (healthy) | <2 mg/mL (5 mM) |
| Hemoglobin in plasma | 2 mg/dL = 0.02 mg/mL (300 nM) |
| Hemoglobin in whole blood | 150 mg/mL (2.5 mM) |
| Triglyceride | 1 g/L (1 mM) |
| Serum DNA (no cell ruptures) | 1-200 ng/ml |
| Albumin | 35-50 g/L (600 uM) |
| Immunoglobulin G (IgG) | 15 mg/mL (at 160 kDa → 93.75 nmol/mL) |
| Urea | 15 mg/dL (3 mM) |
| Glucose (fasting) | 100 mg/dL (5 mM) |

For example, consider working with a 1 uL sample (such as with a pinprick sample) that contains high levels of common interference agents from blood, or other biological sources, Table 3 below shows the very high contaminant levels that have been tested on the NTD in embodiments with very low concentrations of reporter molecule, and the reporter molecules are easily discerned. So most interference agents pose little channel interaction and the occasional channel blockade that does occur is short and non-modulatory. The main exception is antibodies, where a single monoclonal antibody (mAb) is found to produce a variety of distinct channel modulation signals types. Some mAb blockades produce a very clean toggling between two levels, as shown in FIGS. 19-22 below, such as that of the 9GC DNA hairpin blockade signal. The modulatory signals are easily discerned from each other, however, especially with increased observation time as needed (part of the auto-eject tuning). Aside from being an interference agent, antibodies offer a direct means for having a NTD transducer since their modulatory blockade signals are observed to change upon introduction of antigen (to produce distinctively new signals only associated with introduction of the antigen and not the antigen alone). The problem with using an antibody directly as a transducer in a biosensor arrangement is that the antibody produces multiple blockade signal types (a dozen or more) just by itself (without binding). This weakness for use directly as a biosensor (they can still be linked indirectly) is because the antibody is a glycoprotein that has numerous heterogeneous glycosylations and glycations, with many molecular side-groups that might be captured by the nanopore detector to produce modulatory blockades. If the purpose is to study the post-translational modifications (PTMs) themselves, a glyco-profile of the antibody in other words, then the numerous signal types seen are precisely the information desired.

TABLE 3

| | |
|---|---|
| Cholesterol (healthy) | 8 mg/mL > 2 mg/mL |
| Hemoglobin | 4 mg/mL > 2.5 mg/mL |
| Immunoglobulin G (IgG) | 30 mg/mL > 15 mg/mL |
| Urea | >5M >> 3 mM |
| Glucose | >>50 mM > 5 mM |

Figure 19:
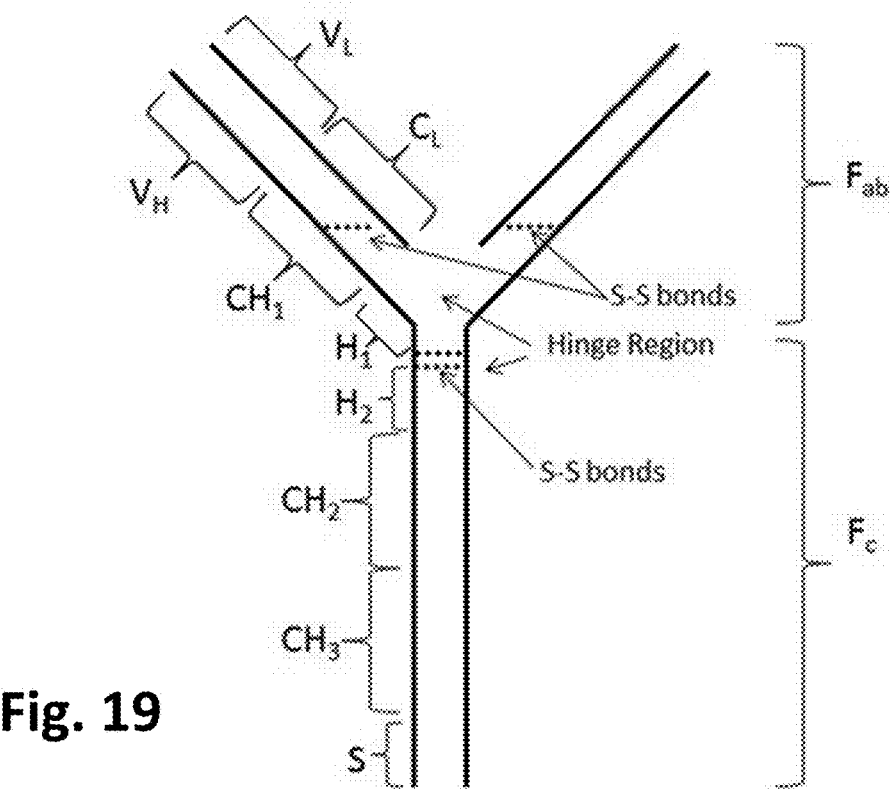
FIG. 19 illustrates a standard antibody schematic.

Antibodies are the secreted form of an associated B-cell receptor, where the difference between receptor and secreted forms is in the C-terminus of the heavy chain region. FIG. 19 illustrates a standard antibody schematic. Standard notation is shown for the constant heavy chain sequence ('CH', 'H', and 'S' parts), variable heavy chain region ('VH' part), the variable light chain region ('VL' part), and constant light chain region ('CL' part). The equine IGHD gene for the constant portion of the heavy chain has exons corresponding with each of the sections CH1,H1,H2,CH2,CH3,CH4(S), and for the membrane-bound form of IGHD, there are two additional exons, M1 and M2 for the transmembrane part, thus, CH1,H1,H2,CH2,CH3,CH4(S),M1,M2. In FIG. 19, the full heavy chain sequence is derived from recombination of the VH part and {CH,H,S} parts (where the secretory region S is also called CH4). In FIG. 19, the long and short chains are symmetric from left to right, their glycosylations, however, are generally not symmetric. Critical di-sulfide bonds are shown connecting between chains, each of the VH and CH regions typically have an internal disulfide bond as well. The lower portion of the antibody is water soluble and can be crystallized (denoted Fc). The upper portion of the antibody is the antigen binding part (denoted Fab).

Figure 20:
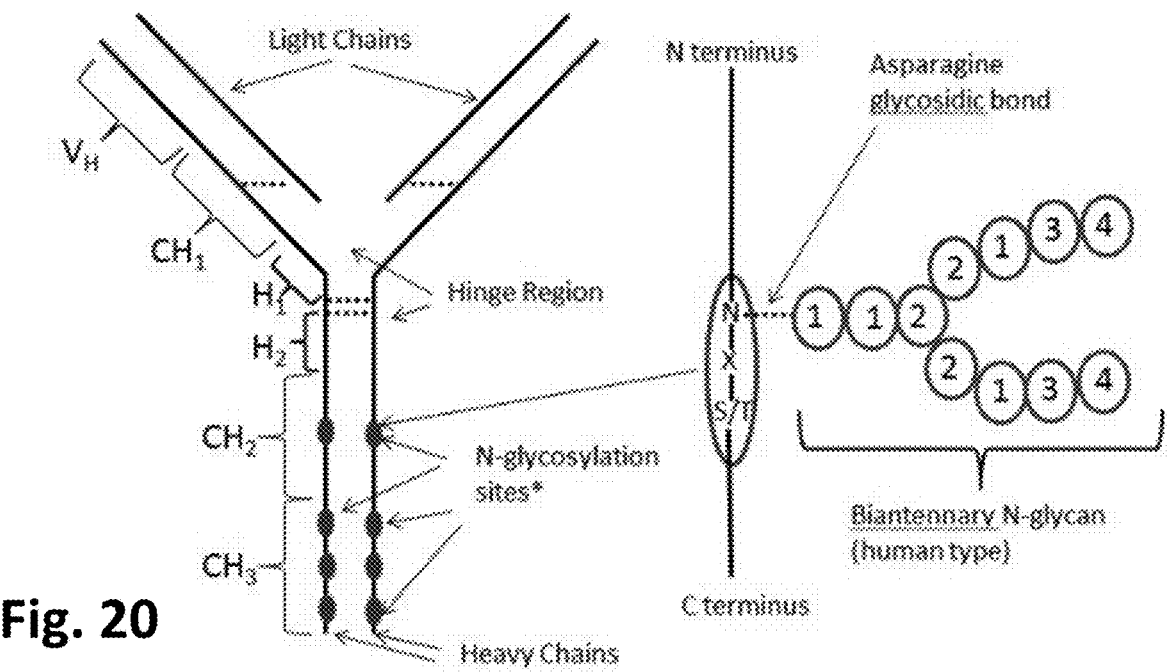
FIG. 20 illustrates a typical antibody N-glycosylation.

FIG. 20 illustrates a typical antibody N-glycosylation (exact example for equine IGHD). One possible N-glycosylation site is indicated in region CH2, and three possible N-glycosylation sites are indicated in region CH3. N-glycosylation consists of a covalent bond (glycosidic) between a biantennary N-glycan (in humans) and asparagine (amino acid 'N', thus N-glycan). The covalent glycosidic bond is enzymatically established in one of the most complex post translational modifications on protein in the cell's ER and Golgi organelles, and usually only occurs in regions with sequence "NX(S/T)—C-terminus" where X is 'anything but proline' and the sequence is oriented with the C-terminus as shown. Licensed therapeutic antibodies typically display 32 types of biantennary N-glycans, consisting of N-acetylglucosamine residues (GlcNAc, regions '1'); mannose residues (Man, regions '2'); galactose residues (Gal, regions '3'), and Sialic Acid Residues (NeuAc, regions '4'), as shown in FIG. 20. The N-glycans are classified according to their degree of sialylation and number of galactose residues: if disialylated (shown) have A2 class. If asymmetric and monosialylated have A1 class. If not sialylated then neutral (N class). If two galactose residues (shown) then G2 class, if one, then G1 class, if zero, then G0 class. If there is an extra GlcNAc residue bisecting between the two antennae +Bi class (–Bi shown). If a core fucose is present (location near GlcNAc at base), then +F (–F shown). So the class shown is G2-A2. The breakdown on the 32 types is as follows: 4 G2-A2; 8 G2-A1; 4 G1-A1; 4 G2-A0; 7 G1-A0; 4 G0-A0. The N-glycans with significant acidity (A2 and A1) are 16 of the 32, so roughly half of the N-glycans enhance acidity. The other main glycosylation, involving 0-glycans, occurs at serine or threonine (S/T). The main non-enzymatic glycations occur spontaneously at lysines ('K') in proteins in the blood stream upon exposure to glucose via the reversible Maillard reaction to form a Schiff Base (cross-linking and further reactions, however, are irreversible and associated with the aging process).

Figure 21:
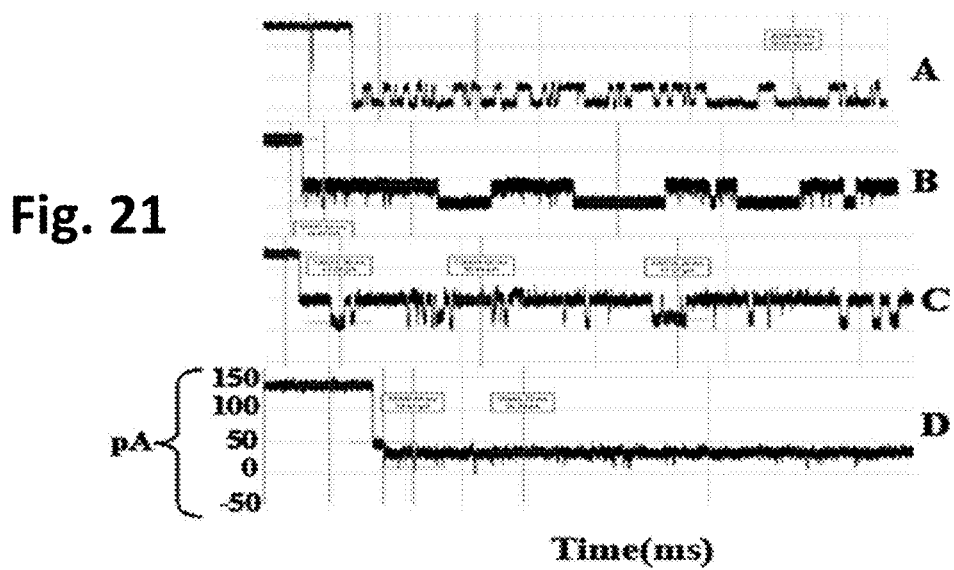
FIG. 21 illustrates multiple antibody blockade signal classes.
Figure 22:
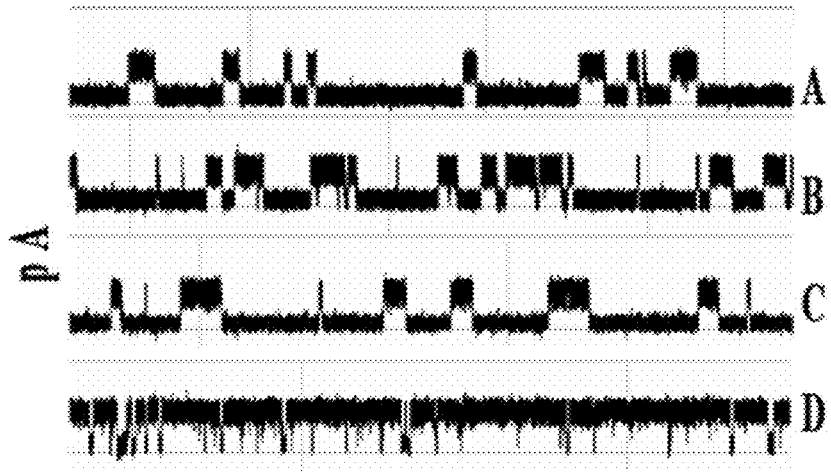
FIG. 22 illustrates Antibody-Antigen binding.
Figure 23:
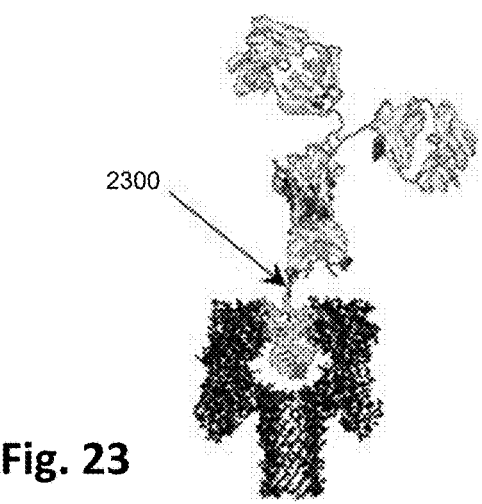
FIG. 23 illustrates a DNA hairpin bound to an antibody via an EDC-linker.
Figure 24:
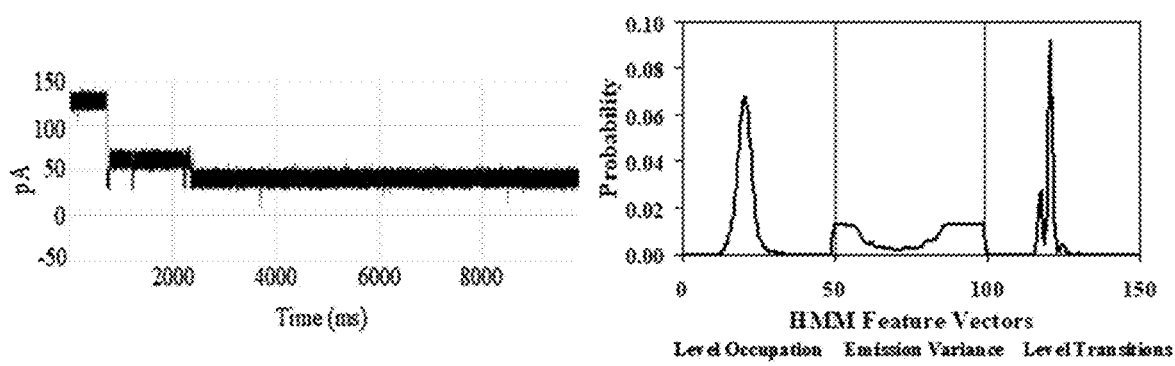
FIG. 24 illustrates an antibody linked to DNA-Hairpin Blockade signal and HMM Profile.
Figure 25:
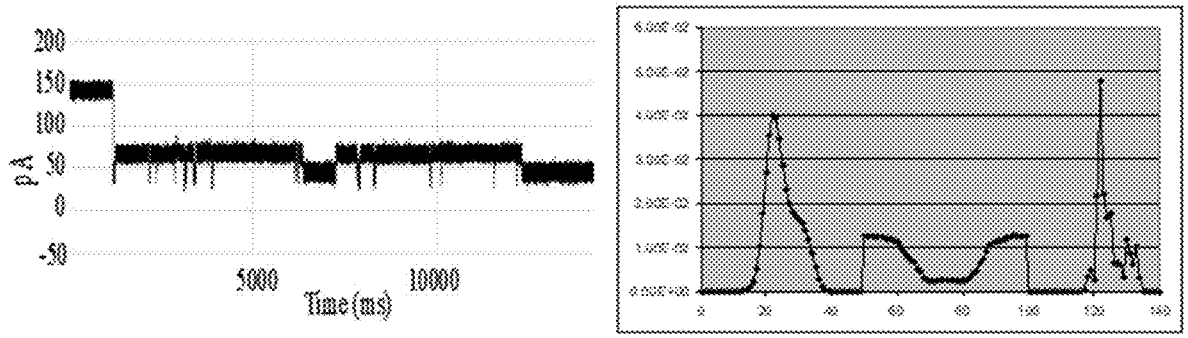
FIG. 25 illustrates an antibody linked to DNA-Hairpin.

The base of the antibody plays the key role in modulating immune cell activity. The base is called the Fc region for 'fragment, crystallizable', which is the case, and to differentiate it from the Fab region for 'fragment, antigen-binding' that is found in each of the arms of the Y-shaped antibody molecule, shown in FIG. 19. The Fc region triggers an appropriate immune response for a given antigen (bound by the Fab region). The Fab region gives the antibody its antigen specificity; the Fc region gives the antibody its class effect. IgG and IgA Fc regions can bind to receptors on neutrophils and macrophages to connect antigen with phagocyte, known as opsonization (opsonins attach antigens to phagocytes). This key detail explains the modulatory antibody interaction with the nanopore channel. IgG, IgA, and IgM can also activate complement pathways whereby C3b and C4b can act as the desired opsonins. The C-termini and Fc glycosylations of an antibody's heavy chain, especially for IgG, is thus a highly selected construct that appears to be what is recognized by immune receptors, and is evidently what is recognized as distinct channel modulator signals in the case of the NTD (mAb channel blockade signals are shown in FIG. 21). FIG. 21 illustrates multiple antibody blockade signal classes. FIG. 21 includes examples of the various IgG region captures and their associated toggle signals: the four most common blockade signals produced upon introduction of a mAb to the nanopore detector's analyte chamber (the cis-channel side, typically with negative electrode). Other signal blockades are observed as well, but less frequently or rarely.

Using NTD, embodiments can co-opt the opsonization receptor-binding role of the Fc glycosylations (and mAB glycations and glycosylations in general), and C-terminus region, to be a channel modulating role. This may also permit a new manner of study of the critical opsonization role of certain classes of antibodies (and possibly differentiate the classes in more refined ways) by use of the nanopore detector platform. The channel can provide a means to directly measure and characterize antibody Fc glycosylations, a critical quality control needed in antibody therapeutics to have correct human-type glycosylation profiles in order to not (prematurely) evoke an immunogenic response. Some of the antibody blockade signals are deep blockades like the nine-base-pair DNA hairpin blockades. Working with these very clear signals, that have stable modulating blockades that go for hours, experiments for embodiments were performed with the addition of small amounts of antigen (see FIG. 22). FIG. 22 illustrates Antibody-Antigen binding—a clear example from specific capture orientation. Each trace shows the first 750 ms of a three minute recording, beginning with the blockade signal by an antibody molecule that has inserted (some portion) into the Alpha-hemolysin channel to produce a toggle signal (A). Antigen is introduced at the beginning of frame A (100 μg/ml of 200 kD multivalent synthetic polypeptide (Y,E)-A-K). Changes to the toggle signal are discernible in frame D, indicating the binding event between the antibody and antigen has taken place.

One of the largest human-type Fc glycosylations, G2-A2+Bi+F, has a molecular weight about 2.7 kDa, which is about half the molecular weight of the eight base-pair hairpin, so provides a similar size for similar blockade. It would appear that a variety of C-terminus modifications and Fc glycosylations would be appropriately sized and charged for channel capture, and this is what is shown in FIG. 21. For some antibody signals, antigen binding can be seen noisier versions of the antibody signal (especially if antigen is small, like biotin), for other antibody signals, antigen presentation leads to a very different, and still clearly defined signal. An example of this for antigen a 200 kD multivalent synthetic polypeptide (Y,E)-A-K is shown in FIG. 22. Similar results can be seen with binding on biotin as well, showing that glycosylations, particularly in the hinge region (CH2), play a critical role in coupling conformational change associated with binding in the Fab region with receptor presentation in the Fc region. On the occasions when the antibody has a 'good' glycosylation, it more effectively transduces its binding as a change in Fc region. If the antibody has an EDC linkage to a DNA hairpin modulator, a unique Ab capture orientation results (dominated by the much lower pI DNA hairpin part) and antibody binding is still seen, even for small antigen, such as for the biotin as antigen experiment shown in FIGS. 23-25 below.

FIG. 23 illustrates a DNA hairpin bound to an antibody via an EDC-linker. In FIG. 23 the molecules are only approximately shown to scale. Arrow 2300 points to the Internal Amino Thymine Modification with Primary Amine on a six carbon spacer arm. Primary amine can be cross-linked using 1-Ethyl-3-(3-dimethylaminopropyl) carbodiimide hydrochloride (EDC) to the peptide carboxyl terminus of the antibody heavy chain. This crosslinkage results in a covalent bond between the primary amine and the carboxyl.

FIG. 24 illustrates an antibody linked to DNA-Hairpin Blockade signal and HMM Profile. FIG. 25 illustrates an antibody linked to DNA-Hairpin, now bound to its target antigen (biotin)—new blockade signal, and associated HMM profile. Antigen binding to an EDC-linked Antibody/DNA-Hairpin, where the stem of the hairpin is captured in the NTD.

Embodiments of antibody blockades for the nanopore detector include the use of a well defined synthetic polypeptide antigen. Similar results are found IgG subclass 1 monoclonal antibodies for biotin, HIV, and anti-GFP, and all have produced similar signals. The critical role of Fc glycosylation is disclosed above, but there is also the critical role in understanding antigen-antibody binding in the Fab region. Hydrophobic bonds are very difficult to characterize by existing crystallographic and other means, and often contribute half of the overall binding strength of the antigen-antibody bond. Hydrophobic groups of the biomolecules exclude water while forming lock and key complementary shapes. The importance of the hydrophobic bonds in protein-protein interactions, and of critically placed waters of hydration, and the complex conformational negotiation whereby they are established, may be accessible to direct study using nanopore detection methods.

Channel Current Cheminformatics ("CCC")

In the NTD platform in accordance to embodiments, sensitivity increases with observation time in contrast to translocation technologies where the observation window is fixed to the time it takes for a molecule to move through the channel. Part of the sensitivity and versatility of the NTD platform derives from the ability to couple real-time adaptive signal processing algorithms to the complex blockade current signals generated by the captured transducer molecule. Embodiments deployed as a biosensor platform, possesses highly beneficial characteristics from multiple technologies: the specificity of antibody or aptamer binding, the sensitivity of an engineered channel modulator to specific environmental change, and the robustness of the electrophoresis platform in handling biological samples.

Nanopore Detector Experiments in Accordance with Embodiments

Each experiment is conducted using one alpha-hemolysin channel inserted into a diphytanoyl-phosphatidylcholine/hexadecane bilayer across a, typically, 20-micron-diameter horizontal Teflon aperture. The alpha-hemolysin pore has a 2.0 nm width allowing a dsDNA molecule to be captured (while a ssDNA molecule translocates). The effective diameter of the bilayer ranges mainly between 5-25 μm (1 μm is the smallest examined). This value has some fluctuation depending on the condition of the aperture, which station is used (each nanopore station, there are four, has its own multiple aperture selections), and the bilayer applied on a day to day basis. Seventy microliter chambers on either side of the bilayer contain 1.0 M KCl buffered at pH 8.0 (10 mM HEPES/KOH) except in the case of buffer experiments where the salt concentration, pH, or identity may be varied. Voltage is applied across the bilayer between Ag—AgCl electrodes. DNA control probes are typically added to the cis chamber at 10-20 nM final concentration. All experiments are maintained at room temperature (23±0.1° C.), using a Peltier device.

NTD Control Probes

The five DNA hairpins below have been carefully characterized, so are used as highly sensitive controls (obtained from IDT DNA with PAGE purification). The nine base-pair hairpin molecules share an eight base-pair hairpin core sequence, with addition of one of the four permutations of Watson-Crick base-pairs that may exist at the blunt end terminus, i.e., 5'-G|C-3', 5'-T|A-3', and 5'-A|T-3'. Denoted 9GC, 9CG, 9TA, and 9AT, respectively. The full sequence for the 9GC hairpin is 5'-GTTCGAACGTT TTCGTTCGAAC-3' (SEQ ID NO: 3). The eight base-pair DNA hairpin (8GC) is identical to the core eight base-pair part of the 9GC sequence, except the terminal base-pair is changed to be 5'-G|C-3' (e.g., 5'-GTCGAACGTT TTCGTTCGAC-3' (SEQ ID NO: 4)). Each hairpin was designed to adopt one base-paired structure.

NTD Y-Transducer/Reporter Probe

The Y-shaped NTD-transducer molecule design used in single nucleotide polymorphisms experiments has a three-way DNA nexus geometry: 5'-CTCCGTCGAC GAGTT-TATAGAC TTTT GTCTATAAACTC GCAGTCATGC TTTT GCATGACTGC GTCGACGGAG-3' (SEQ ID NO: 5). Two of the junctions' arms terminate in a 4T-loop and the remaining arm, of length 10 base-pairs, is usually designed to be blunt ended. The blunt ended arm, or 'stem', has been designed such that when it is captured by the nanopore it produces a toggling blockade. Variants of the Y-transducer sequence are indicated in the figures for the Y-transducer annealing experiments.

Biotinylated DNA Probes (from IDT DNA, Purification by PAGE)

```
8GC-BiodT:
                                    (SEQ ID NO: 6)
5'-GTCGAACGTT/iBiodT/TTCGTTCGAC-3'

9GC-BiodT:
                                    (SEQ ID NO: 7)
5'-GTTCGAACGTT/iBiodT/TTCGTTCGAAC-3'
```

Biotinylated LNA/DNA Chimeric Probes (from Exiqon, Purification by H PLC)

```
8GC-BiodT:
                                    (SEQ ID NO: 16)
5'- + G + TCGAA + C + GTT/iBiodT/TT + CGT + T +
CG + AC-3'.
```

The LNA version of 8GC-Bt has 8 LNA bases shown preceded by '+', 12 DNA bases, and 1 biotin dT base.

```
9GC-BiodT:
                                    (SEQ ID NO: 8)
5'-+G+CTTGAA+C+GT/iBiodT/TT+CGTT+CAA+GC-3'.
```

The LNA version of 9GC-Bt stem does not have the same exactly the sequence as the DNA-based 9GC, and has only a 3dT loop aside from the modified dT with biotin attachment, and has 7 LNA bases shown preceded by '+', 14 DNA bases, and 1 biotin dT base.

Laser Trapping Probes (from IDT DNA, Purification by H PLC)

The 20 bp hairpin with 4dT loop:

```
9GC-ext:
                                    (SEQ ID NO: 9)
5'-GTTCGAACGGGTGAGGGCGCTTTTGCGCCCTCACCCGTTCGAAC-3'
```

The 20 bp hairpin with 5dT loop, where the central loop dT was modified to have a linker to biotin:

9GC-BiodT-ext: 5'-

```
9GC-BiodT-ext:
                                    (SEQ ID NO: 10)
5'-GTTCGAACGGGTGAGGGCGCTT/iBiodT/TTGCGCCCTCACCCGTT
CGAAC-3'
```

Laser Setup

Laser illumination provided by a Coherent Radius 635-25. Output power before fiber optic was 25 mW at a wavelength of 635 nm. The beam was chopped at 4 Hz. During laser excitation studies the Faraday cage was removed. Significant 60 Hz wall-power noise was not seen with case removed when there was no laser illumination, but with cage removed and under laser illumination 60 Hz line noise could clearly be seen. After fiber optic, approximately 5-10 mW illumination in an approximate 1 mm illumination diameter was produced at the nanopore detector's aperture.

Antibody/Antigen Design, Synthesis, and Purification

For most of the antibody experiments a panel of native and genetically engineered antibodies to a well defined synthetic polypeptide antigen are used, (Y, E)-A-K. The antigen-binding characteristics, ability to form immune complexes, and effector functions of these antibodies have been carefully studied. Three different antibodies from this set are utilized in the experiments in this experimental effort. All have identical variable domains of murine origin, but one is a murine IgG1, one a human IgG1, and the other a human IgG4. All monoclonal antibodies are grown in tissue culture because ascites preparations are inflammatory exudates subjecting the antibodies to the potential of proteolytic digestion, attachment of complement components and so forth. Cells are either grown in medium containing fetal calf serum adsorbed on protein G to remove remaining Ig, or in serum free hybridoma medium. To test the effect of preparation method, murine IgG1 antibody is either purified by ammonium sulfate precipitation, antigen-affinity purification or protein G chromatography. All other antibodies are routinely purified on protein G and eluted with 0.5 M glycine-HCl pH 2.5, immediately neutralized, and dialyzed into phosphate buffered saline (PBS). Once antibodies are purified, they are run on SDS-PAGE to confirm purity and run on IEF prepoured gels (Biorad) to determine PI. Antigen binding is confirmed by the immunoassay technique of ELISA (enzyme-linked immunosorbent assay, a biochemical technique to identify the presence of antibody or antigen) in PBS and in 1 M KCl (so long as that buffer is used).

Mouse Anti-Biotin Monoclonal Antibody

In the experiments with Anti-Biotin Antibody, monoclonal IgG1 from Stressgen was used at the concentration of 1.0 mg/mL. Horseradish peroxidase (HRP) was conjugated with affinity purified mouse immunoglobulin in phosphate buffered saline (PBS) at pH 7.2 with 0.1 mM PMSF and 50% glycerol. The Immunogen was unbound Biotin.

Anti-Biotin Antibody Linkage to a DNA Hairpin Nanopore-Probe

In the experiments with antibiotin antibodies, they were stored at −20 C as supplied, were brought to a final dilution 1-4 μg/mL in the electrolyte chamber. Ab-DNA conjugation was performed with 1-Ethyl-3-(3-Dimethylaminopropyl) carbodiimine Hydrochloride (EDC), in accordance with the instructions of Manufacturer (Pierce, Rockford, Ill.).

Data Acquisition and FSA-Based Signal Acquisition

Data is acquired and processed in two ways depending on the experimental objectives: (i) using commercial software from Axon Instruments (Redwood City, Calif.) to acquire data, where current was typically filtered at 50 kHz bandwidth using an analog low pass Bessel filter and recorded at 20 μs intervals using an Axopatch 200B amplifier (Axon Instruments, Foster City, Calif.) coupled to an Axon Digidata 1200 digitizer. Applied potential was 120 mV (trans side positive) unless otherwise noted. In some experiments, semi-automated analysis of transition level blockades, current, and duration were performed using Clampex (Axon Instruments, Foster City, Calif.). (ii) using LabView based experimental automation. In this case, ionic current was also acquired using an Axopatch 200B patch clamp amplifier (Axon Instruments, Foster City, Calif.), but it was then recorded using a NI-MIO-16E-4 National Instruments data acquisition card (National Instruments, Austin Tex.). In the LabView format, data was low-pass filtered by the amplifier unit at 50 kHz, and recorded at 20 µs intervals. Signal acquisition from the 20 µs sample stream was done using a Finite State Automaton ("FSA").

HMM-Based Signal Feature Extraction

With completion of FSA preprocessing, an HMM is used to remove noise from the acquired signals, and to extract features from them. The HMM in one configuration (for control probe validation) is implemented with fifty states, corresponding to current blockades in 1% increments ranging from 20% residual current to 69% residual current. The HMM states, numbered 0 to 49, corresponded to the 50 different current blockade levels in the sequences that are processed. The state emission parameters of the HMM are initially set so that the state j, $0<=j<=49$ corresponding to level $L=j+20$, can emit all possible levels, with the probability distribution over emitted levels set to a discretized Gaussian with mean L and unit variance. All transitions between states are possible, and initially are equally likely. Each blockade signature is de-noised by 5 rounds of Expectation-Maximization ("EM") training on the parameters of the HMM. After the EM iterations, 150 parameters are extracted from the HMM. The 150 feature vectors obtained from the 50-state HMM-EM/Viterbi implementation are: the 50 dwell percentage in the different blockade levels (from the Viterbi trace-back states), the 50 variances of the emission probability distributions associated with the different states, and the 50 merged transition probabilities from the primary and secondary blockade occupation levels (fits to two-state dominant modulatory blockade signals). Variations on the HMM 50 state implementation are made as necessary to encompass the signal classes disclosed herein.

SVM-Based Classification

The 150-component feature vector extracted for each blockade signal is then classified using a trained Support Vector Machine (SVM). The SVM training is done off-line using data acquired with only one type of molecule present for the training data (bag learning).

Pattern Recognition Informed (PRI) Sampling

Figure 26:
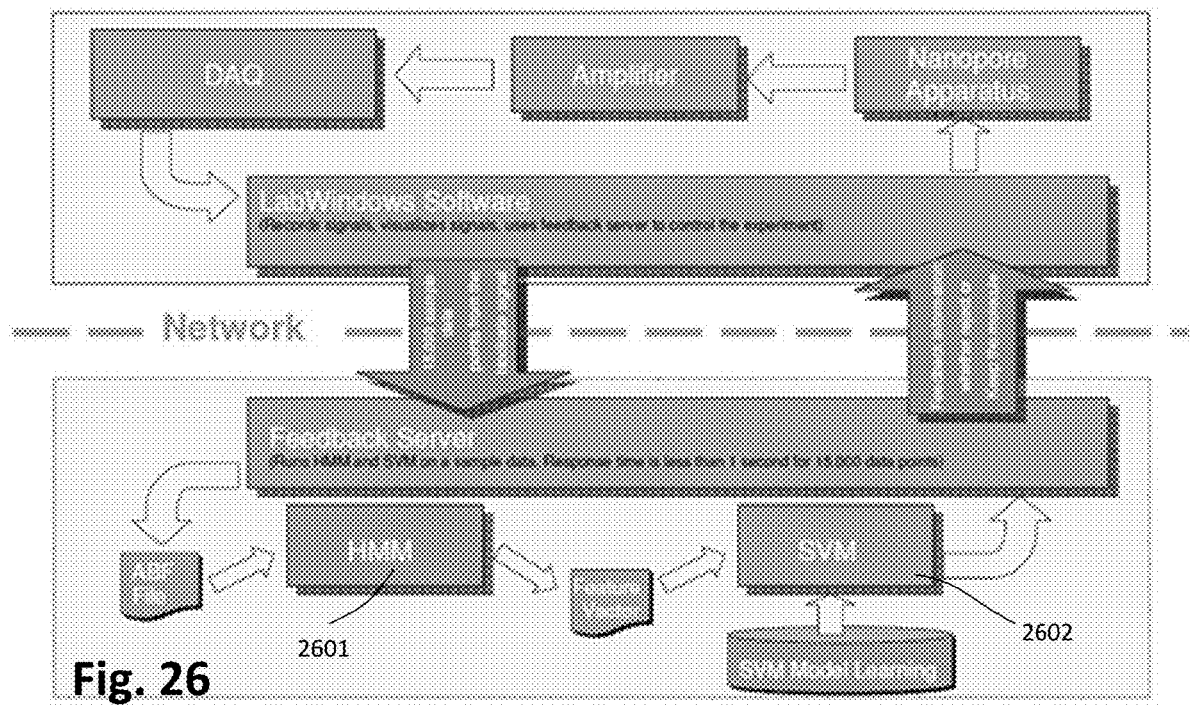
FIG. 26 illustrates a system for implementing embodiments of the invention.

FIG. 26 illustrates a system for implementing embodiments of the invention. For experiments with PRI sampling, a capture signal generated with the nanopore apparatus is filtered and amplified before it is sent through the DAQ. The data acquisition device converts the analog signal to digital format for use in the display and recording of data in binary Axon (Molecular Devices) format. In the pattern recognition feedback loop, the first 200 ms detected after drop from baseline are sent via TCP-IP protocol to the HMM software, which generates a profile for each signal sent. The HMM-generated profile is processed with the SVM classifier to compare the real-time signal with previous training data in order to determine whether the signal is acceptable. FIG. 26 illustrates a Labwindows/Feedback Server Architecture with distributed CCC processing. The HMM learning 2601 (on-line) and SVM learning 2602 (off-line), are network distributed processes for N-fold speed-up, where N is the number of computational threads in the cluster network. FIG. 26 includes a processor with computer-readable memory for storing instructions that, when executed by the processor, implements functionality disclosed herein.

If the signal is acceptable, the message to continue recording is sent to the LabWindows software to continue recording, and the molecule is not ejected from the channel by the amplifier. If not, a message is sent to LabWindows to eject the molecule, and the amplifier briefly reverses the polarity to eject the molecule from the channel. The nanopore experiments with PRI sampling are first done with a 1:70 mixture of 9GC:9TA.

Background information regarding HMM and SVM processing is disclosed in U.S. Pat. Pub. No. 2013/0071837, the disclosure of which is hereby incorporated by reference.

Figure 27:
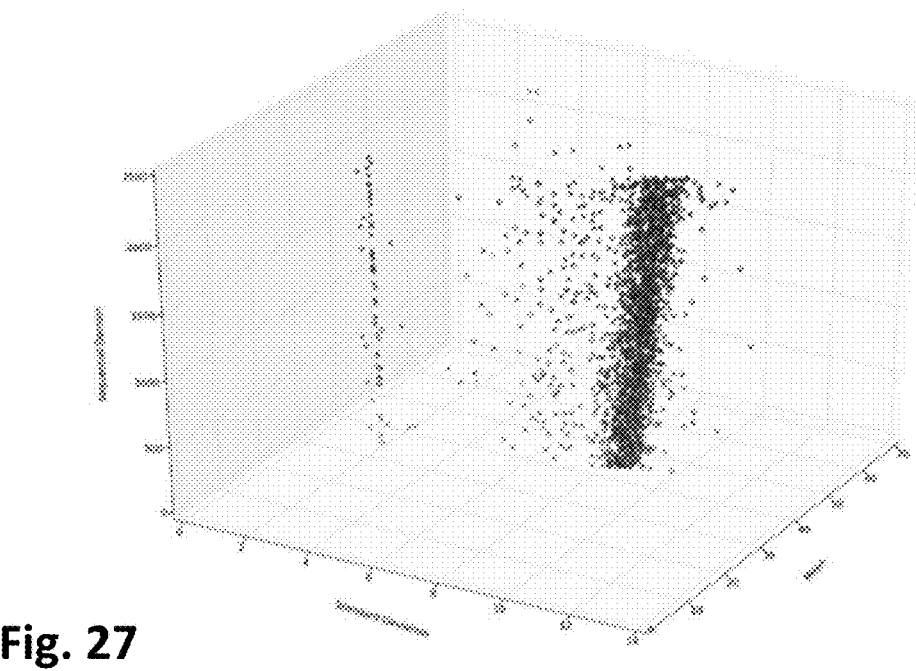
FIG. 27 illustrates how molecules appear in terms of their blockade attributes in the on-line setting.

FIG. 27 illustrates how molecules appear in terms of their blockade attributes in the on-line setting (with event-observation time on the vertical axis). FIG. 27 illustrates standard deviation vs. mean vs event-observation time (vertical axis). Drift in the {9GC,9TA} signal is seen as the experiment proceeds due to evaporative concentration of the background salt. This results in altered environment for the DNA hairpins, one where the increasing magnitude of the blockade std. deviations is thought to be due to stronger (and noisier) DNA hairpin channel blockades.

Figure 28:
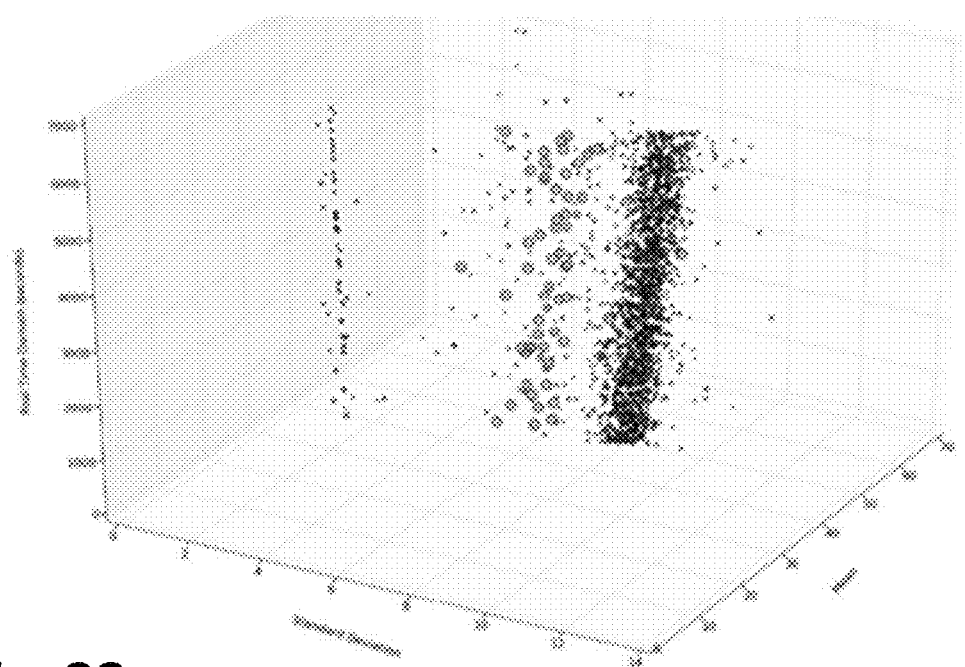
FIG. 28 illustrates the standard deviation vs. mean vs event-observation time vs PRI-informed sample observation time.

FIG. 28 illustrates the standard deviation vs. mean vs event-observation time vs PRI-informed sample observation time (4th dimension represented as the radius of the data point). This figure shows a successful real-time operation on the PRI-sampling method on the ND platform. 9GC signal is selected for observation and it is at a 1:70 lower concentration than the decoy 9TA DNA hairpins. As can be seen, only 9GC signals are held for the lengthier observation time, all other molecules being rejected promptly upon identification (the smaller diameter events points correspond to short lived events), where the brief duration of the event is dictated by the active, PRI-control, of the device voltage. In FIG. 28 the PRI sampling acquisition results are shown, with the rarer 9GC molecules properly identified, and sampled for a full 5 second duration, while other molecules are rejected, typically in a fraction of a second (with the prototype network setup used here). The robustness of the results are then explored when there are numerous other classes present.

Figure 29:
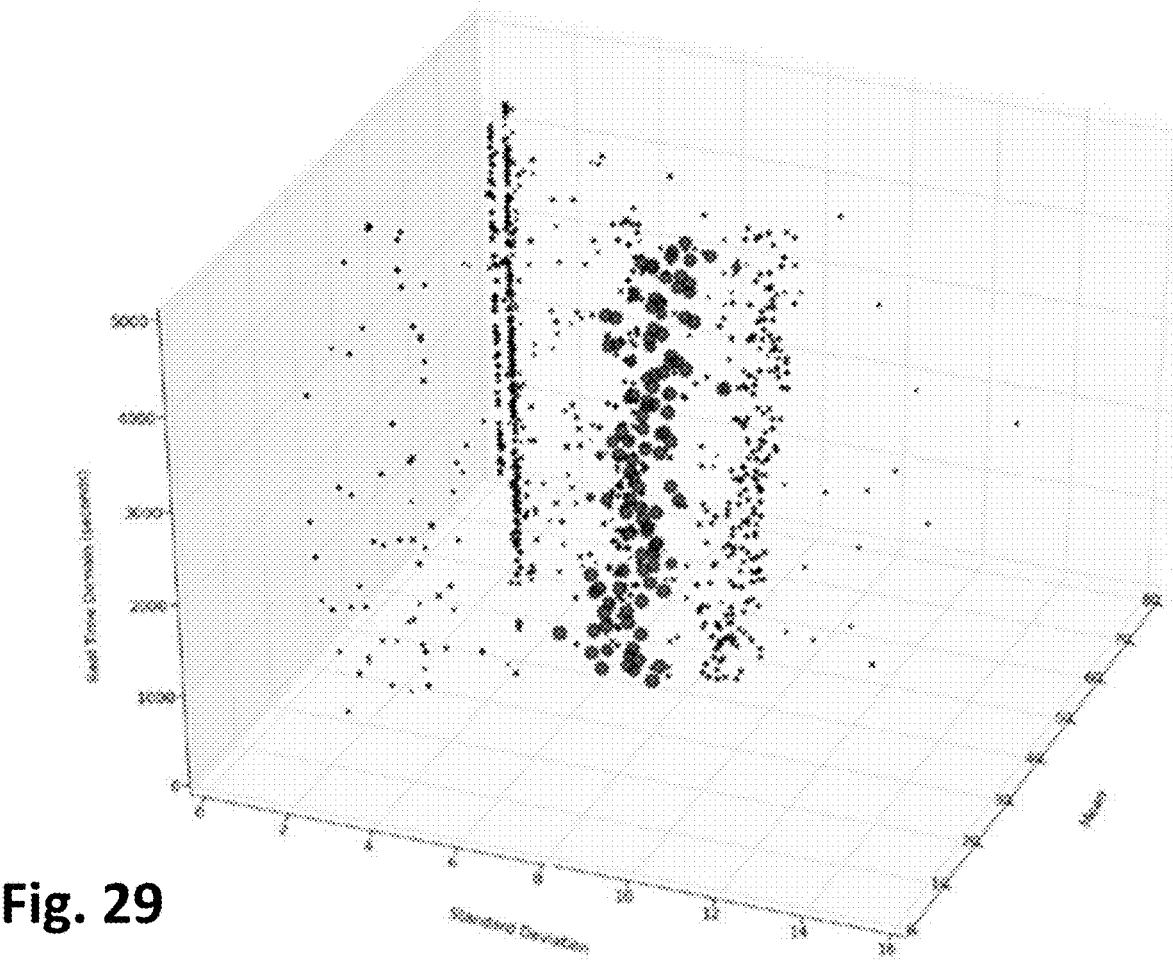
FIG. 29 illustrates standard deviation vs. mean vs event-observation time (vertical axis) vs PRI-informed sample observation time.
Figure 30:
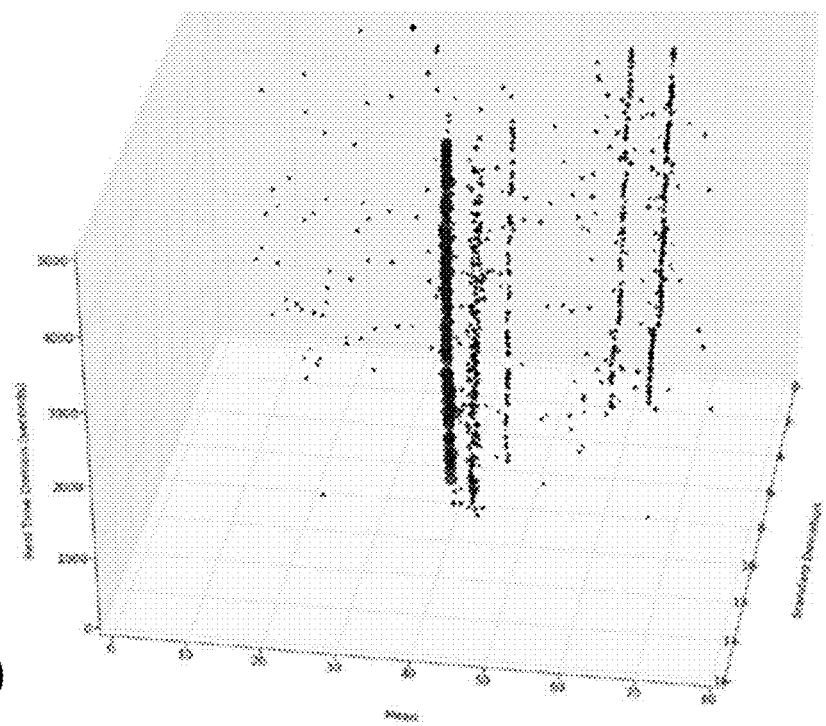
FIG. 30 illustrates a rotated view of the results shown in FIG. 29.

FIG. 29 illustrates standard deviation vs. mean vs event-observation time (vertical axis) vs PRI-informed sample observation time (4th dimension represented as the radius of the data point). In FIG. 29, an approximately 1:70 mixture of 9GC:{6GC,7GC,8GC,9TA} is examined, with 9GC sample time again boosted correctly as indicated. Drift in the signal is seen as the experiment proceeds, as before. Similar strong classification performance is demonstrated for this five-class test as with the prior two-class test. FIG. 30 illustrates a rotated view of the results shown in FIG. 29. The successful 99.9% accurate separation of the 9GC from the {6GC,7GC,8GC,9TA} signals can be seen more clearly from this perspective. The actual discriminating features used by the SVM classifier are not based on the mean and standard deviation statistical features plotted, but on a 150-component feature extraction based on HMM emission and transition probabilities, and Viterbi-path statistics.

In embodiments, the robustness of the channel is further shown when exposed to interference agents. Some agents if present with sufficiently high concentration, however, can damage the bilayer. Albumin is an example of such and it is the main protein found in blood samples. Albumin can intercalate into the bilayer (cholesterol also) and initially this strengthens the bilayer and lowers the system RMS current noise, but eventually there is too much of a good thing and the albumin is probably agglomerating and causing bilayer disruption, which, in turn, can compromise the entire experiment. There are a variety of buffer modifications that can be introduced that are protective of the bilayer, including blocking the albumin intercalation. In doing so, however, new interference molecules are introduced that can damage the channel. It is observed, however, that the new interference problem is only a problem if the protocol is non-responsive, e.g. if the blockade is not recognized as a 'bad' blockade and ejected promptly (if not ejected promptly the molecule gets 'stuck'). What is needed is an auto-eject cycle for whatever minimal observation time is needed per blockade in the experiment of interest, to minimize channel blockade time regardless. What is also needed is good and bad signal recognition. Generally any signal that is modulating is good, so if all signals are rejected if non-modulatory in their first 0.5 seconds is a pretty good operational setting. The PRI sampling can thus be employed, indirectly, to provide channel protection and maintain operational status for prolonged periods.

Uses of NTD in Accordance with Embodiments

Biological System Analysis

A growing number of questions facing molecular and medicinal biology experts are systems biology questions, where the complex interaction of genes, messenger RNAs ("mRNAs"), proteins, microRNAs ("miRNAs"), and various metabolites is described at the 'system level'. System level problems are often described in terms of 'gene circuits' or 'metabolic algorithms'. These comparisons to system descriptions in electrical engineering and computer science offer some insights due to actual parallels, and some misleading comparisons due to oversimplification in comparison to actual biological systems.

A reductionist analysis of a biological system, not surprisingly, reveals that the sum is greater than its parts. But this is actually found to be the case in electrical circuits as well, where emergent properties, especially emergent noise and communications properties, are often found in circuits with feedback. Even simple physical systems involving just three bodies in classical orbital dynamics gives rise to chaotic behavior, which was not expected in physics, where the sum was originally NOT thought to be greater than its parts. Iterative dynamical systems in general are found to exhibit chaotic behavior and emergent constructs such as strange attractors and limit cycles. Systems with feedback, thus, can do surprising things, and biological systems definitely have done some surprising things ranging from living systems in their amazing variety to complex phenomena such as intelligence, language, and consciousness.

The nanopore transduction detector (NTD) method is typically based on a single protein-channel biosensor implemented on a lipid bilayer (synthetic cell membrane), but it could also be implemented as a live cell assay by using the original patch clamp protocol for measuring current through a channel on a live cell. In order for the NTD 'voltmeter' to operate on the biological system to work, cell-based or not (e.g., with in vitro or in vivo studies), the normal operational buffer of the NTD must accommodate a change to the physiological or cellular buffer environment of the biological system of interest, and, if cell-based, the 'carrier signal' that is the basis of the analysis can no longer be channel-current based, but channel-noise based with use of laser modulations for noise state excitation. Recent work with robust NTD operation with a variety of buffer pH and in the presence of high concentrations of interference agents reveals that operational stability with a wide range of buffers has been achieved. Laser modulations have also been introduced to improve the NTD mechanism to have more general applicability, and for purposes of establishing an improved 'stochastic carrier wave' molecular state tracking capability, so many of the complications with returning to the single-cell application are mostly solved. A system and method for a NTD-based biological system 'voltmeter' is thus described for both in vivo and in vitro applications.

Comparison of Electrical Circuit and Biological Circuits: The Biological Extra Element Theorem (Beet)

A reductionist analysis of electrical circuits involves a reduction to circuit elements that have linear responses. In this regard biology only compares weakly, as the components of a biological circuit are generally non-linear over much of their operational range. Even so, for a particular biological system setting sufficiently small perturbations in the biological components can often be made such that they provide a linear system response. Given the complexity of the biological feedback systems, however, this might seem to be small progress. It is very significant, however, given the existence of a sophisticated method from advanced circuit design and analysis that is applicable for linear response systems known as the 'extra element theorem'. It interesting to note that this important circuit method from electrical system theory has not been imported into biological system discussions given its likely significant role in molecular evolutionary theory. The extra element theorem from electrical circuit theory allows simpler circuits, that are more easily understood, to have new components added (the 'extra' element), and if the new component happens to create a feedback loop, then the complexity of the feedback loop analysis can be much more easily evaluated and understood directly by way of the extra element theorem. In practice, very complex electrical amplifier circuits can be built-up and analyzed in this way, by repeated use of the extra element theorem. This offers the means to have a reductionist analysis while capturing the growing complexity of holistic irreducible systems. What results is a biological variant of the extra element theorem, applicable across a patchwork of linear response regimes for a particular biological system.

The 'messengers' in biological and electrical systems differ greatly in many respects, which can make some gene circuit intuition entirely misguided. The carriers in an electrical circuit, for example, are remarkably simple by comparison with biological system signal carriers. Electrical charge moves through wires like a fluid. Granted, the electrical charge moves at a sizable fraction of the speed of light, but it is so like a fluid flow that some current flow discussions are basically plumbing discussions, where the description of the current flow is often compared to flow of water through pipes where pipe narrowness is akin to resistance, etc. The flow/interaction topology of electrical current is also self-evident in the connectivity that can be seen in the wiring of the circuit diagram. If the biological system is too interconnected in this comparison this is often where the analogy is shifted to discussions of a gene system algorithm. The electrical messengers, or charge carriers, are also vastly simpler than the biological system messengers. Electrical current carriers are of only one type (electrons), and don't have self-interactions like molecular carriers (as with dimerization . . . unless you are talking superconductivity), and don't have internal state (in the sense of the circuit model) like with biological secondary messengers. Biological system messengers, on the other hand, come in a huge variety, operate at the single molecule level, and depending on perspective, everything in the biological system might be considered a system messenger in a massive, living, autocatalytic cascade. The biological system carriers or messengers are also much fewer in number compared to their electrical counterparts. This actually makes things more complicated. In electronics having small currents is modelled as a noise source, where once the discreteness of the charge carriers begins to be discernible this puts one in the realm of stochastic 'shot' noise. In the biological comparison this stochastic underpinning, if significant, again favors a shift to the 'algorithm' analogy instead of the circuit analogy. To further complicate matters, the biological carriers of the system interactions interact with each other, and typically have internal states (e.g., proteins and riboswitches often have conformational states), so the picture of the carriers for biology introduces vastly greater complexity and interaction interconnectivity.

In electrical circuit analysis a good voltmeter is something that will not significantly 'load' or alter the circuit while measuring a particular component's voltage drop. Likewise, in analyzing a computer program, or resolving a runtime error (the closest analogy to analyzing a 'live' biological algorithm), one of the best tools available is to simply introduce a 'print statement' to track any internal state behavior of interest in the program. This is where weakness of the circuit or algorithm analogy in biological systems is most profound. The system biologist doesn't have a gene circuit voltmeter or gene system algorithm print statement. The closest that can be done with standard biochemistry methods are fluorescence based, and in certain specialized applications remarkable results have been obtained along these lines, but they typically involve the introduction of constructs with a great deal of effort that won't scale well to the vast number of biological systems that need to be studied in the post-genomic era. What is needed is a non-destructive, carrier non-modifying, means of testing 'live' biological systems, possibly in their native cellular environment.

Validation of miRNA's and miRNA Binding Sites Using A Nanopore Transduction Nanoscope The discovery of the RNA interference (RNAi) immune response and translational regulation mechanism has led to an explosion in the number of identified microRNAs (miRNAs) and their mRNA binding sites. An understanding of miRNAs and their binding sites, typically in the 3' untranslated region (3' UTRs) of mRNAs, is helping to explain a wide range of complex phenomena, ranging from latency control by viruses during infection (such as with HIV), to complex regulation in system syndromes such as in diabetes and in the effects of aging, to the general trans-regulation of mRNAs at the translational level (complementing transcription factor and promoter cis-regulation at the transcriptional level). The examination of miRNAs, and especially miRNA binding sites, is confounded by the small size of the miRNAs, however: 21-25 nucleotides in length for typical mature miRNAs, and only 7-8 base ssRNA seed regions in the guide-strand RNA incorporated into the RNAi's RISC complex for actual binding/repression to complementary 7-8 base sequence in the 3'UTR region of the target mRNA. For the latter case of verification for miRNA/RISC derived sequence binding with a 7 base sequence in a mRNA's 3'UTR there is further complication given possible posttranscriptional modifications, such as via inosine substitution for adenosine due to adenosine deaminases with inosine recognition as guanine in terms of base-pairing that can alter the actual target sequence of the miRNA/RISC binding. This is in addition to the obvious complication of identifying the presence of RNA annealing when the annealing only involves 7 bases of RNA.

Experimental results with NTD-based detection on short DNA annealing provides a means to examine the miRNA/ RISC binding to target 3'UTR region with or without the RISC complexes argonaute proteins intact. NTD based detection of DNA annealing has been demonstrated on DNA sequences as short as 5 bases, and in the presence of a variety of interference agents and chaotropes. NTD based detection has also been demonstrated in a variety of buffer conditions so could be established in a buffer conducive to the RISC complex remaining intact and where the annealing to 3'UTR complement sequence occurs with the binding strength found in vivo. NTD detection can also operate on small volumes since it makes use of a single protein channel interaction, thereby inherently operating at the single-molecule interaction level. NTD detection can, thus, identify single-molecule binding events in a non-destructive manner that may be conducive to the 'live' characterization of many critical, transient, interactions.

For biosensing or bioassays applications in general, not all miRNA or miRNA binding site analyses need be in cellular or physiological buffer either. In a 'destructive setting' more forceful miRNA validation assays, and analysis of annealing-based events, can be pursued by use of chaotropes such as urea. Clearer identification of collective binding events, such as for highly complementary annealing interactions, is found to occur upon introduction of chaotropes that eliminate non-specific DNA interactions, or many 'simple' binding interactions, not involving collective interactions of many components as with annealing.

Protein Conformation-Binding Relationships and Antibody Glyco-Profiles Using a Nanopore Transduction Detector Proteins, such as enzymes, can have a high degree of variability. It has been demonstrated that enzyme turnover rate, for example, can differ at the single molecule level, with a single enzyme observed with one constant turnover rate, while another enzyme, differing only in conformation, or possibly by a difference in glycation, has a different, but still constant, substrate processing rate. And this is a simple example where there is only one interaction region and it is (mostly) unchanging in its conformation for the individual protein examined. Some allosteric proteins, on the other hand, with multiple binding sites for a particular target, change their binding affinity according to how many ligands they have bound. Antibodies are known to change conformation during binding to one (or two) antigens in such a significant manner that this is the basis for activation of the complement cascade of the adaptive immune response.

Nanopore transduction detection is inherently a single-molecule analysis platform. An example of a transient interaction that has been specifically examined using the NTD system involves interaction of HIV integrase with its consensus DNA binding terminus. In this setting the NTD can be used as a drug-discovery assayer where measurements are made of the transient HIV interactions in the presence of interference agents or competitive inhibition molecules. If HIV integrase binding can be observed, it may be possible to use the nanopore detector to ascertain good candidates for disrupting the pathogenic integrase function. HIV integrase is a 32 kDa enzyme responsible for integrating the DNA version of HIV's genome into the host cell's DNA. It catalyzes the "cut-and-paste" operation of snipping the host DNA and attaching the proviral genome to the snipped ends. As a critical first step the integrase first clips off two nucleotides from the 3' end of the viral DNA that is produced by reverse transcription. (After that, it inserts the viral DNA strand into the host DNA.) HIV integrase binding to viral-DNA appears to be favor the high flexibility of a CA/TG dinucleotide positioned precisely two base-pairs from the blunt terminus of the duplex viral DNA. The CA/TG dinucleotide presence is a universal characteristic of retroviral genomes. Deletion of these base pairs impedes the integration process and it is believed that the unusual flexibility imparted by this base-pair on the terminus geometry is necessary for the binding to integrase. A test of the hypothesized flexibility/reactivity was performed by obtaining channel blockade signals on a set of DNA hairpins with a single CA dinucleotide step at different positions in the hairpin stem. Analysis of channel current statistics revealed that the blunt-ended HIV DNA conformer had notably different and more energetic blockade kinetics than the other blunt-ended hairpins in the CA set, indicative of a (non-obvious) enhanced flexibility/reactivity of the same molecule selected by integrase for enhanced interactivity. In related proof of concept studies involving single-integrase nanopore studies and the NTD method the integrase enzyme was examined in terms of its activity on substrate by using a Y-shaped DNA event transducer that had the aforementioned highly-frequency conformational switching CA/TG molecule with dinucleotide precisely two base-pairs from a blunt terminus at one arm of a Y-shaped DNA transducer. Enzyme activity in the presence of other cofactor species, such as magnesium, was examined in this setting as well.

The best picture of that protein's structure-function relationship is often derived from crystallographic information, where the standard crystallographic 'conformer' presents just one structure configuration. Typically, standard protein structure determination methods refer to a 'single molecule' structure indirectly, being inherently bulk assay methods, via use of crystallization or correlated spin motions (NMR), etc. FRET offers single-molecule resolution, but often at the cost of the fluorophores altering the native conformational structures and their conformational changes with a given dye attachment. For critical proteins of interest in the pre-genomic era it has been possible to triangulate complex protein behavior by a collection of the aforementioned methods, but in the post-genomic era there are just too many proteins to be studied and characterized. Crystallographic methods are greatly more complex with larger proteins, requiring that they be broken into smaller pieces, an arduous process requiring very talented biochemists and biophysicists to get the job done. Crystallographic methods must also struggle with difficulties if the protein of interest isn't solution soluble (e.g., membrane bound). What is needed is a means to examine protein behavior in its 'native' solution environment, at the single molecule level, such that the conformational state of an individual protein can be tracked during its interaction with other biomolecules of interest. The nanopore transduction detector (NTD) has been suggested for such an application, but only recently has the NTD operation been demonstrated for a wide range of pH, chaotrope concentration, and in the presence of interference agents that would encompass the 'native' environment of a protein of interest.

The NTD approach may provide a good means for examining enzymes as well, and other complex biomolecules, particularly their activity in the presence of different co-factors. There are two ways that these studies can be performed: (i) the enzyme is linked to the channel transducer, such that the enzyme's binding and conformational change activity may be directly observed and tracked, or (ii) the enzyme's substrate may be linked to the channel transducer and observation of enzyme activity on that substrate may then be examined. Case (i) provides a means to perform DNA sequencing if the enzyme is a nuclease, such as lambda exonuclease. Case (ii) provides a means to do screening, for example, against HIV integrase activity (for drug discovery on HIV integrase inhibitors).

Many proteins of biomedical interest are actually mixtures of glycoproteins, with different levels of glycosylation and glycation, where the mixture proportions are transient for the glycations, and are derived from the blood sample of a patient where numerous interference agents are present. For such samples the assay of the proteins behavior must not only operate at the single molecule level, but must discern subtle modifications quickly given the transient existence of certain glycoforms and other posttranslational modifications. Since roughly half of the glycosylations don't carry negative charge they don't tend enhance acidity to be electrophoretically drawn into the channel, so their direct blockade and recognition at the channel is limited. In these settings an antibody that is known to target the glycosylation of interest could be used to bind that glycosylation (or other post translational modification of interest). Antibodies against the more transient glycations are in use as well, such as with the standard A1c test used by diabetic patients, for example, which involves an antibody binding to the Amadori configuration of glycation, if present, at the N-terminus of hemoglobin A1c. If the antibody is tethered to a DNA-based channel modulator (or a LNA/DNA chimera as descried in the Methods), then a direct means to test for HbA1c glycation could be done (and other glycation products properly excluded from skewing the analysis for an improved HbA1c test, among other things).

A neutral glycation at the N-terminus of a protein will not tend to be favored for direct channel capture/modulation, as mentioned, but a negatively charged glycation (pH>pI) at the C-terminus of a protein is potentially very easily captured at the nanopore for direct assaying. This is found for antibodies, particularly IgG antibodies whose glycosylated Fc region performs a critical receptor binding function when activating the immune system complement cascade. In previous work it has been observed that many antibodies directly exhibit modulatory channel blockades, and upon introduction of their antigen, their bound-state is directly transduced as a notably different channel modulation. Determining the glycosylation profile of antibodies, and Fc glycosylation in particular, is critical to understanding antibody efficacy and blood circulation half-life, so the nanopore platform and the same signal processing methods for understanding NTD transducers can be directly applied to profiling antibody glycosylation blockade signals where the antibody is treated as an NTD transducer in and of itself. Direct antibody profiling would likely only work for part of the glycosylation (or glycation) profile, however, since the Fab N-terminus neutral glycosylation and glycations would probably still need to be assayed by use of antibody intermediates as with the HbA1c test.

Most of the prior work with NTD-based studies has focused on DNA-DNA interactions, DNA-protein binding, individual DNA conformational behavior, and individual protein direct-interaction profiles. The only examples of the more complex protein-protein binding analysis involve antibody binding to a protein, such as in studies of antibody to GFP. Embodiments disclose how stable transducers have been identified and tested, and demonstrates how to do the critical transducer engineering for the general protein structure-function analysis with readily available, inexpensive (commoditized), biomolecular components.

Isoform-Specific Trace-Level Biosensing Using a Nanopore Transduction Detector and a Process for Engineering Inexpensive Biosensing, Diagnostic, and Therapeutic Transducer Molecules The nanopore transduction detection (NTD) system, deployed as a biosensor platform in accordance to embodiments possess highly beneficial characteristics from multiple technologies: the specificity of antibody or aptamer binding, the sensitivity of an engineered channel modulator to specific environmental change, and the robustness of the electrophoresis platform in handling biological samples. A critical component in this system is the NTD transducer. A NTD transducer is typically a compound molecule that serves to transduce the conformational or binding state of a molecule of interest into different channel current modulations. A NTD transducer can often be constructed by simply tethering a molecule of interest to a nanopore channel modulator. In known solutions, using inexpensive (commoditized) biomolecular components, such as DNA hairpins as channel-modulators and antibodies as specific binding moieties (with inexpensive immuno-PCR linkages to DNA) experiments were done to analyze individual antibodies and DNA molecules, their conformations, glycosylations, and their binding properties. It was found that in many applications the DNA-based transducers worked well, but in efforts to extend the methodology to biosensing and glycosylation profiling the DNA modulators often had too short a lifetime until melting. To make matters worse, the DNA-based modulators often had internal conformational freedom of their own that complicated analysis of any linked molecule's conformational changes. Worst of all, sometimes the DNA modulators only modulated when unbound (and the NTD method works best with clearly different modulatory states). Efforts to fix the non-modulatory aspect were partly solved by using a laser-tweezer apparatus to drive distinctive stochastic modulatory blockades in the DNA modulator. This was accomplished by introducing a periodic laser-tweezer 'tugging' on channel-modulator variants that had biotinylated portions that were bound to a streptavidin-coated magnetic bead (another commoditized component). With modulations 'reawakened', however, the number of types of blockade signal seemed to proliferate, and it wasn't clear if an automated signal analysis could be implemented.

Recent discoveries have clarified the new laser-tweezer induced modulator motions as being duplex DNA twist-dominated toggling (in addition to the previously observed conformation-dominated toggling), thus limited in number and manageable (computationally) as is, if necessary. Embodiments provide a straightforward, generally-applicable, method for transducer construction with twist-mode dominated state tracking for large charge/mass biomolecules and their binding targets, with long-tether constructions, and configuration-switching dominated state tracking for small charge/mass biomolecules and their binding targets, with short-linkage constructions. General applications of the NTD method is described for trace-level biosensing, assaying on isoforms, direct assaying on glycoforms, diagnostic development, and therapeutic development and testing. Specific application are discussed in three main areas: (1) air-quality and water-quality testing; (2) binding on large molecular features, large cell-surface features, and heavy metal chelation binding; and related design of diagnostic/therapeutic transducers with both aptamer and antibody components, where the Ab targets to the tissue or tumor of interest, and the aptamer is a tissue directed drug; and (3) single-molecule sequential assaying on isoforms and approximately mass equivalent molecular variants (such as for the cannabinoid family of compounds)

It is known how various molecular strain conditions can lead to isoform splitting on the channel-modulatory molecule often used in transducer designs. For the case of high levels of chaotrope a clearly identifiable isoform splitting could be seen for the DNA hairpin molecules that were often used as distinctive nanopore blockade modulators. This result not only established further evidence of the ability to resolve isoforms on the nanopore detector, but due to the special channel modulation role of the DNA hairpins examined, this result also clarified the nature of some of the complex channel blockade classes encountered under other strain conditions. The new, less-stable, channel modulations appear to be due to DNA hairpin conformations with variable loop/stem twist. The modulator's isoform 'twist' states typically have one isoform present under low-strain conditions and multiple, possibly highly variable conformations, when the molecule is under significant stress, whether due to a high applied potential, higher chaotrope concentration, higher pH, or large charge/mass torque when binding larger target molecules. The solution to the channel modulators having too short a melting time, and too much internal conformational freedom, turns out to be the same, to use locked nucleic acid (LNA) nucleosides. Chimeric LNA/DNA-based transducers and modulators are disclosed, along with further results on inducing a modulatory blockade by using a laser-tweezer. By establishing a general procedure for NTD transducer design a number of biosensing applications are accomplished with embodiments.

Aptamers are nucleic acids with high specificity and high affinity for a target molecule, the properties found to be so useful in monoclonal antibody (mAb) diagnostics and biosensing applications. Aptamer selection is done by a rapid artificial evolutionary process known as SELEX. Nanopore-directed (NADIR) SELEX offers a means to accelerate the SELEX process and arrive at improved outcome, where the standard aptamer sequence library has the constraint that a portion of the sequence self-assemble (anneal) such that it provides an interface with a nanopore detector to provide a modulatory blockade and thereby introduce a 'stochastic carrier wave' into the design/detection process. Subject to this constraint the bifunctional aptamer construct already satisfies the criteria to be a nanopore transduction reporter or (event 'transducer') as shown in FIGS. 6-8. If the transducer has a magnetic bead attachment 'arm', then a trifunctional molecule is being used, thus the Y-shaped DNA molecule disclosed herein. Aptamer design can be quite complicated in some settings, however, such as when the binding target of interest involves large molecular features (for some air or water pollutants), large cell-surface features, heavy metal chelation binding, or because the aptamer transducer is inherently more complex with multiple binding moieties or functionalities, such as with linked double-aptamer constructs and dual aptamer/antibody binding moieties. For the tissue-targeted antibody/aptamer quadfunctional transducer arrangements a 4-way, Holliday-junction, type of DNA molecule could be used, or a linkage via more complicated EDC linker technology. The NADIR augmented SELEX procedure is even more advantageous in such settings.

Therefore, embodiments use LNA/DNA chimeric three-way Y-transducers and four-way Holliday junction transducers, all locked with LNA's to the extent necessary to evoke the desired twist-toggling or config-toggling modulations. The more complex aptamer transducers are particularly relevant when considering therapeutic use of aptamer methods. Aptamer-based therapeutics have begun to get FDA approval in two settings: (1) dialysis therapy where aptamer-based filters are used to clean a patient's blood of accumulated kidney or liver toxins that are not being cleared due to damage to those organs; and (2) tissue or tumor directed treatments where the aptamer is linked to an antibody (encompassed by the aforementioned quadfunctional case) already known to target and localize to the tissue or tumor of interest.

In assaying applications, embodiments of the nanopore detector offers two types of analysis: (1) direct glycoform assaying according to blockade modulation produced directly by the analyte interacting with the nanopore detector, which works on negatively charged glycosylation and glycation profiling best and so is often a partial assaying method; and (2) indirect isoform assaying by means of surface feature measurements using a specifically binding intermediary, such as with the antibody used in HbA1c testing. A mixture of the direct and indirect assaying methods may be necessary for complex problems of interest.

One of the most challenging nanopore assaying applications is for discriminating between isoforms or approximately mass equivalent molecular variants, such as with the over one hundred different cannabinoids that have been isolated from *Cannabis*. The therapeutic benefits of the different cannabinoids is only beginning to be understood. Part of the problem is that different *Cannabis* plants can have very different cannabinoid profiles. Quantitative analysis of a *Cannabis* plant's cannabinoid profile has mainly been done by gas chromatography combined with mass spectrometry. Inexpensive and systematic profiling of *Cannabis* plants is still in its infancy. A variety of monoclonal antibodies and aptamers have been developed with binding to THC (the psycho-active cannabinoid), with varying degrees of specificity to differentiate from the other cannabinoids. Little has been developed, however, to assay the specific presence and amounts of the other hundred or so cannabinoids. What is needed, then, for inexpensive assaying of *Cannabis* profiles is not only the ability to specifically bind a particular cannabinoid with high affinity, but a means to multiplex profile a mixture of cannabinoids with high accuracy. This is achieved by embodiments of the invention due to the state-tracking and individual event counting that is done by the NTD.

High-Specificity Trace-Level Air-Quality and Water-Quality Testing Using a Nanopore Transduction Detector The need for air-quality and water-quality testing for particular pollutants and allergens is growing rapidly due to the increased presence of new types of highly reactive pollutants in many urban settings, increased chemical spraying in general, and due to changing weather patterns and the resulting change in associated allergen (pollen and mold spore) density patterns. Ascertaining with high specificity whether there are dangerous levels of trace pollutants and allergens is typically not done onsite in the field, however, with standard environmental testing methods. Individuals with sensitivities to specific airborne particulates, in particular, are becoming more and more burdened with exposures that are detrimental to their health, with their only recourse being reactive, not proactive: they get sick, then refrain from going outside of highly air-filtered spaces until they feel better (and then repeat the process). What is needed is a method for specific molecular and particulate air-quality and water-quality testing to the field setting, with real-time testing results, to provide critical and timely environmental information.

Nanopore-based detection devices have begun to be deployed for DNA sequence profiling that are remarkably compact, the size of a stapler, and can directly interface to a laptop computer by way of a USB connection. At the same time, smartphones are becoming as computationally powerful as many laptops. This suggests the possibility of using a smartphone linked via a standard mini-USB connection to a nanopore-based environmental tester. Embodiments can take advantage of the wide range of specifically-binding monoclonal antibody and aptamer biomolecular tools to arrive at a specific molecular tester.

NADIR-Optimized Aptamer, Aptamer-Antibody, and Double-Aptamer Engineering and Selection for Biosensing, Diagnostics, and Therapeutics Using a Nanopore Transduction Detector Aptamer-based therapies have been suggested for almost three decades but are only now beginning to see acceptance and rapid development. Aptamers have the high specificity and high affinity found to be so useful in monoclonal antibody (mAb) diagnostic and biosensing applications, but are much easier to store and manage. Aptamers often adopt at their core 3-D conformations that make use of G-quadruplex arrangements that stack in at least two or three layers. Knowing much of the aptamer core sequence structure allows expedited SELEX aptamer selection on variable sequence domains (that provide high specificity akin to the variable regions in mAb's). There is still difficulty in refining the aptamer selection process for desired specificity and affinity, however, for which the NADIR augmented SELEX procedure has been suggested using a nanopore transduction detector, which has recently been extended to operation in a broad range of buffer conditions. The nanopore transduction method, together with the high electrophoretic separability of nucleic-acid based transducers, allows for highly sensitive detection events. High specificity together with high sensitivity is the hallmark of exceptional detection or pattern recognition processes.

Therapeutic use of aptamer methods have begun to get FDA approval in two settings: (1) dialysis therapy where aptamer-based filters are used to clean a patient's blood of accumulated kidney or liver toxins that are not being cleared due to damage to those organs; and (2) tissue or tumor directed treatments where the aptamer is linked to an antibody already known to target and localize to the tissue or tumor of interest. For the latter, the aptamer linked to antibody complex must survive degradation by the body's nucleic-acid degrading defenses, to which end xeno-nucleic acid aptamers have been introduced to defeat the enzymatic degradation defenses. Once blood-based interference agents and degradation mechanisms are taken into account, the demands on the standard aptamer and xeno-nucleic selection process via SELEX begins to be overwhelmed, and the need for NADIR selection augmentation is even more pronounced.

Cannabinoid Assaying by Use of a Nanopore Transduction Detector

Over a hundred different cannabinoids have been isolated from *Cannabis*. Cannabinoids are a diverse class of chemical compounds that bind the cannabinoid receptors in cells in the brain. Cannabinoid receptors have been found in mammals, birds, fish, and reptiles. Two types of cannabinoid receptors are known to exist (CB1 and CB2) and more are thought to exist. Cannabinoid receptors are the most abundant type of GPCRs in the human brain. Different *Cannabis* plants can have very different cannabinoid profiles. Quantitative analysis of a *Cannabis* plants cannabinoid profile has mainly been done by gas chromatography combined with mass spectrometry, although immunoassays are beginning to be employed. Inexpensive and systematic profiling of *Can-*

*nabis* plants is still in its infancy. The inexpensive method disclosed herein for cannabinoid profiling is nanopore transduction detection, where the aptamer or monoclonal antibody selected for the specific binding of interest is linked to a NTD transducer for direct quantification on the relative abundances of the different cannabinoids.

Cannabinoids are grouped into nine main types: cannabigerols (CBG); cannabichromenes (CBC); cannabidiols (CBD); tetrahydrocannabinols (THC); cannabinol (CBN); cannabinodiol (CBDL); cannabicyclol (CBL); cannabielsoin (CBE); and cannabitriol (CBT). CBD is non-psychotropic, mainly has anti-inflammatory therapeutic uses, and counteracts THC as an indirect antagonist. THC is the main psychotropic component and is the only component for which extensive testing has been developed. The THC tests often capture some amount of the other groups in their assays, so are often inadequate for more detailed analysis of the different cannabinoids present. Much of the medicinal use of cannabinoids has been unexplored due to a lack of systemic cannabinoid profiling.

Most cannabinoids are 21-carbon compounds (0.314 kDa) with slightly different ring structures, so specifically quantifying the nine main types of cannabinoids is a challenging problem. Aptamers can easily tell the difference between caffeine (0.194 kDa) and theophylline (0.180 kDa), however, molecules that differ by a single methyl group. Antibodies, for example, can tell the difference between glucose in the Schiff base configuration and Amadori configuration, where the DCA2000 immunoassay involves antibodies that target only hemoglobins that are modified on $\beta$Val1 by glucose in an Amadori configuration (i.e., the molecule defined as HbA1c by the IFCC). What is needed, moreover, for inexpensive assaying of *Cannabis* profiles is not only the ability to specifically bind a particular cannabinoid with high affinity, but a means to multiplex profile a mixture of cannabinoids with high accuracy. Embodiments disclosed herein solve these needs using nanopore transduction detection, where the aptamer or monoclonal antibody selected for the specific regional binding feature of interest is linked to an NTD transducer for direct quantification on the relative abundances of the different cannabinoids.

Embodiments also assay other *Cannabis* components, including biomolecules that are synergistic, such as terpenes and terpenoids, as well as biologically-based contaminants, such as mold, as well as the detection of common pesticides. In practice an on-off detection can be sufficient, in which case a direct antibody nanopore assaying can be done, where a monoclonal antibody (mAb) with antigen the on-off detection desired, is used. The mAb is partly drawn into the detector to give a modulatory signal, and that signal is different according to whether it has antigen bound. This information is used to identify the presence of a molecule, and via sample of bound vs unbound instances, can also determine the concentration of the molecule of interest. This can be done with a single mAb on-off binding history tracking in some cases, or possibly multi-blockade event but filtered to only on-binding events (and associated channel modulation change by the partly-held mAb).

The profiling of the separate mixture components, and profiling on the multi-valent channel interactions of the components, is coupled in the case of the 'direct mAb' profiling, unless specialized glycosylation/modified mAbs are used to have a single channel capture mode for the mAb. The profiling whether coupled or not, complete or not, can still be significantly unique that it has utility, such as it might be strongly associated with disease-state or not, for diagnostic purposes.

The signal analysis and profiling methods can be used in other applications, not just the NTD. Consider a visual analysis of air or water quality application. Similar to NTD in one aspect is the idea to couple unique information/signal on the molecule of interest into an electronic signal. Consider having the fluid (air or water) drawn through a pipe to achieve a particular flow-rate, and to have a coherent light source (a laser) or a partly coherent source (LEDs) providing illumination on the flow through a window in the side of the pipe. Measurements of backscatter, or forward scatter with a second window on the other side of the pipe, can be done with a CCD array arranged for detection. If the pipe is a clear glass tube, then windowing issues are eliminated, but can't go to high pressurization, so whatever works best in the application of interest. Similar to NTD in another aspect is the air or water assay is not just coupling events into electrical signals in the moment, but in a sequence of observations, providing a flow of information relating to coupling coherent light scattering properties of molecules and particulates into electrical signal impulses via a CCD array. So similar to NTD we now have the same signal processing architecture and machine learning adaptability to analysis of air/water quality by way of stationary signal profiles that are classified according to state—in this application according to a mixture analysis on the type and amount of contaminant present.

The coupling of state to information in the laser-scanner described above, for air and water quality assaying, was given in terms of laser scintillation. There are other molecule specific couplings that could be achieved by other settings, including buffer changes, such as addition of PEG and urea. A specialized buffer component might be the introduction of NTD-transducers with a fourth arm that has a laser-dye attachment, e.g., NTD 'Holliday" (4-arm) DNA transducers with laser-dye attachment arms, characterized/validated in the NTD setting for binding, then used in 'bulk mode' assaying according to dye response under the laser scintillation approach above. Similar arrangement with use of very small magnetic beads instead of dye attachments (in a laser-tweezer illumination gradient configuration) could also be employed with transducers drawn differentially according to bound vs unbound state for differential reading, possibly laser scintillation in a separate stage like above, or by direct NTD method, to characterize the presence and amount of a molecule or particulate of interest.

Rapid Viral Testing Using a Nanopore Transduction Detector

The explosive geographic expansion of the Zika virus provides another reminder that rapid diagnostic tools for new viral infections is an ever increasing need. The rapid deployment of a fast diagnostic tool in the example of the Zika virus is all the more pertinent given that the virus has been shown to be the cause of microcephaly in the fetuses of exposed pregnant women, along with results indicating possible brain damage (Epstein-Barre reaction) to a significant fraction of those exposed. A rapid development, deployment, and evaluation of a Zika virus diagnostic would afford the patient the critical time needed to undergo aggressive prophylactic measures. Similarly, certain fungal infections need to be diagnosed as early as possible. The treatments for many fungal infections are highly toxic, causing serious damage, such that they will only be undertaken if infection is confirmed. Unfortunately, by the time many brain-invasive fungi are cultured, a patient with suspected exposure has advanced beyond where treatment can be made (the infection is then lethal), such as for *Cryptococcus neoformans* infection which can disrupt and cross the blood-brain barrier. Genomes on fungal and bacterial pathogens can be done in a less than a day, viruses a fraction of a day. Pathogens that are suspected can be probed in a matter of hours using an NTD platform with the methods described here using probes designed according to their genomic profile. Unknown pathogens would first need to either have their genomes sequenced (less than a day) if sufficient DNA already available, or a sample directly measured via a test assay template (same procedure as for biomarker discovery) for assay-level fingerprint determination, then testing for that fingerprint in the patient.

Targeted DNA annealing tests can be performed using a nanopore transduction detector (NTD) using the methods described in what follows. In other words, the NTD platform and modern DNA sequencing and purification methods allow for a programmable 'nanoblot' for specific nucleic acid sequence probing, where use is made of a DNA-annealing reporter molecule that is engineered, via a simple design process akin to probe designs for use in nucleic acid microarrays, to transduce strongly matched, and annealed, segments of the virus (or other) genome to associated channel-current blockade events.

Embodiments provide a rapid annealing-based detection platform due to a recently established ability to operate under high chaotropic conditions (5M urea), which allows measurement of collective binding interactions such as nucleic acid annealing with other simpler binding and related complexes thereby eliminated and effectively filtered from the analysis task. Examples aptamer and antibody based NTD transducers are shown in FIGS. 6 and 7, where the idea is to work with a set of nucleic acids with commoditized attachments and specifications, and have them come together spontaneously to assemble into a strongly bound complex (where there is one dominant complex assembly) that has the desired multi-functionality. Initially Y-transducers were used that were designed that had the Y-branching and the stem length such that the Y-transducers terminal base-pair was perched directly over the limiting aperture of the channel during capture. One arm of the Y had a loop to simply prevent it being captured, when only stem oriented captures were desired. The other arm of the Y then had the binding moiety. In the case of DNA annealing this could be an overhang or as internal single-stranded nucleic acid sequence as in test molecules shown in FIG. 8.

When working with longer DNA captures on linear segments the duplex end is observed to mainly reside in one, fixed, blockade configuration, probably due to the electrophoretic force strongly drawing the larger nucleoside into the channel. Initially having a fixed blockade wasn't a problem with the Y-shaped transducers, especially for the unbound case, but became a possibility when bound if the bound object was 'large' or a significant length of nucleic acid, or when working with a commoditized linkage by annealing to an immuno-PCR tagged antibody or other protein. When working with longer DNA hairpins with large mass/charge attachments sometimes the opposite occurred, the large bound extension appeared to induce occasional toggling where none was observed before (such as seen in streptavidin-coated bead binding to biotinylated 20 bphp hairpins described in the Results). In order to have a controlled way to have a simple nucleic acid based transducer, it was then attempted to recover unique modulatory blockade signaling by linking to a magnetic bead where laser-tweezer 'tugging' could then be used for injection of kinetic energy at the single molecule level. Initial results were successful, allowing for simple inexpensive probe design, but it was unclear if the stochastic carrier wave signal processing on the more complex transducer modulation signal would be possible given the proliferation in blockade modes observed under laser-tweezer modulation. In more recent studies with chaotropes, the isoforms of the DNA hairpin modulators is better understood, indicating that there are two mode types of modulation in captured duplex nucleic acid: position/orientation and twist/stretch, where the new signal complication is due to the appearance of the twist/stretch modes.

Nanopore-captured DNA hairpin modulators can exhibit not only spatial/orientation toggling but also torsional/twisting toggling when sufficiently excited. This effect becomes most notable when channel modulations are induced by laser-tweezer pulsing, but has been observed in other high-strain conditions for captured DNA hairpin channel modulators, such as high chaotrope, high pH, high applied voltage, and high mass/charge capture events. The new understanding of the laser-tweezer induced modulations suggests a limit for the induced modulator's signal classes to those already seen and a manageable signal analysis platform can thereby be implemented. In practice a stochastic channel modulator that produces the simplest, non-fixed-level, stationary signal blockade is desired, such that the stochastic carrier wave (SCW) signal processing methods can be employed. The position and twist toggle modes in the modulator together pose a more complex SCW system, but can be managed with sufficient sample observations on modulator during its different states (such as linked to bound or unbound analyte).

A related complication with using DNA-based channel modulators has been their short lifetimes until melting. This problem has been eliminated in embodiments by use of locked nucleic acid nucleosides (LNAs). LNAs serve to reduce twist modes by locking the nucleic acid and thereby restricting its internal degrees of freedom in term of twist/stretch. This can be a good thing in that it will simplify the SCW signal training mentioned above. A simpler SCW analysis is not critical, however, so the main optimization to be accomplished by 'locking up' the modulator with increased LNA is effectively a tuning over molecular variants with greater or lesser twist mode event transmission. For annealing-based detection this is a big deal since the properly annealed nucleic acid duplex will transmit twist mode excitations notably differently than improperly annealed DNA (if even present). For this reason some modulator arrangements with laser-tweezer pulsing may have their bead attachment on the same arm as the annealing binding site (further details to follow), and have a low number of LNA bases in the LNA/DNA chimeras in the binding template (keeping blunt terminus and Y-nexus regions strongly LNA based to prevent melting as much as possible, but permitting twisting).

The application of the NTD platform as a programmable nanoblot for pathogenic or trace nucleic acid detection is, thereby, shown to be possible in 'clean' situations. But blood is full of a number of interference agents, so there is clearly the need to demonstrate interference agents can be tolerated at high levels. To this end results are also given to demonstrate the robust operational range of the NTD platform with common blood interference agents at the high level typically used in medical blood test validations. In doing so there is clearly not a problem with maintaining the integrity of the nanopore in the presence of interference agents. There can be a problem in maintaining the integrity of the bilayer with some blood components, however, and that is discussed later.

Once the method is in place for NTD nanoblots for the presence of pathogenic nucleic acid the last remaining 'dial to turn' is on the level of trace detection obtainable. The electrophoretic nature of the NTD platform is a huge advantage in this setting since nucleic acids are one of the lowest pI biomolecular groups. For this reason a size exclusion chromatography method can be used by working with buffers having very high PEG concentration. PEG length over 4000 will generally not intercalate into the channel and PEG may serve to sequester albumin as well as delay its passage compared to nucleic acid. Furthermore, PEG serves to separate the larger nucleic acids (like in size-exclusion chromatography), which suggests use of xeno-LNA transducers not susceptible to nuclease activity (where there is addition of nuclease during one processing stage to eliminate DNA interference by cutting it into small pieces). Results on PEG-filtering will be given. If would appear that direct blood analysis on a NTD with a set of analyte transducers for multiplex assaying is possible. In applications to nucleic acid testing, this provides a means for rapid viral testing.

Experimental Results

Experimental results of embodiments initially use the biotinylated LNA 8 base-pair (8 bp) hairpin transducer. 8 bp transducers have a faster 'toggle' allowing a faster classification and thus 'read-out' of signal events. Then the focus will be on the biotinylated chimeric LNA/DNA 9 base-pair (9 bp) hairpin transducer. The 9 bp transducers have lifetimes transducing events at the channel in excess of an hour, and thus provide a lengthy tracking capability on a single molecule's state. Following the 9 bp LNA transducer results, brief results are given on the laser modulation enhancement to the transducer engineering process. Brief results are then given for operation in the presence of standard cellular and blood serum interference agents. Lastly, results are given on use of PEG as volume exclusion filter.

Biotinylated 8 Base-Pair LNA Hairpin Binding Experiments with Streptavidin (A Streptavidin Biosensor)

The results of the LNA/DNA chimera based NTD transducer/reporter redesign are shown in a series of screen captures of representative blockade events. Automated signal analysis has been demonstrated in prior work with the DNA variants, as shown in FIG. 2.

The biotinylated 8 base-pair DNA hairpin (DNA 8GC-Bt, shown in FIG. 1) has lifetime (until melting and channel translocation event) about 6 s on average, with a wide range of observations from a fraction of a second to 15 s that is dependent on buffer, and temperature, etc. (consistent with early work on DNA hairpin gauges in the nanopore). The biotinylated 8 base-pair LNA/DNA chimeric hairpin (LNA 8GC-Bt), on the other hand, has lifetime 12 minutes on average, ranging from about 3 minutes to over 30 minutes for individual melting times. Similarly, 9 base-pair DNA hairpins have lifetimes going from about one minute with individual lifetimes from 2 s to 120 s. Compare this with LNA 9GC-Bt lifetimes that are typically greater than 60 minutes, even in 2M urea.

Figure 31:
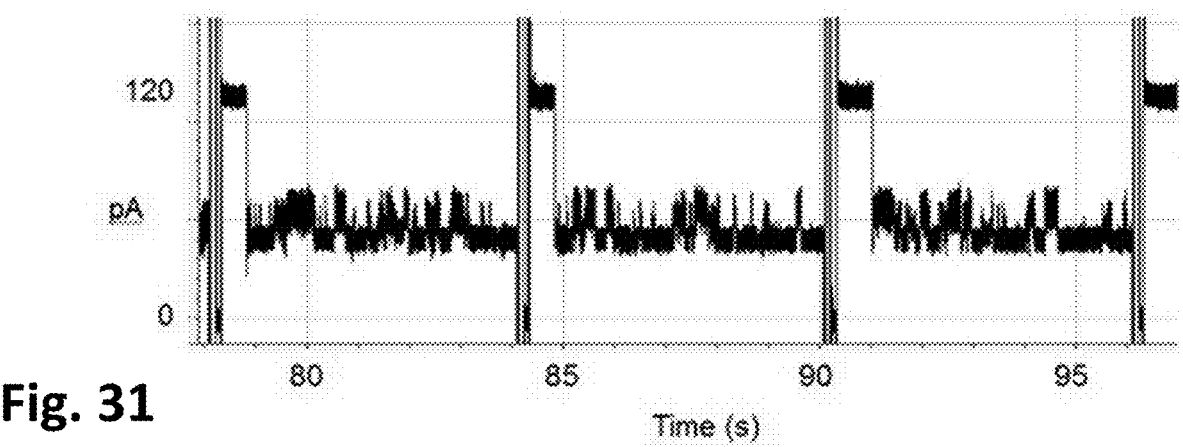
FIG. 31 illustrates LNA 8GC-Bt blockade signals, 5 s blockade before auto-eject.

FIG. 31 illustrates LNA 8GC-Bt blockade signals, 5 s blockade before auto-eject (shown as the vertical current reset pulses that occur during the polarity reversal). Very little open channel (less than 1 s at 120 pA) occurs before the next capture event. The concentration of LNA in the detector well is 2 uM. Concentration of 12 nM in the detector well produces similar blockades, but with significantly greater (~200 s) open channel time between blockade events. In FIG. 31 the nanopore detector software is set to only capture the first 5 s of a blockade trace, then perform a polarity reversal to eject the captured analyte and proceed with a new capture.

Figure 32:
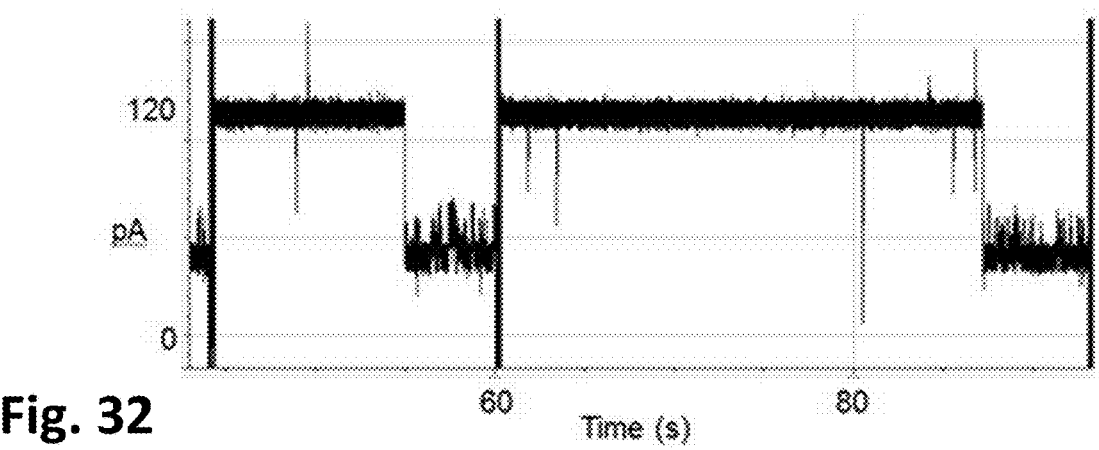
FIG. 32 illustrates LNA 8GC-Bt blockade signals in the presence of streptavidin during the first 10 minutes after introduction of streptavidin.

FIG. 32 illustrates LNA 8GC-Bt blockade signals in the presence of streptavidin during the first 10 minutes after introduction of streptavidin. LNA and streptavidin are in a 1:1 ratio, with both at 2 uM concentration in the detector well. The timescale is longer, but the hold time for the hairpin blockades is still held at 5 s when comparing to FIG. 31. The result shown is typical for the first 10 minutes after introduction of streptavidin. Note the much longer intervals of open channel even though the LNA concentration hasn't changed. This is due to the streptavidin binding some of the LNA and sequestering it in solution, leaving effectively lower concentration of LNA free to report to the channel detector. The signals produced will continue to change as more LNA is sequestered, and eventually bound streptavidin is pulled to the nanopore detector (to 'report'). Unbound streptavidin is almost never seen to interact with the channel. Streptavidin has pI 7-8, so this was initially thought to be due to it having a possibly positive charge in the pH 8 of the standard experimental buffer setting, but in studies at pH 9 there is still no streptavidin blockade signal even in mM concentrations. Basically, most proteins, even if very negatively charged at pH 8, such as albumin with pI 4.7, will not interact with the channel. Certain proteins are found to strongly interact, however, such as some classes of antibodies (even with pI 8.5 in pH8 buffer).

Figure 33:
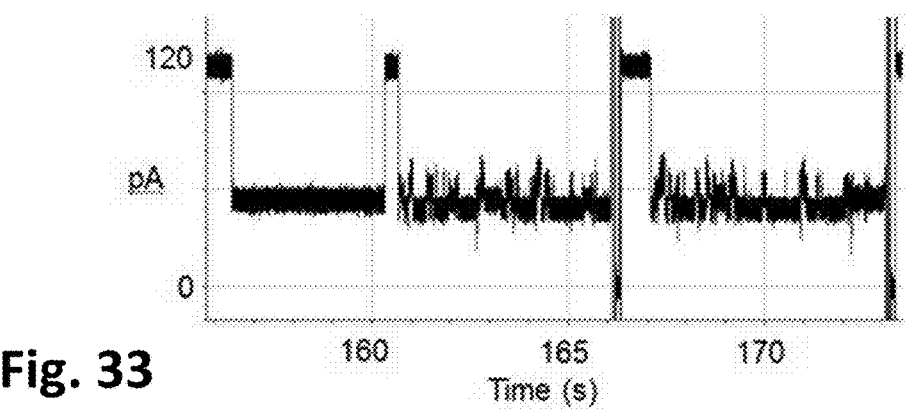
FIG. 33 illustrates LNA 8GC-Bt blockade signals in the presence of streptavidin during the second 10 minutes after introduction of streptavidin.
Figure 34:
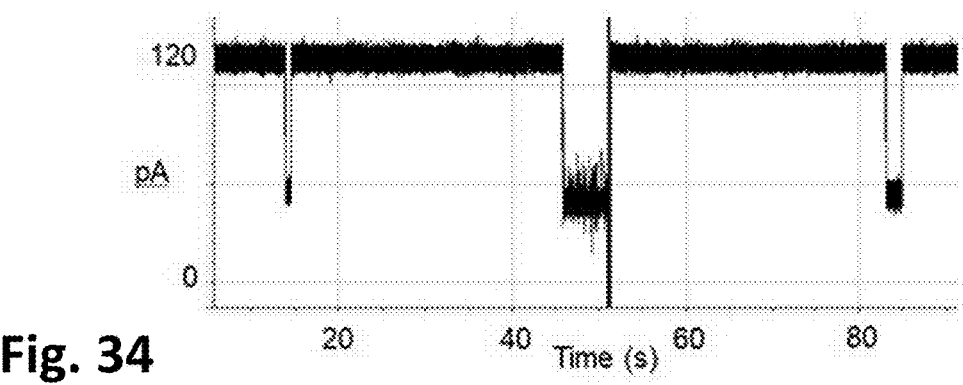
FIG. 34 illustrates LNA 8GC-Bt blockade signals in the presence of 1:1 streptavidin after approximately 30 minutes of reaction time.

FIG. 33 illustrates LNA 8GC-Bt blockade signals in the presence of streptavidin during the second 10 minutes after introduction of streptavidin. A bound reporter signal is shown as the leftmost blockade event. A new class of blockade begins to be seen. The new class does not 'toggle' and is never seen (in runs with over 2000 LNA 8GC-Bt blockades) if streptavidin has not been added. FIG. 34 illustrates LNA 8GC-Bt blockade signals in the presence of 1:1 streptavidin after approximately 30 minutes of reaction time. The central blockade is an unbound reporter signal, the much shorter left and right blockades are bound reporter blockades. After another 10 minutes has passed (30 minutes since the introduction of streptavidin) the free LNA sequestration is nearly complete (even though 1:1 streptavidin can bind up to 4 biotins).

Figure 35:
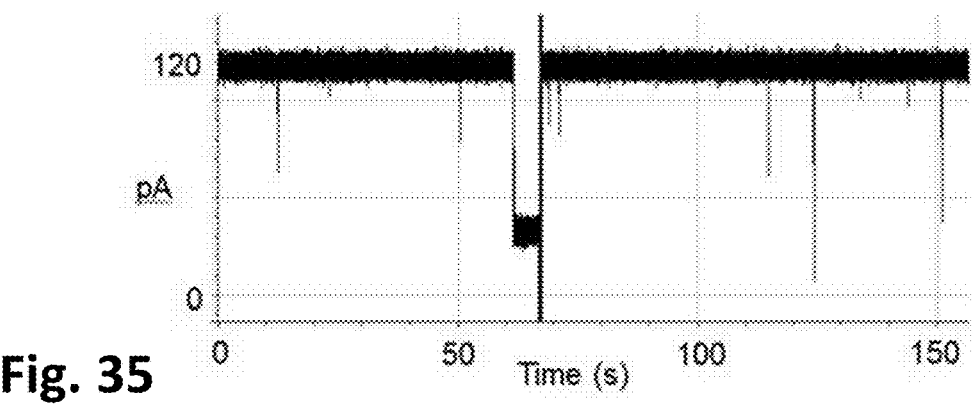
FIG. 35 illustrates streptavidin bound LNA 8GC-Bt blockade signals after approximately 40 minutes of reaction time.

FIG. 34 illustrates LNA 8GC-Bt blockade signals in the presence of 1:1 streptavidin after approximately 30 minutes of reaction time. The central blockade is an unbound reporter signal, the much shorter left and right blockades are bound reporter blockades. FIG. 34 shows one free LNA blockade (in middle), and two bound LNA blockades (one on either side). FIG. 35 illustrates streptavidin bound LNA 8GC-Bt blockade signals after approximately 40 minutes of reaction time. The free LNA sequestration is complete, free LNA will now be seen only rarely, with bound signal dominating. Bound signal will now often be captured for sufficiently long that it reaches the 5 s auto-eject time. This is likely because the captures will be dominated by streptavidin that is multiply-bound with biotinylated LNAs (providing an even greater pI shift than the singly bound streptavidin, thereby dominating the blockade events seen, and more strongly electrophoretically held at the channel). At later times and at the larger timescales (2.5 minutes shown in FIG. 35) 'melted' ssLNA translocation events are seen as short blockade 'spikes'.

Biotinylated 9 Base-Pair LNA Hairpin Binding Experiments with Streptavidin (pH8)

The results of the LNA based NTD transducer/reporter redesign are shown in a series of screen captures of representative blockade events. The biotinylated 9 base-pair purely DNA hairpin (DNA 9GC-Bt, similar to 8GC-Bt shown in FIG. 1) has lifetime (until melting and channel translocation event) only about one minute, where the range in individual lifetimes 9GC-Bt has a wide spread, from 2 s to 120 s. The chimeric LNA/DNA 9GC-Bt lifetime, on the other hand, is typically greater than 60 minutes, even in 2M urea. The results to follow are first performed at pH 8, but since some proteins of interest have pI's up to 9, and would be driven away from the channel under normal operating conditions, the analysis is repeated for pH9 as well. For the streptavidin biosensor test this is directly relevant since streptavidin has pI 7-8.

Figure 36:
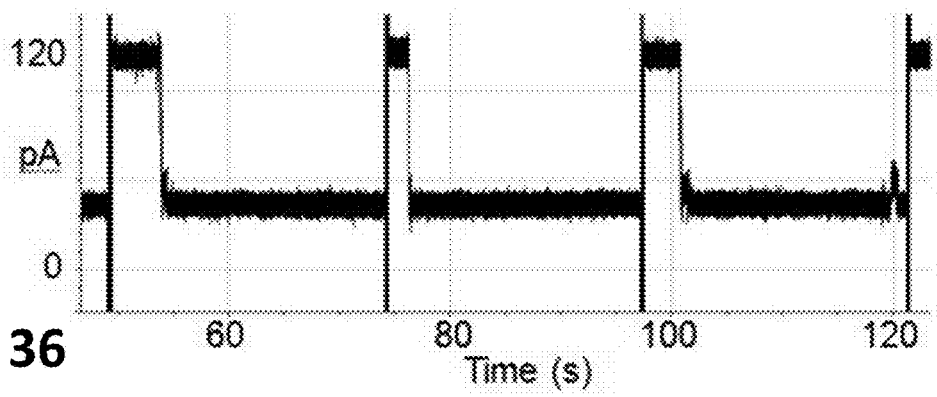
FIG. 36 illustrates LNA 9GC-Bt blockade signals at 2 uM concentration in the detector well (70 uL).

FIG. 36 illustrates LNA 9GC-Bt blockade signals at 2 uM concentration in the detector well (70 uL). Auto-eject time is set at 20 s. The LNA 9GC-Bt blockades have a slower 'toggle' than LNA 8GC-Bt (similar to the DNA-based 9GC-BT and 8GC-Bt). In FIG. 36 the nanopore detector software is set to only capture the first 20 s of a blockade trace then perform a polarity reversal to eject the captured analyte and proceed with a new capture.

Figure 37:
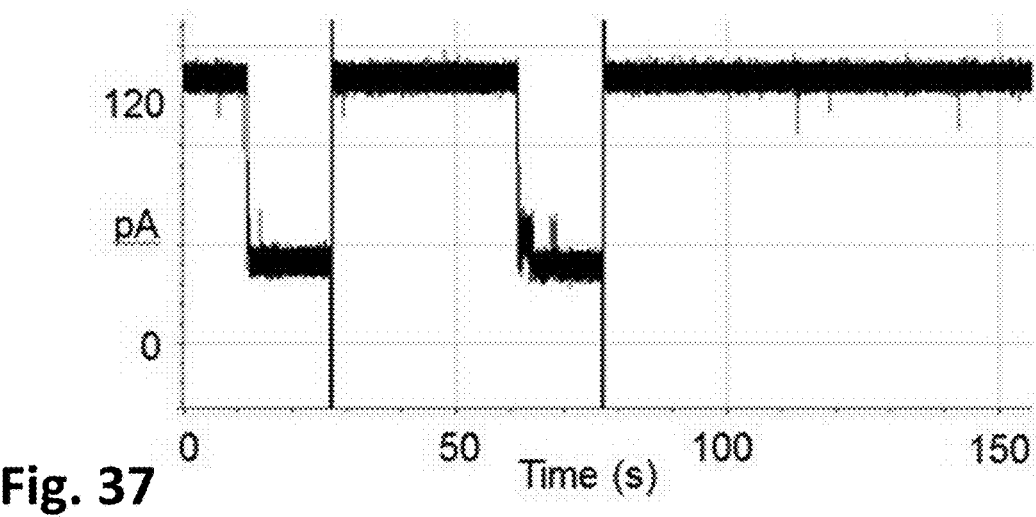
FIG. 37 illustrates LNA 9GC-Bt blockade signals (15 s auto-eject time) in the presence of streptavidin during the first 10 minutes after introduction of streptavidin.

FIG. 37 illustrates LNA 9GC-Bt blockade signals (15 s auto-eject time) in the presence of streptavidin during the first 10 minutes after introduction of streptavidin. LNA and streptavidin are in a 1:1 ratio, with both at 2 uM concentration in the detector well. The initial sequestration effect of the streptavidin is evident as with the original DNA 8GC-Bt experiment. In FIG. 37 streptavidin is added in a 1:1 ratio to the LNA 9GC-Bt already present (e.g., the streptavidin concentration in the detector well is 2 uM). The timescale is longer, and the hold time for the hairpin blockades is now set at 15 s. The result shown is typical for the first 10 minutes after introduction of streptavidin. The blockade signal structure is unaltered from that shown in FIG. 36, it is merely compressed by the larger timescale shown. Note the much longer intervals of open channel even though the LNA concentration hasn't changed. This is due to the streptavidin binding some of the LNA and sequestering it in solution, leaving effectively lower concentration of LNA free to report to the channel detector. The signals produced will continue to change as more LNA is sequestered, and eventually bound streptavidin is pulled to the nanopore detector (to 'report'). Unbound streptavidin is almost never seen to interact with the channel. Streptavidin has pI 7-8, so this was initially thought to be due to it having a possibly positive charge in the pH 8 of the standard experimental buffer setting, but in studies at pH 9 there is still no streptavidin blockade signal (even in mM concentrations). It is found that most proteins, even if very negatively charged at pH 8, such as albumin with pI 4.7, will not interact with the channel. Certain proteins are found to strongly interact, however, such as some classes of antibodies (even with pI 8.5 in pH8 buffer), and this is described further in the Discussion, but new results on antibody Fc glyco-profiling are beyond the scope of this paper so won't be discussed here.

Figure 38:
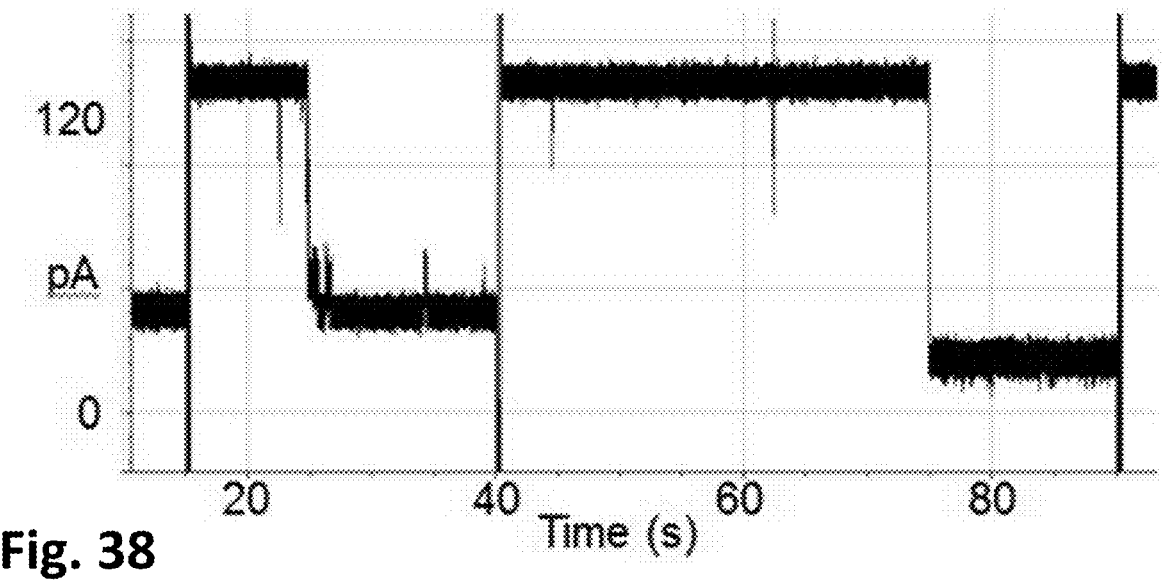
FIG. 38 illustrates LNA 9GC-Bt blockade signals (15 s auto-eject time) in the presence of streptavidin during the second 10 minutes after introduction of streptavidin.

FIG. 38 illustrates LNA 9GC-Bt blockade signals (15 s auto-eject time) in the presence of streptavidin during the second 10 minutes after introduction of streptavidin. A bound, fixed-level, blockade is shown at the right, that is not seen without streptavidin present, and due to the longer-lived 9GC-BT (versus 8GC-Bt), the event lasts the full 15 s until an auto-eject occurs. The new class of blockade does not 'toggle' and is never seen (in runs with over 2000 LNA 9GC-Bt blockades) if streptavidin has not been added.

Figure 39:
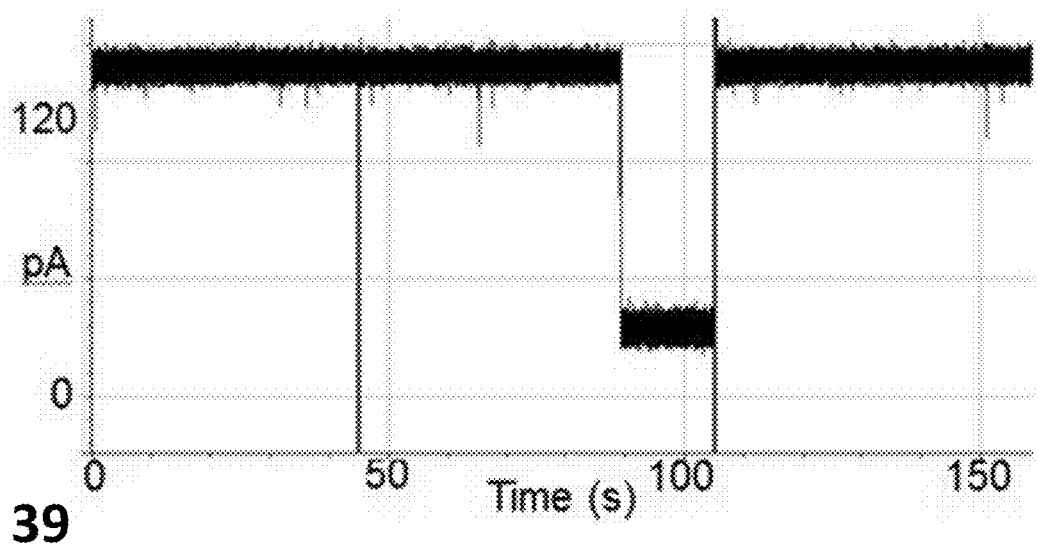
FIG. 39 illustrates streptavidin bound LNA 9GC-Bt blockade signal after about 30 minutes of reaction time.

FIG. 39 illustrates streptavidin bound LNA 9GC-Bt blockade signal after about 30 minutes of reaction time. The baseline shift, and subsequent shift in the bound 9GC-BT's fixed level, is due to the well being open and the well evaporation leading to higher salt concentration, and thus higher currents under the fixed voltage patch clamp operation. In FIG. 39 the free LNA sequestration is nearly complete (even though 1:1 streptavidin can bind up to 4 biotins), and it shows one bound LNA blockade. The free LNA sequestration is complete, free LNA will now be seen only rarely, with bound signal dominating. The captures will also tend to be dominated by streptavidin that is multiply-bound with biotinylated LNAs (providing an even greater pI shift than the singly bound streptavidin, thereby dominating the blockade events seen, and more strongly electrophoretically held at the channel).

Biotinylated 9 Base-Pair LNA Hairpin Binding Experiments with Streptavidin (pH9)

Figure 40:
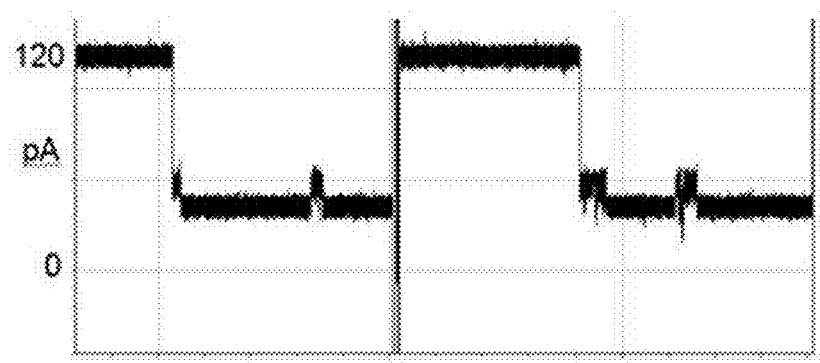
FIG. 40 illustrates LNA 9GC-Bt blockade signals at 500 pM concentration in the detector well at pH9.
Figure 41:
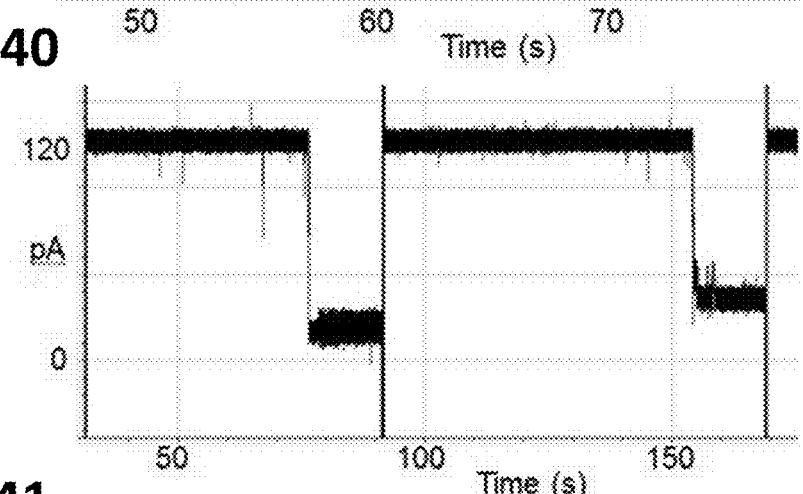
FIG. 41 illustrates typical LNA 9GC-Bt blockade signals are shown for 250pM concentration in the detector well at pH9, with streptavidin added 1:1, after the first 10 min.

The results of the LNA based NTD transducer/reporter redesign are repeated in pH9 buffer and shown here in a series of screen captures of representative blockade events. FIG. 40 illustrates LNA 9GC-Bt blockade signals at 500 pM concentration in the detector well at pH9. Auto-eject time is set at 10 s. The LNA 9GC-Bt blockades have a faster 'toggle' than LNA 9GC-Bt at pH8. FIG. 41 illustrates typical LNA 9GC-Bt blockade signals are shown for 250 pM concentration in the detector well at pH9, with streptavidin added 1:1, after the first 10 min. Auto-eject time is set at 10 s. Bound blockade signals are now seen (the one with the lower blockade level on the left). Unlike the bound LNA 9GC-Bt probe at pH 8, the bound LNA 9GC-Bt blockades at pH9 occasionally have a 'toggle' or switch to a toggle mode (the bound blockade on the left shows a transition to toggle 2 s into the bound blockade). This toggling is more informative about the identity of the molecule causing the blockade and indicates possible inducement to always be in a bound toggle mode under gentle laser-tweezer pulsing (results of this on 20 bp hairpins to be shown following).

Figure 42:
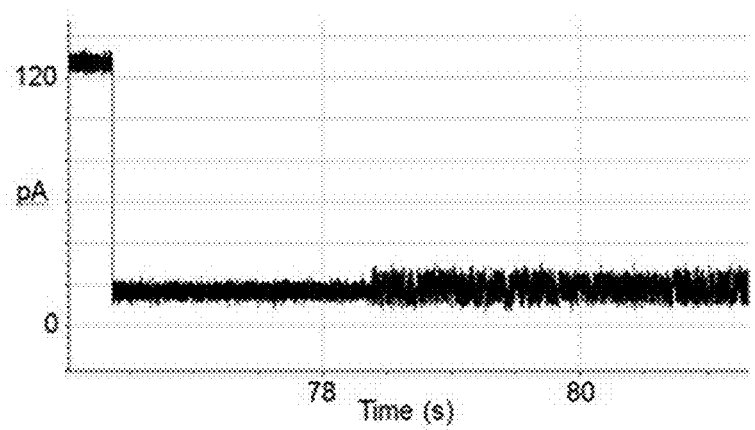
FIGS. 42 and 43 illustrate the streptavidin bound LNA 9GC-Bt channel blockade signal at higher resolution.
Figure 43:
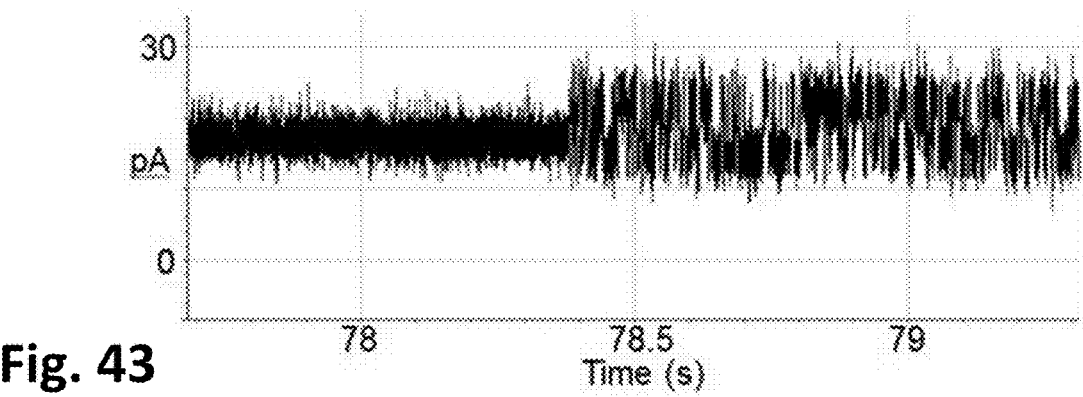

FIGS. 42 and 43 illustrate the streptavidin bound LNA 9GC-Bt channel blockade signal at higher resolution. Biotinylated hairpin binding to streptavidin and antibody complexation is validated using gels, IEF, and CE. The results shown in FIGS. 41-43 demonstrate that a bound 'toggle' signal is occasionally spontaneously possible at pH 9. This shows the ability to induce the 9GC-Bt molecule to produce a more informative toggling blockade, thereby forcing the bound reporter molecule to exhibit a toggle blockade in general (regardless of pH 8 or 9, etc.) by use of magnetic bead attachments driven by a pulsed laser-tweezer apparatus.

Twist Mode

Experiments are done with a biotinylated LNA/DNA chimeric 9 bp hairpin (LNA 9GC-Bt) in pH 9 that has been linked to a streptavidin-coated magnetic bead. LNA 9GC-Bt with streptavidin bound shows a new mode of toggle, shown in FIGS. 40-43). Possible twist mode switching is found for the large mass binding case here as with high pH, high voltage, and under laser-tweezer inducement to follow. In FIG. 43, the molecule appears captured in one twist/configuration, then shift to the other twist may briefly occur, from which a configuration toggling commences. The configuration toggle appears to involve blockade positions favored by neither of the twist conformations. The captured molecular excitations typically start, as it does here, in what is thought to be a DNA-hairpin twist-modulation mode (a direct consequence of conservation of angular momentum and the large mass streptavidin attachment), eventually this settles into a configuration-toggle mode—where one configuration is sufficiently deep that DNA terminus fraying and extending can sometimes be observed.

Laser-Tweezer Induced Transducer Modulation

Figure 44:
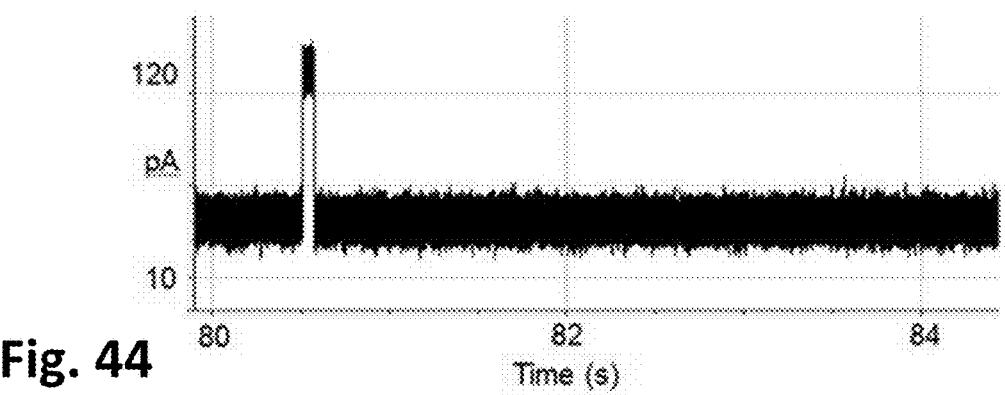
FIG. 44 illustrates a 9GC-ext with Faraday cage in place.

FIG. 44 illustrates a 9GC-ext with Faraday cage in place. The brief upper level is the open channel baseline current level (at 121 pA). The blockade commencing after the baseline lasted for 50 sec, of which the first ~4 s is shown. The 'fixed' blockade level is at 40 pA. The transducer DNA hairpin has stem length twenty base-pairs (20 bp) and loop size 5 dT, with the central thymidine modified with a linker to biotin. The hairpin in this form is referred to as 9GC-ext because it is a 20 bp extension of the biotinylated 9GC control molecule that has a 9 bp stem. The hairpin is then mixed with a solution of magnetic beads that have a streptavidin coating, leading to complexes of magnetic beads attached to a DNA hairpin channel modulator (9GC-ext-mag) by way of a streptavidin-biotin linkage. The mass of the magnetic bead is substantially greater than the hairpin, such that upon capture the likelihood of twist mode being excited is even greater (an even greater angular momentum impulse would occur on capture), even though it is still relatively rare in initially. As the experiment proceeds, however, the twist modulating captures increase in likelihood due to more beads becoming more bound with hairpin and thus more mass and charge, thus greater angular momentum impulse on capture.

Figure 45:
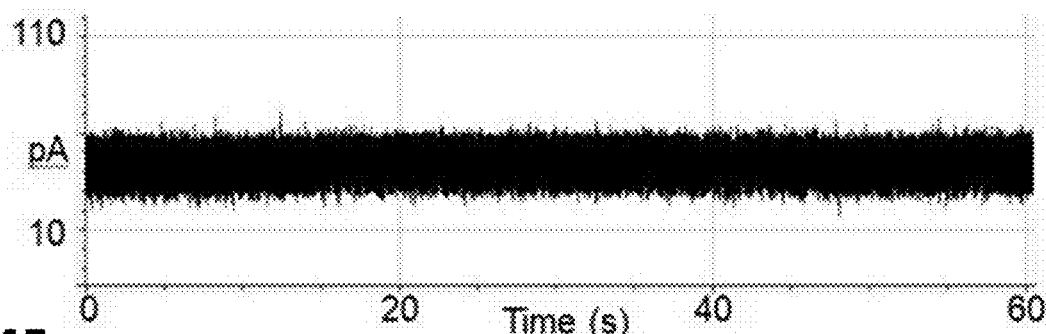
FIG. 45 illustrates a typical 9GC-ext-mag blockade is shown, with a 60 s of blockade trace, where the Faraday cage is not in place and no 60 Hz line noise discernible.

FIG. 45 illustrates a typical 9GC-ext-mag blockade is shown, with a 60 s of blockade trace, where the Faraday cage is not in place and no 60 Hz line noise discernible. The blockade level has shifted slightly higher with the magnetic bead attachment, at 42 pA (slightly higher level and slightly greater noise than the molecule without streptavidin coated bead attaching to the biotinylated 9GC-ext hairpin).

Figure 46:
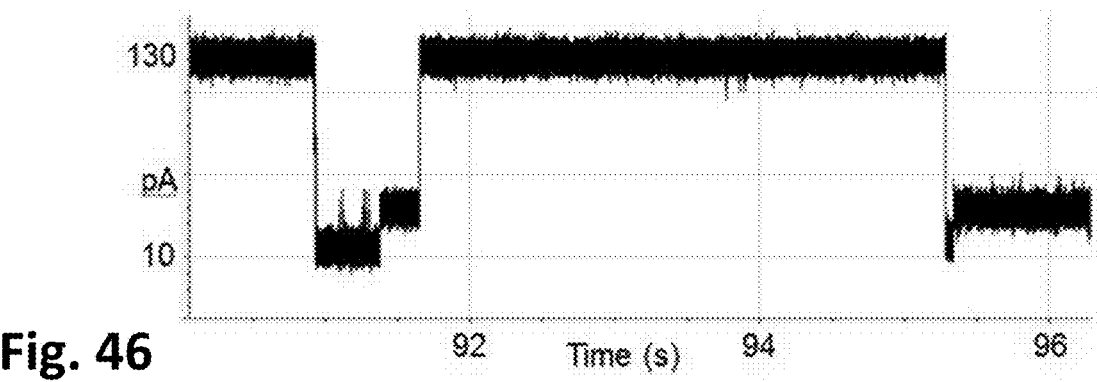
FIG. 46 illustrates a short duration 9GC-ext-mag blockade signal.

FIG. 46 illustrates a short duration 9GC-ext-mag blockade signal (apparently before diffusional escape) with the beginning of another at the far right. The Faraday cage is in-place for this trace, and the 42 pA level is seen as before as the upper level toggle (but is less noisy than before since the cage in place). Two clear levels of blockade can be seen, and are thought to correlate with two distinct molecule-channel blockade configurations as usual. The toggle signals are thought to describe a switching between molecular loop/stem 'twist' states, however, and not between two channel blockade configurations (where the molecule in the same internal conformation).

Laser-tweezer pulsing can induce a transition from a fixed-level to a toggling blockade on biotinylated 20 bp DNA hairpins. It was not clear initially, however, that there was both spatial configuration switching and twist configuration switching, because the latter switching hadn't been seen before. The existence of two loop/stem twist configurations began to become apparent, however, as experiments began to explore a variety of strain conditions, such as high urea (such as 2-5M concentration of chaotrope, see FIG. 10), higher than the 120 mV applied potential (such as 150-180 mV), higher pH (9 or greater), or in the presence of large bound charge/mass objects (e.g., streptavidin, streptavidin-bead, antibody, or large-antigen attachment).

Figure 47:
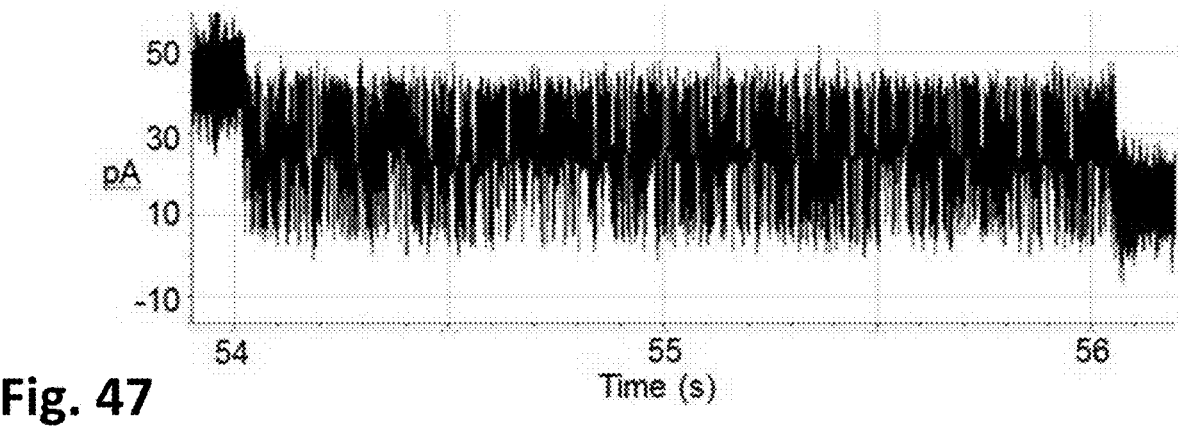
FIG. 47 illustrates a channel blockade due to 9GC-ext-mag in the presence of laser-tweezer pulsing.
Figure 48:
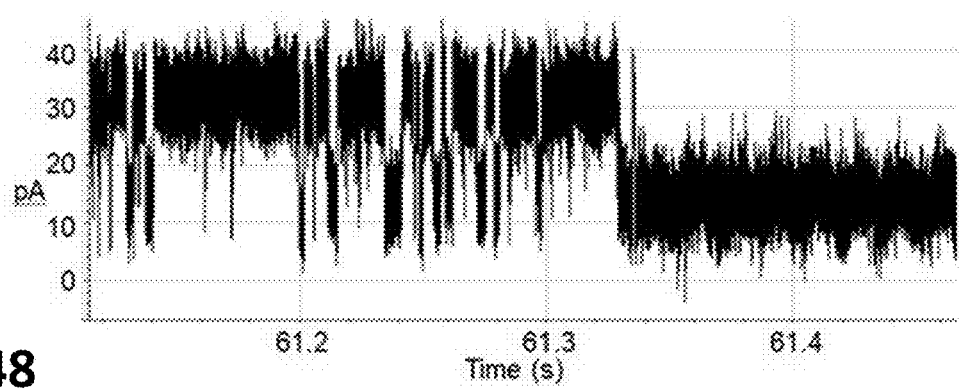
FIG. 48 illustrates an enlarged view of the lower twist state's laser induced toggle as it finally becomes 'stuck' at one level.

FIG. 47 illustrates a channel blockade due to 9GC-ext-mag in the presence of laser-tweezer pulsing (using a chopped laser beam with an off-target edge-illumination intensity gradient). The upper 'twist-level' is briefly seen initially as before (the 42 pA level), followed by a switch to the lower-level twist blockade that has its own, laser-induced, toggle, before sticking at the lower twist state's lower blockade level at the end of the trace (the sticking could be due to the magnetic bead attaching other biotinylated hairpins with increase in charge and overall electrophoretic driving force). FIG. 48 illustrates an enlarged view of the lower twist state's laser induced toggle as it finally becomes 'stuck' at one level. Note the clear 60 Hz line noise evident in the enlarged view. This noise is not present in 9GC-ext-mag blockades without laser illumination (and without cage), so the 60 Hz line noise is being transmitted in the laser beam not via the unshielded surroundings. The laser was found to induce the most notable switching in the lower-level twist state when chopped at 4 Hz.

Figure 49:
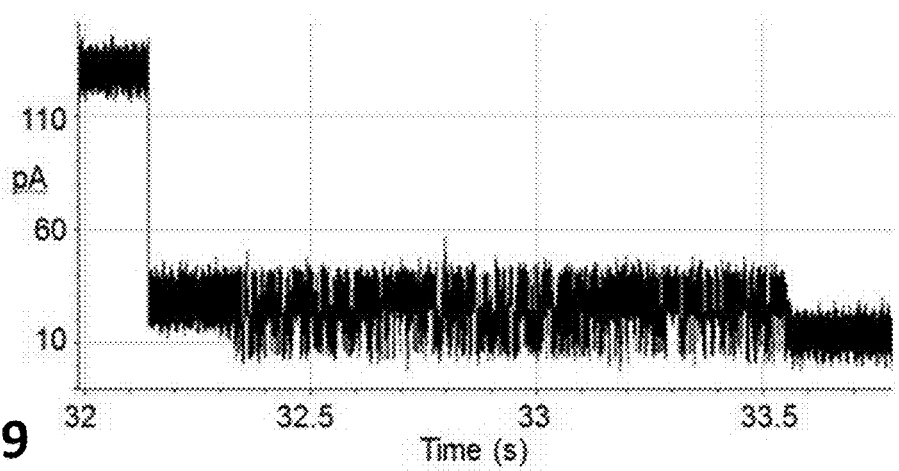
FIG. 49 illustrates another common type of 9GC-ext-mag blockade found when laser-tweezer illumination is present.
Figure 50:
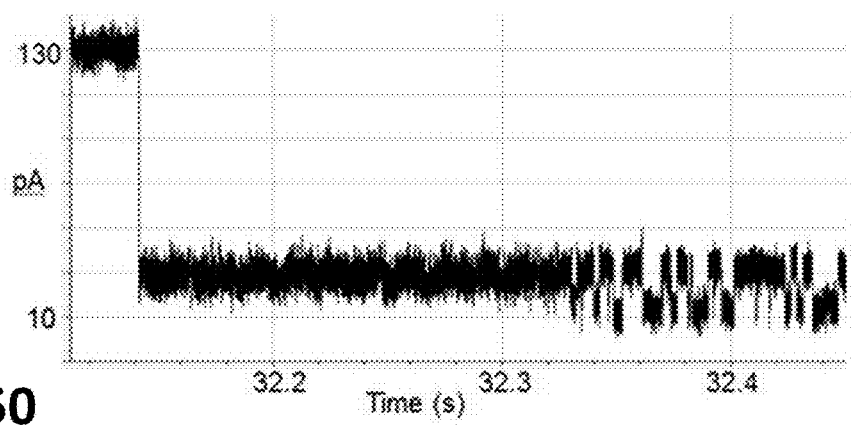
FIG. 50 illustrates an enlarged view of the toggle in FIG. 49.

FIG. 49 illustrates another common type of 9GC-ext-mag blockade found when laser-tweezer illumination is present (the lower twist level internal toggling is not seen without laser illumination). The blockade begins in the lower-level twist blockade (the upper-level twist state never occurs in this particular blockade event), and the molecule toggles in the lower-level twist state, via the usual orientation shifting not internal conformation switch as with the twist, between the normal 30 pA level and the 15 pA level. FIG. 50 illustrates an enlarged view of the toggle in FIG. 49. The lower-level twist blockade begins in its normal (upper) level (30 pA) then begins its laser-induced toggling to a lower lower-twist level (at 15 pA).

Clearly the twist toggle adds complication on top of the spatial configuration-toggle and this impacts the design of the transducers. Use of LNAs to lock the twist configuration is expected to eliminate the loop-stem twist toggle complication, but it's not as if the signal processing can't manage the two-toggle mode signal for most cases. So, the main purpose in tuning the LNA content in the LNA/DNA chimeras is to select the most effective transmission of binding event to the channel modulator, where most effective could be via twist mode transmission with large-mass long-tether (long DNA arm) (see. FIG. 17), while most effective may indicate very rigid (long of LNA) with low-mass short-arm tethering linkages.

Figure 51:
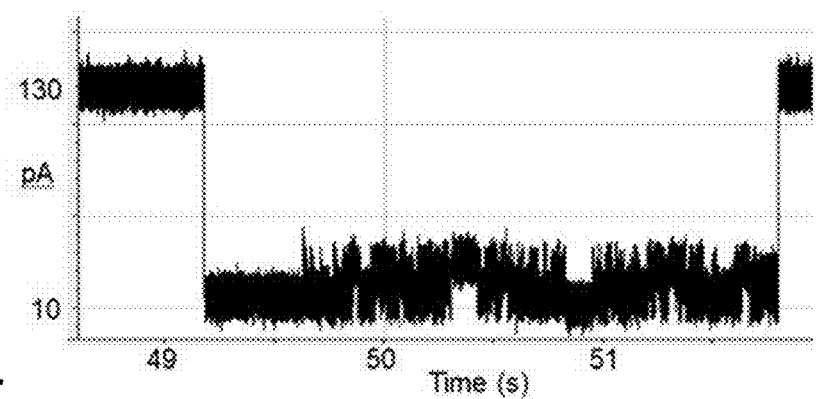
FIG. 51 illustrates a 2.5 s 9GCext_mag blockade with cage.

A large amount of twist toggling is associated with atypical shorter blockade: the DNA 20 bp hairpins typically lasted ~50-60 s, often several minutes, before diffusing away, but in some instances only lasted a few seconds. FIG. 51 illustrates a 2.5 s 9GCext_mag blockade with cage, starts at twist-LL then twist-LLtoggle, then twist-UL (which doesn't notably toggle), then twist-LL toggle, then twist-LL briefly stuck in its lower level, then twist-LL toggle. Sometimes there would be a lengthy twist-toggle event that eventually settles down to a fixed-level twist-LL blockade.

Figure 52:
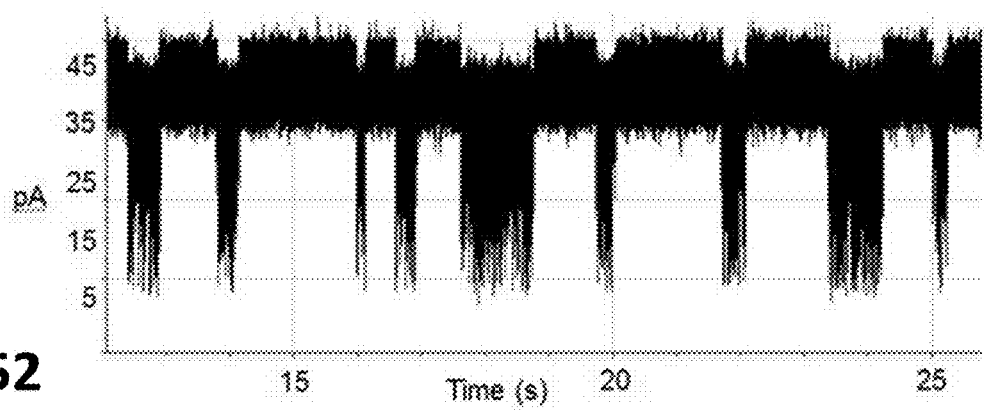
FIG. 52 illustrates a portion of the lengthy body of a 9GCext_mag blockade signal (with cage).
Figure 53:
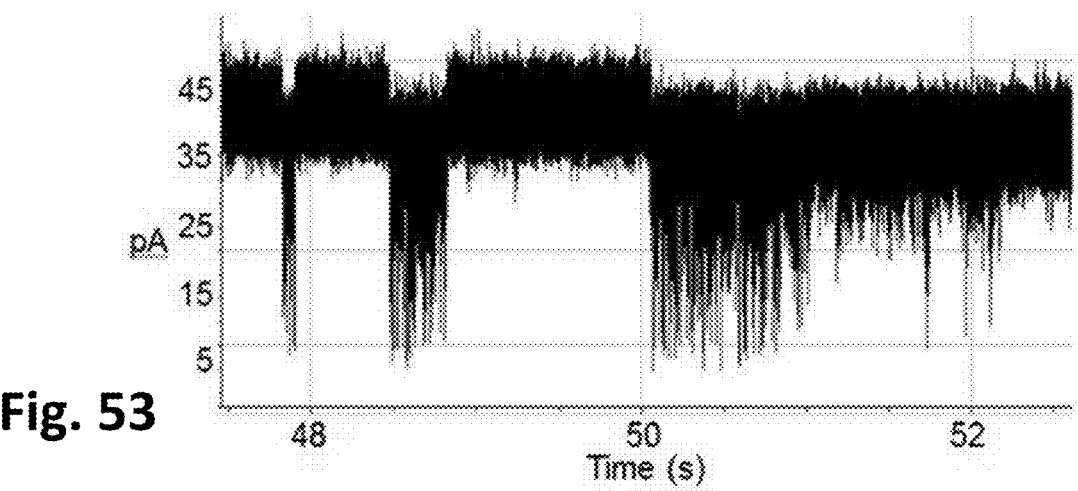
FIG. 53 illustrates the end of the twist-toggling part of the 9GCext_mag blockade signal shown in FIG. 52.
Figure 54:
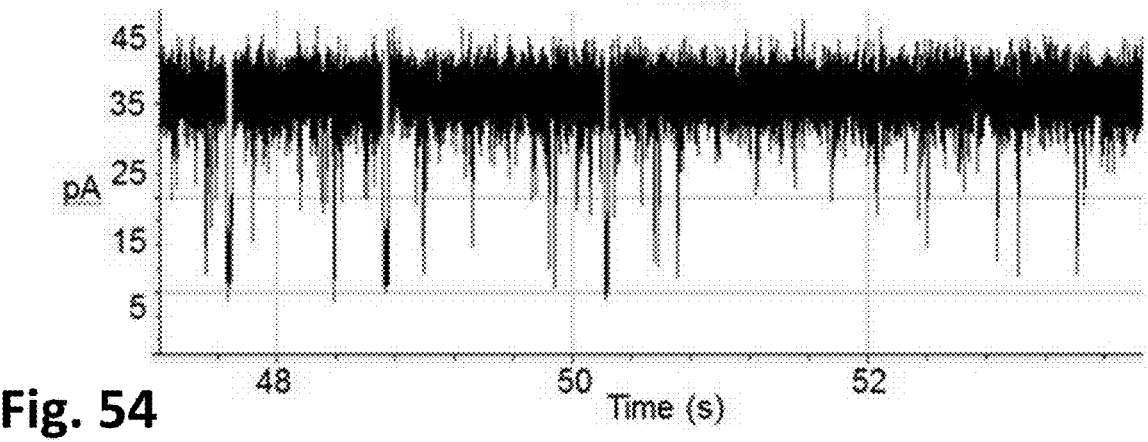
FIG. 54 illustrates an enlarged view of the transition to fixed level.
Figure 55:
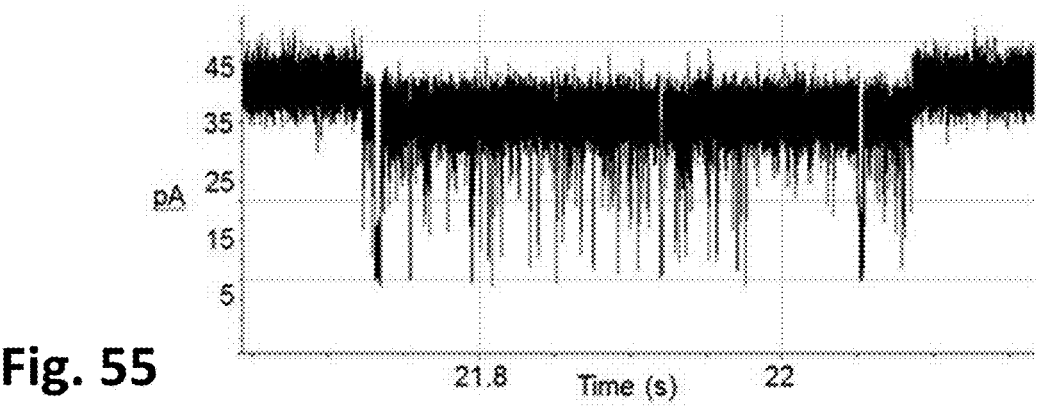
FIG. 55 illustrates an enlarged view of one of the twist-LL blockades from the middle of FIG. 51.

FIG. 52 illustrates a portion of the lengthy body of a 9GCext_mag blockade signal (with cage), about a tenth of the signal in this mode of toggling is shown. The molecule in the twist-LL state appears to be experiencing fraying-type 'spike' blockades (15 sec trace). FIG. 53 illustrates the end of the twist-toggling part of the 9GCext_mag blockade signal shown in FIG. 52. The final transition is to the twist-LL state, for which the fraying falls off until entirely gone, the blockade then continues in the twist-LL fixed blockade (without 'fraying spikes) for several minutes before ending. The signal shown in its lengthy toggle portion in FIG. 52 eventually trails off to the fixed level in FIG. 53. FIG. 54 illustrates an enlarged view of the transition to fixed level. For comparison, FIG. 55 illustrates an enlarged view of one of the twist-LL blockades from the middle of FIG. 51. The twist-LL state clearly exhibits the familiar fraying terminus type of blockade signal observed in other DNA hairpin studies on the alpha-hemolysin nanopore detector.

Interference Testing

In studies with interference on the control 9GC molecule it is found that 1 uL of 0.7 nM 9GC can easily be seen in the detector (that has 70 uL wells) in presence of 1 uL of 1 uM 7GC (approximately a 1:1000 ratio of 9GC to 7GC but easily discerned due to the distinctive channel modulation of the 9GC molecule). If analyzing the trace amounts of DNA present in blood serum (such as for early fungal pathogen identification), suppose 10 ng/mL of total DNA is present of which 1/1000 is due to fungal pathogen. If the fungal pathogen is 'reported' by a modified form of the 9GC molecule (or a Y-transducer) then it is necessary to 'see' 1/1000 of 10 ng/ml 9GC at the detector. Since 10 ng/mL concentration of 9GC is 1.5 nM, and we can see even less, 0.7 nM, when the rest of the serum DNA is interference (from accidental cell ruptures, etc.), then it is clear that detection can be done on trace DNA targets. Interference from other biomolecules that have higher pI is handled much more easily: 1 uL of 0.7 nM 9GC in the presence of 4 mg/mL hemoglobin (Hb) is easily resolved. Hb has a pI=6.87 (normal, sickle cell pI=7.09), so in the standard pH=8 buffer it is expected that some Hb should be delivered to the channel, but even when this occasionally occurs, it has no apparent interaction. This is in agreement with albumin interference results, where concentration=8 mg/mL, and with a pI of 4.7, it is expected that many of the albumin molecules should be delivered to the channel, but no significant channel blockade events or even brief 'noise-spike' blockades are seen (possibly because albumin is not glycosylated). In practice, an albumin capture matrix could be used to prevent the normally high levels of blood albumin (the main protein in blood plasma) from entering the nanopore detector, not to prevent interference with the channel detection per se, but to prevent bilayer interactions. Having entered the nanopore detector albumin can still potentially be blocked from bilayer interference by having a surface scaffolding on the bilayer from PEG linked albumin.

Similarly for cholesterol, where high concentrations are not found to have observable channel blockade effect. This is not to say that albumin and cholesterol have no effect whatsoever, they appear to have a beneficial effect via stabilizing the bi-layer to shock and to current leakage, and result in a lower RMS noise to the overall single channel current (no cholesterol, typical channel current RMS noise is 1.32 pA; with cholesterol it drops to 1.02 pA). The suspected role of albumin in channel nucleation is also revealed in these studies as late channel additions (bad news for single channel experiments) are observed to occur with introduction of albumin. Bilirubin has similar isoelectric point to albumin and similar non-reactivity with the channel.

Polyethylene Glycol (PEG) for Size Exclusion Chromatography and Filtering

Figure 56A:
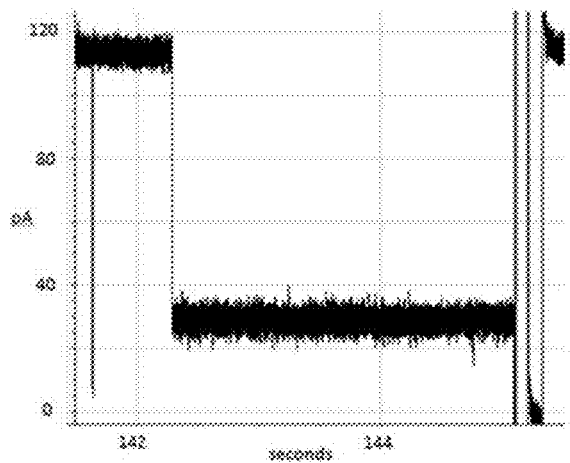
FIGS. 56A and 56B illustrate a DNA hairpin blockade signals before addition of PEG.
Figure 56B:
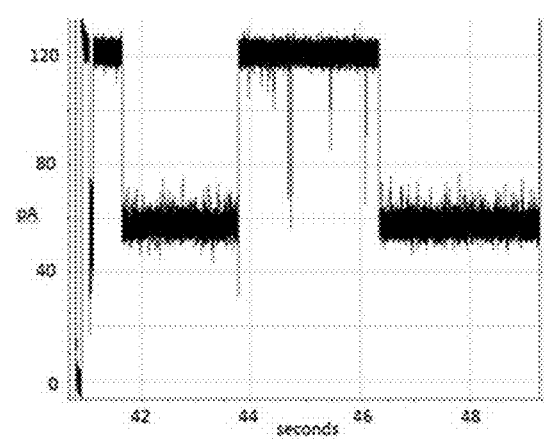
Figure 57A:
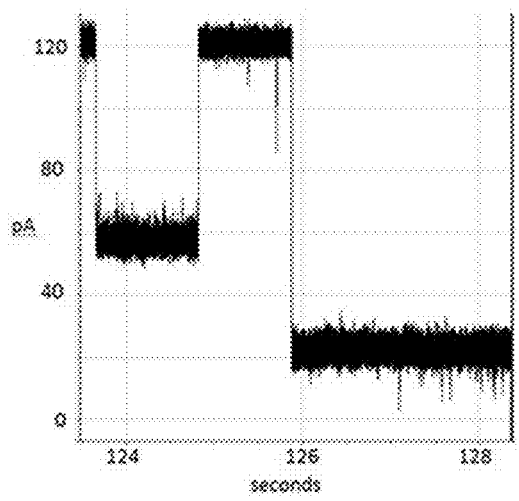
FIGS. 57A and 57B illustrate a 7CG and 12CG DNA hairpin mixture blockade signals before (FIG. 57A) and after (FIG. 57B) addition of PEG.
Figure 57B:
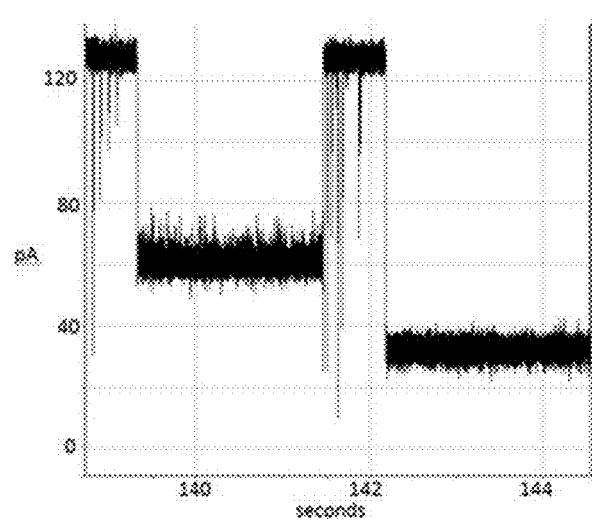

Introducing PEG into the buffer reveals strong size-exclusion chromatography fractionation effects, allowing species to be computationally grouped according to their PEG shift measurements then presented as an ordered 'computational gel-separated' list of species (affording gel-separation and blot-identification entirely on the NTD apparatus). FIGS. 56A and 56B illustrate a DNA hairpin blockade signals before addition of PEG. FIG. 56A illustrates a 12CG blockade and FIG. 56B illustrates a 7CG blockade. FIGS. 57A and 57B illustrate a 7CG and 12CG DNA hairpin mixture blockade signals before (FIG. 57A) and after (FIG. 57B) addition of PEG.

In the results shown in FIGS. 56 and 57, representative channel blockades are shown for two types of DNA hairpins, each with 4dT loops capping one end, one with seven base-pair stem (7CG molecule in Methods), one with a twelve base-pair stem (12CG molecule in the Methods). The Peg-shift in this instance should see a shift in channel events to favoring more channel events with the larger nucleic acid, 12CG over 7CG in these experiments. Before addition of PEG hundreds of 7CG and 12CG events were observed with the ratio of 12CG to 7CG events: 0.82. After addition of PEG the ratio favors 12CG: 1.33. There are also more counts overall. So have the overall appearance of greater concentration of 12CG (roughly twice), when it should be halved by the removal of volume to accommodate the dilute PEG solution addition. In other words, an effective ionic concentration increase due to the volume excluding effect of PEG on charged analytes, with increased volume exclusion effect on larger charged molecules like 12CG vs. 7CG. Embodiments for separating and examining individual nucleic acids, and assay methods, involving urea and PEG for example, can provide a general tool for analysis of nucleic acid profiles.

Biological System Analysis Comments

Embodiments provide a means to examine the binding and conformational changes of individual biomolecules in a non-destructive manner that is well-suited to non-destructive analysis of biomolecular systems. The critical choice of transducer in system biology NTD applications is for one with very high specificity but that is only weak binding so as not to be disruptive to the biological system or gene circuit. FIGS. 6 and 7 illustrate where the aptamer or antibody is engineered or selected to have weak binding, not high affinity as is typical in biosensing applications. Embodiments can also use the NTD method in live cell assays as well, via use of laser modulations, not for fluorophore excitation, however, but for noise state excitation for use by the NTD where the need to generate a steady channel current is avoided in detector operation (which would be destructive to the cell). The NTD method is typically based on a single protein-channel biosensor used with a patch clamp amplifier on a (synthetic cell membrane) lipid bilayer. In the live cell assay the patch clamp application would return to its origins, where it was developed for patch clamp measurements of currents and current gating through channels on live cells. In order for the NTD 'voltmeter' to operate on the biological system to work, however, the normal operational buffer of the NTD must also accommodate a change to the physiological or cellular buffer environment of the biological system of interest.

In addition to the study of DNA, DNA-DNA interactions, and DNA-Protein interactions, embodiments have significant potential vis-à-vis the study of protein-protein interactions on the single molecule level. DNA-protein and protein-protein interactions are an integral component of gene-regulation and the cellular signaling apparatus. Cell signaling networks, gene regulation, and pathogen-induced genomic or transcriptome modifications, are areas of intense current study since they are the basis for many disease states (ranging from metabolic disease, to cancer to autoimmunity). Fundamentally, the scientific benefits to molecular biology and a number of other fields (nanobiotechnology) are significantly impacted if nanopore detection methods can be utilized successfully in the system biology setting.

In the electrical engineering setting the extra element theorem (EET) allows circuits without feedback to be understood in the presence of feedback by choosing the extra element to be the feedback element. In electrical engineering this gives rise to an updated, quantitative, solution. In the stochastic Biosystem Extra-Element Theorem (BEET) setting, feedback complexity can be handled similarly. The BEET method allows a balance to be struck between reductionist and holistic approaches. In this setting it is possible to work with the 'black box' giving rise to the emergent behavior and consider perturbations to that system. BEET also shows how to evolve to gene circuits with more components via a series of small (evolutionary) changes.

Using embodiments to perform analysis of "gene circuits" it is, thus, possible to have a 'voltmeter for the circuit' in a circuit analogy. The NTD-quantified gene-circuit analysis can then be enhanced with use of (BEET) method for analysis. In the NTD BEET setting, a collection of NTD reporter molecules with specific binding to different molecules can be used to perform multiplex analysis of the system molecular profile by differentiating the reporter molecules according to their different channel modulation signals. The NTD BEET system could also employ multiple component modulation, and molecular knock-outs (by having strong binding) to effect double null injection to the equivalent gene circuit for a variety of extra element theorem testing procedures akin to their electrical engineering counterparts.

In the nucleic acid annealing studies on the NTD platform, the critical role of chaotropes for robust nucleic acid annealing studies on the NTD platform was determined (as shown in FIG. 5). The ability of the NTD apparatus to tolerate high chaotrope concentration, up to 5M urea, where the DNA hairpin control molecules demonstrated a manageable amount of isoform variation even at 5M urea, shown in FIG. 10. This allows a variety of annealing-based experiments to be robustly performed with nucleic acids, including miRNA binding site profiling in the presence of both known and unknown miRNA molecules, with or without complexation with argonaute proteins that occur in the RISC complex.

Preliminary work examining TBP binding to TATA binding site sequences placed in one arm of the Y-transducer construct suggest a similar construct could be employed for purposes of miRNA binding site validation. The Y-transducer for miRNA binding site profiling on mRNAs would take the hypothesized sequence of the miRNA binding region, typically from the mRNA's 3'UTR region, and incorporate it either into one arm of a Y-transducer, or incorporate it such that it crosses the Y-nexus (see FIG. 8), the latter case potentially offering the greatest sensitivity to binding events, as was seen in the Y-SNP construct described previously. The latter case may not allow sufficient steric freedom for miRNA binding, however, when complexed with argonaute protein, so the arm variant may still be necessary for analysis of some miRNAs. This approach to miRNA target validation also benefits from validation at the actual annealing step of the interaction, thereby accounting for possible modification to the miRNA such as may occur with adenosine deaminases, where adenosine deaminases that act on RNA catalyze the conversion of adenosine to inosine residues in some double-stranded RNA substrates. A subset of miRNAs have been found to have modulated processing efficiency when deaminated at particular residues, and this is now thought to impact a significant fraction of miRNAs.

The RNAi probe examination could also be reversed, where the miRNA is sought that is associated with a suspected miRNA binding site (such as when the 3'UTR motif has an anomalous rate of occurrence and is shared across homologous genes in multiple organisms).

A design process for NTD transducers is given, where use of LNA/DNA chimeras allows a much more robust long-lived reporter molecule. The engineered NTD transducer/ reporter molecule, minimally, has two functions, specific-binding and channel-modulation, and in the general setting, a third function to receive excitations such that channel modulation can be induced for all states of the transducer whether bound or not (with results shown here for when using a magnetic bead attachment in the presence of a laser-tweezer excitation).

The NTD methods proposed are compatible with using the NTD method in live cell assay settings as well, with use of laser modulations for noise state excitation for use by the NTD. The NTD method is typically based on a single protein-channel biosensor implemented on a (synthetic cell membrane) lipid bilayer, but in the live cell assay it would be based on patch clamp measurements of current through a channel on a live cell. The biosensor conformation used in the typical nanopore detector, however, is based on channel current blockades at discernibly different levels, which implies that there is at least one current that isn't zero, which is incompatible with using the standard cell patch clamp for channel biosensor applications (the cell would rupture). In the nanopore transducer setting, however, a minimal charge current could be used that could be non-destructive to the cell if periodically reversed, where most of the critical signal information would now reside in the noise profile (where the noise state would be driven by a laser-tweezer tugging at a covalently attached magnetic bead). The key signal analysis method to use in reading the changing noise states involves a collection of machine learning based signal processing methods comprising the stochastic carrier wave (SCW) platform.

Embodiments could be described as a programmable microarray. In essence, a programmable Southern Blot, Northern Blot, Western Blot, etc., is provided by the NTD given its direct computational coupling. Introducing PEG into the buffer also reveals strong size-exclusion chromatography fractionation effects, allowing species to be computationally grouped according to their PEG shift measurements then presented as an ordered 'computational gel-separated' list of species (affording gel-separation and blot-identification entirely on the NTD apparatus, when the destructive aspect of adding a bunch of PEG is permissible). A method and system for using the nanopore transduction detector (NTD) is, thus, described for examining the binding and conformation changes of individual biomolecules in a non-destructive manner, and by (destructive) assay methods, involving urea and PEG for example, that provides a general tool for analysis of biomolecular systems.

A simple NTD transducer design via LNA/DNA chimeras or via mAb selection is disclosed. NTD application platforms are described as well, including: Biosensor, Conformation-Binding Analyzer, Cell system monitor, and a direct protein (antibody) glyco-profiler. NTD transducers are typically constructed by covalently linking a binding moiety of interest to a nanopore current modulator, where the modulator is designed to be electrophoretically drawn to the channel and partly captured, with its captured end distinctively modulating the flow of ions through the channel. Using inexpensive (commoditized) biomolecular components, such as DNA hairpins, this allows for a very versatile platform for biosensing, and given the high specificity high affinity binding possible, this also allows a very versatile platform for assaying at the single molecule level, even down to the single isoform level, e.g., molecular substructure profiling, such as glycosylation profiling. (Glycosylation profiling can also be done directly for some molecules that directly produce toggling blockades, antibodies in particular. Glycosylation profiling is of critical importance in the development of the most effective antibody treatments.) Two complications with the transducer design, however, are (1) the convenient DNA-based modulators are often short-lived; and (2) the overall transducer's bound state often doesn't modulate. The first is shown to be solved using locked nucleic acid (LNA) nucleosides, the second is solved by introducing a third functionality for receiving laser-tweezer impulses by means of a covalently attached magnetic bead (another commoditized component). A description of the detector's robust performance in the presence of numerous interference agents with very low analyte concentration was also needed, and this is now much more clearly affirmed. LNA Y-transducers with magnetic bead attachment and laser pulsing gives rise to a generic modulator arrangement (shown in FIG. 11), that modulates even when bound, to allow NTD probing over long timescales on biological system components. An inexpensive commoditized pathway for constructing nanopore transducers is thereby obtained.

Protein Conformation-Binding Comments

Due to its strong NTD quantitative basis with observing individual events and species and getting their relative frequencies over time, it is possible to do a number of very refined titration analyses in the nanopore setting. Consider first isoelectric focusing (IEF) gels, where you have electrophoresis in a pH gradient that is established over some spatial extent (the run length of the gel). With the nanopore we have electrophoresis when the frequency of species seen can be tracked as the pH is very slowly titrated over time. The pI of a molecule could then be identified as when its counts change significantly when titrating ph. This approach is limited to those molecules that produce channel blockade, which is conveniently the case for antibodies. In the case of the antibody can also get 'surface pI' mappings by tracking the frequencies of the different (glycoform) variants seen at the channel at a different pH—surface features with surface pI favoring negative charge will have preferred capture at the nanopore. This can be taken a step further with use of chaotropes to slowly titrate chaotrope and strip away different types of glycations according to their protein binding strength and susceptibility to chaotrope (hydrogen bonding especially). If done on a fully automated, quantified setting like the NTD, the number of types of glycations on a sample, and the relative frequencies of those glycations, could be determined.

A design process for NTD transducers is given, where use of LNA/DNA chimeras allows a much more robust long-lived reporter molecule. The engineered NTD transducer/reporter molecule, minimally, has two functions, specific-binding and channel-modulation, and in the general setting, a third function to receive excitations such that channel modulation can be induced for all states of the transducer whether bound or not. This is demonstrated to be possible by NTD results from introducing a magnetic bead transducer attachment in the presence of a laser-tweezer excitation.

Alternatively, antibodies, monoclonal antibodies (mAb's) in particular, can be directly used as transducers since they provide modulatory channel blockade (with stationary signal statistics as needed for the stochastic carrier wave methods), and they have specific binding for their antigen. The problem with antibodies in a direct capture arrangement, however, is that there is a great variety of direct capture orientations for antibodies, revealing that using antibodies directly in a biosensor role effectively requires first understanding the glycosylation profile of the antibody and probably C-terminus features and glycations as well. Understanding the glycosylation profile of an antibody is itself an area of great interest in quality control on antibody production.

The inexpensive and versatile process for producing an NTD transducer for a protein of interest, or protein-feature of interest, whether LNA/DNA based, or mAb based, opens up the possibility of tracking the conformations of a single protein and their role in protein function, binding in particular. NTD operation recently been demonstrated for a wide range of pH, chaotrope concentration, and in the presence of interference agents that would encompass the 'native' environment of a protein of interest. So the ability to analyze a 'bare' protein, with glycations stripped, using a nanopore is now more accessible. Many proteins of biomedical interest are actually mixtures of glycoproteins, however, with different levels of glycosylation and glycation, where the glycation proportions are transient, and are derived from the blood sample of a patient where numerous interference agents are present. For such samples the assay of the proteins behavior must not only operate at the single molecule level, but must discern subtle isoform modifications quickly given the transient existence of certain glycations. The tolerance of the NTD platform for high chaotrope allows a glycoprotein profile to be determined in addition to a conformation interaction profile, and suggest a method for performing complete characterization of biomolecules that is comparatively inexpensive.

Isoform-Specific Comments

It is shown that nanopore-captured DNA hairpin modulators can exhibit not only spatial/orientation toggling but also torsional/twisting toggling when sufficiently excited. This effect becomes most notable when channel modulations are induced by laser-tweezer pulsing, but has been observed in other high-strain conditions for captured DNA hairpin channel modulators, such as high chaotrope, high pH, high applied voltage, and high mass/charge capture events. The new understanding of the laser-tweezer induced modulations suggests a limit for the induced modulator's signal classes to those already seen and a manageable signal analysis platform can thereby be implemented. In practice a stochastic channel modulator that produces the simplest, non-fixed-level, stationary signal blockade is desired, such that the stochastic carrier wave (SCW) signal processing methods can be employed. The position and twist toggle modes in the modulator together pose a more complex SCW system, but could be managed with sufficient sample observations on modulator during its different states (such as linked to bound or unbound analyte).

A related problem with the DNA-based channel modulators has been their short lifetimes until melting. This problem has been eliminated by use of LNAs, where LNAs also serve to reduce twist modes as needed as well, to simplify the SCW basis mentioned above. Since the simpler SCW analysis is not critical, however, the main optimization to be accomplished by 'locking up' the modulator with increased LNA is effectively a tuning over molecular variants with greater or lesser twist mode event transmission. A general method for transducer construction is thereby suggested with twist-mode dominated state tracking for large charge/mass biomolecular complexes with long duplex DNA tether constructions, and configuration-switching dominated state tracking for small charge/mass biomolecule complexes with short-linkage constructions.

Embodiments provide functionality in three main areas: (1) air-quality and water-quality testing; (2) binding on large molecular features, large cell-surface features, and heavy metal chelation binding; and elated design of diagnostic/therapeutic transducers with both aptamer and antibody components, where the Ab targets to the tissue or tumor of interest, and the aptamer is a tissue directed drug; and (3) isoform assaying.

For air-quality testing a capture matrix (a specially designed filter) can be employed to collect a sample of the particulates present. The particulates collected are then eluted into a solution and can be bound to nanopore transduction molecules designed to specifically bind to the molecule(s) or particulate(s) of interest (as shown in FIG. 7 for an aptamer-based reporter/transducer and FIG. 8 for an antibody-based reporter/transducer), with subsequent reporting by that bound reporter to the nanopore transduction device.

Testing on water quality is easier as it skips the capture matrix step, and proceeds directly to mixing the water sample with a NTD reporter solution. A quantification of the amount of bound versus unbound reporter molecule detected at the nanopore transduction detector then allows the concentration of the target molecule (or particulate) to be determined. As with the NTD assays done in the laboratory setting, the assays can be completed in minutes, or possibly even seconds, depending on the concentration of the analyte of interest.

High specificity and affinity air and water biosensing using aptamers is much more accessible than mAb methods given the stability of aptamers at room temperature, and may provide highly beneficial application in settings where there is significant heavy metal poisoning in the water supply (or to the air due to chemical spraying). Whether considering air or water biosensing the mass production ease of aptamers is another significant advantage over mAb-based procedures. What is missing, however, is a mass discovery and refinement mechanism, where one possible solution involving the NTD is a variant of the NADIR SELEX procedure that introduces aptamers that are multifunctional, refining the specificity and affinity for a particular molecule or molecular feature, as with a standard aptamer, with a possible second binding function via aptamer or antibody, and having for another function the channel-current modulatory properties of a nanopore transduction reporter molecule that allows the binding properties of the binding moiety or moieties part to be directly assayed via the nanopore transduction detector (NTD) method.

As previously discussed, therapeutic use of aptamer methods have begun to get FDA approval in two settings: (1) dialysis therapy where aptamer-based filters are used to clean a patient's blood of accumulated kidney or liver toxins that are not being cleared due to damage to those organs; and (2) tissue or tumor directed treatments where the aptamer is linked to an antibody already known to target and localize to the tissue or tumor of interest.

In some settings, with large molecular features, large cell-surface features, or heavy metal chelation binding, more complex aptamer transducers, linked double-aptamer constructs, and dual aptamer/antibody binding moieties, all with nanopore modulator components, are indicated. The latter two arrangements are trifunctional in that they have two binding moieties and a nanopore modulatory component, for which NADIR augmented SELEX is even more advantageous. If a fourth functionality is introduced to receive laser-tweezer tugging, by linking a magnetic bead, then quadfunctional modulators are sought, strongly favoring the more directed tuning allowed with the nanopore detector.

One challenge for a molecular analyzer is to differentiate isoforms when there are hundreds of available isoforms. Using NTD reporter/transducers that are developed to specifically bind to only one cannabinoid, or just one of the nine main types of cannabinoid, a more refined assay can be developed. Since the task is inherently multiplexed by the hundred or so different cannabinoid targets that require quantification, it is important to not only be able to identify the bound/unbound state of the different cannabinoid transducers, but to tell the different transducers apart from one another if simultaneously assayed in a mixture. Mixtures of DNA hairpins that differ only in their terminal base-pairs have been resolved with 99.9% accuracy, so the capability to engineer the bases of the Y-transducers such that they can be easily discriminated are known. However, embodiments implement a mixture of cannabinoid Y-transducers, differing in their aptamer or antibody targeting arms, and in their associated Y-base terminus blockade signal, to arrive at an inexpensive process for multiplex cannabinoid profiling. Since little is known about the different cannabinoids due to the lack of developed assaying methods, their number could be far more than the 113 or so currently discovered, possibly numbering more than 200. Since aptamers can be created in large quantities they have already become popular for use in biomarker discovery, similar procedures can be used here for novel cannabinoid discovery using aptamers as well.

A general method for nanopore transduction detection transducer construction is proposed, with transducers based on LNA/DNA chimeras that have twist-mode dominated state tracking for large charge/mass biomolecular complexes with long duplex DNA tether constructions, and configuration-switching dominated state tracking for small charge/mass biomolecule complexes with short-linkage constructions.

The general-use nanopore transduction detector system offers the prospect for high-specificity molecular, molecular feature, and particulate testing (whether air-quality and water-quality testing), not only in the lab setting, but also the field setting. High-specificity detection is possible by incorporating the high binding specificity of aptamers and monoclonal antibodies for their binding targets into a nanopore binding-event transduction system. Once a binding event is transduced to an electrical ionic current flow measurement, novel channel current cheminformatics and machine learning methods are introduced for event classification. A quantification of the amount of bound versus unbound reporter molecule detected at the nanopore transduction detector then allows the concentration of the target molecule or particulate to be determined.

Aptamers are nucleic acids with specific binding to a particular target molecule or molecular feature. Aptamer selection is done by a rapid artificial evolutionary process known as SELEX. Nanopore transduction directed 'NADIR' augmented SELEX has been suggested for improved aptamer design and selection when working with multifunctional aptamer design. The more complex aptamer transducers are particularly relevant when considering therapeutic uses of aptamer methods, where the aptamer is linked to an antibody already known to target and localize to the tissue or tumor of interest.

In the challenging area of resolving isoforms and other minor variants, consider that over a hundred different cannabinoids have been isolated from *Cannabis*. What is needed is a method for inexpensive assaying of *Cannabis* profiles that provides not only the ability to specifically bind a particular cannabinoid with high affinity, but a means to multiplex profile a mixture of cannabinoids with high accuracy. A nanopore transduction detector could be used to address this problem as well, where the aptamer or monoclonal antibody selected for the specific cannabinoid binding of interest is linked to a uniquely modulating NTD transducer for direct quantification on the relative abundances of the different cannabinoids.

Rapid Viral Testing

Embodiments make use of a mixture of technologies old and new: (1) a carefully selected set of restriction endonucleases is chosen to cut the Zika genome into segments of DNA that are suitably unique in and of themselves or when taken in groups of two or three segments, and (2) a DNA Y-reporter molecule is designed to anneal to those unique Zika segments and transduce their annealed versus not-annealed state into discernibly different channel current readings in a NTD device (see FIGS. 8 and 14). The rapid viral test procedure is equally applicable to fungal and bacterial infection and can be designed to distinguish the strain of the infection if the genome for that strain is known. A critical complication in embodiments for the robust use of the NTD approach in annealing-based tests is the use of chaotropes. Chaotropes, such as urea, weaken binding such that simple binding interactions and nonspecific DNA binding interactions are eliminated as a source of noise, while the collective binding seen with nucleic acid annealing is retained, allowing for improved recognition of annealing events. In recent work it has been shown that NTD operation is remarkably robust in the presence of high concentrations of chaotrope and interference agents, making NTD application to DNA-annealing based diagnostics directly accessible.

For a viral test, embodiments differentiate changes and counts on Y-transducers that "walk" target. If all of them turn on for a reporter set, then have detection. The same walker method can be used to identify a standard subset (biomarker discovery style) that fingerprints an unknown disease, and see if it is present in another patient. The molecule inherently provides the specificity for target binding by design. To have sensitivity the molecule is, fortunately, already charged for favorable electrophoretic separation. This can be enhanced further with use of PEG as shown here, via a size exclusion chromatography mechanism on charged molecules, while simultaneously delaying and filtering passage of albumin and other interference molecules. It may be possible to pretreat the bilayer with PEG-albumin, then have an analyte chamber and microfluidics connecting column that has buffer with PEG. Both PEG uses require active PRI-rejection on long blockades that aren't modulatory with stationary signal statistics to protect the channel.

If significant voltage reset toggling is needed to keep the channel operational, the data acquisition (with any patch clamp amplifier) will have significant amount of the signal event of interest during the messy variable capacitive resets (i.e., there will be significant number of blockades with respect to a non-steady discharge/recharge curves, not a fixed baseline level). Extracting signal in this situation has been done using an FSA, where an adaptive boxcar filter is effectively implemented.

miRNA Seed Cluster Haplotyping

Embodiments disclosed below are directed to the nanopore and transcriptome analysis of fish. However, the same functionality can be applied to the profiling of *Cannabis* strains by replacing all the fish categories with *Cannabis* strain categories and instead of a biomarker for ecotype collapse in a particular fish species, looking for a biomarker or gene for a preferred cannabinoid, etc.

Characterization of Fish Stock Diversity Via EST-Based miRNA Trans-Regulation Profiling Many current fishery stock assessment methods strongly rely on the amount of fish harvest reported at the dock by fishermen. In contrast, embodiments perform fish stock assessment that is based on transcriptome measures. Embodiments provide a correlation between transcriptome level diversity and changes in the phenotype expression ability of commercially targeted fish. By analyzing the complexity of miRNA/RNAi 7mer binding sites in the 3'UTR regions, inferences are made as to the accessible repertoire of phenotypes for the organism. If fewer phenotypes are available, for use in response to environmental change, or for use in extending habitable niche, such as by 'schooling', then significant loss of fishery stock may result. Preliminary results indicate Gadus Morhua (Atlantic Cod) has undergone such a loss in transcript regulatory complexity, which appears to be associated with the collapse of the Cod fishery in the Gulf of Maine.

Studies of individual regulatory elements in a variety of species have demonstrated the prevalence of functional motif conservation without sequence conservation. This would indicate that the sequence meta statistics, such as on distributions of anomalous regulatory motif counts, might remain the same, while the individual sub-sequences with anomalously high counts, for example, might be significantly changed from one species to the next. Where strong sequence conservation does hold, there is often associated some constraint on the encoding that prevents neutral drift to another motif sequence (such as with the overlap encoding regions).

Cleavage stimulatory factor ("CstF"), is a 200 kDA heterotrimeric protein which assembles onto the 3' end of a pre-mRNA (probably as a dimer). CstF binding promotes the polyadenylation process. Once polyadenylated, the mature mRNA is ready for export outside the nucleus. Not surprisingly, the amount of CstF depends on cell cycle. CstF is also known to play an active role in response to DNA damage, where it has been found that cells with lower levels of CstF have less viability for survival following UV exposure. CstF is seen to play a critical role in tumor cells as well. Many tumors have been found to have a mutated p53 gene (the most commonly mutated gene in human tumors). Recent studies of p53 show that it inhibits mRNA 3' processing via interaction with CstF. P53 is also known to transactivate miRNAs, allowing large changes in expression for miRNA targeted genes in later post-translational processing. P53 and CstF together are at the nexus of a critical regulatory control via 3' processing. Not surprisingly, as we will show, the motif 'footprints' of the CstF binding site are one of the most statistically strong motifs (high count anomalous) in the 3' region of mRNAs. The prevalence of the CstF motif seen in the 'healthy' species is found to be reduced and less varied in damaged fish stocks (as will be shown), and is associated with reduced, less targeted, CstF binding.

Transcriptome-wide comparisons have been done via SNP profiling, where identification and use of SNP markers permit a fine-scale stock identification and tracking, and could eventually allow a deeper understanding of ecotype divergence. In a study of pacific herring almost 11,000 potential SNPs were identified, of which 96 were directly tested. Of those 96, six were found to provide excellent sub-population biomarkers. SNP discovery is more scalable than SNP validation. SNP validation is inherently more difficult than motif validation in that the single nucleotide has no additional implicit information than the 'one bit' of information typically encoded in a two-state SNP. A motif that is 10 bases long, on the other hand, has 4ˆ10=2ˆ20~=10ˆ6 possibilities, of which some can occur with anomalously high counts, allowing for six orders of magnitude greater internal or 'implicit' information content. This allows a preliminary validation process to be done much more in the computational (scalable) realm, if not entirely computational if referring to a meta-level statistical analysis as we will be being done here.

Embodiments provide an investigation into transcriptome diversity, and associated phenotype expression ability, of commercially targeted fish. This is done by analyzing the complexity of miRNA/RNAi 7mer-based regulatory motif footprints in the 3' untranslated region (3'UTR) of protein coding transcripts. There appears to be a 'normal' 7mer count distribution profile. A reduction (or significant deviation from normal) in these motif footprints correlates with loss of transcriptome diversity and a less abundant stock.

The transcriptome/EST data analysis is done using on ORF-finder program written in Perl. EST 3'UTRs are identified, wherein anomalously recurring 7-base sequences, known as "7mers," are sought. By analyzing the distribution on 7mers, a crude assessment of transcriptome regulatory diversity is inferred, with possible implications for fish stock assessments.

Embodiments perform transcriptome-wide studies that include transcript fingerprinting not via a SNP profile on each transcript, but via a miRNA binding site (7mer) profile on each transcript's 3'UTR region. By doing a meta statistics analysis on the anomalous motif occurrences, evidence of significant trans-regulatory damage in Atlantic Cod (*G. morhua*) which is known to be in an overfished status where overfishing is shown to still be occurring.

Current Fish Stock Assessment Methods

Fisheries stock assessment refers to the analysis of the past and current status of a group of fish that live in the same geographic area, in order to learn more about the effects of fishing and other factors. The information obtained from stock assessments helps fisheries managers make sustainable decisions.

Stock assessments are done using models which rely on three different types of data: catch, abundance and biology. Catch data is simply the amount of fish taken from a stock of fish by fishing. There are many ways fisheries managers can obtain this data, including dockside monitoring, logbooks from commercial fishermen, observers that go to sea with commercial fishermen, and sampling the catch of recreational anglers. Abundance data is a measure or representation of the amount of fish that are actually in the stock. This type of information usually is generated by a statistical model which analyzes sampling data from fishery-independent surveys. These surveys take place on research vessels or contracted fishing vessels and use standardized sampling methods. Biology data adds the aspect of individual fish growth and mortality into the model. Some aspects of biological data that are incorporated can include growth rates, reproductive rates and movement.

The models which are used to conduct stock assessment differ among different commercial fisheries, and are limited by the amount and type of data available to use. Many other factors are also often incorporated into these models. A species' position in its larger food web, competition between other species, habitat and physical environmental conditions are all other aspects that can be taken into account. While some fisheries are very well maintained, others may need some work to better the way in which they are maintained.

Entropy Measures, Statistical Linkage, and Mutual Information: Codon and ORF Discovery The degree of randomness in a discrete probability distribution P is measured in terms of Shannon entropy:

$$S(P) = \Sigma_k p_k \log(p_k).$$ where $P$ has outcome probabilities $\{p_k\}$.

When comparing discrete probability distributions P and Q, both referring to the same N outcomes, the proper measure of their difference is measured in terms of their (possibly symmetrized) relative entropy (a.k.a. Kullback-Leibler Divergence): $D(P\|Q) = \Sigma_k p_k \log(p_k/q_k)$. where P and Q have outcome probabilities $\{p_k\}$ and $\{q_k\}$. In evaluating if there is a statistical linkage between two events X and Y the probability of those events being independent are determined (e.g., does P(X,Y)=P(X)P(Y)?). Since this reduces to measuring the difference between two probability distributions: P(X,Y) and Q(X,Y)=P(X)P(Y), the relative entropy between P and Q is sought, where D(P(X,Y)∥P(X)P(Y)) is the definition of 'mutual information between {X,Y}: MI(X,Y)=D(P(X,Y)∥P(X)P(Y)).

Figure 58A:
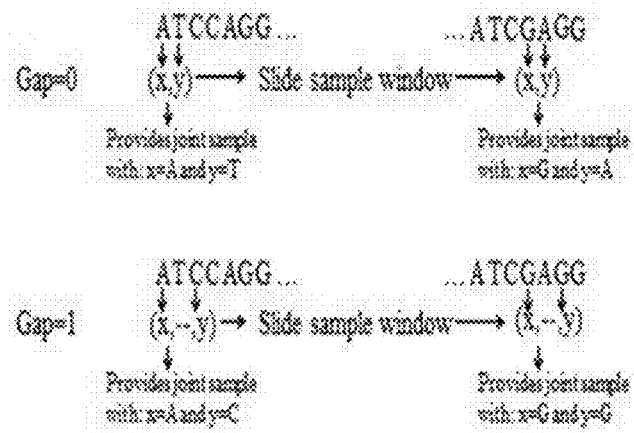
FIGS. 58A-58B illustrate a codon structure revealed in the *V. cholera* genome by mutual information between nucleotides in the genomic sequence when evaluated for different gap sizes.
Figure 58B:
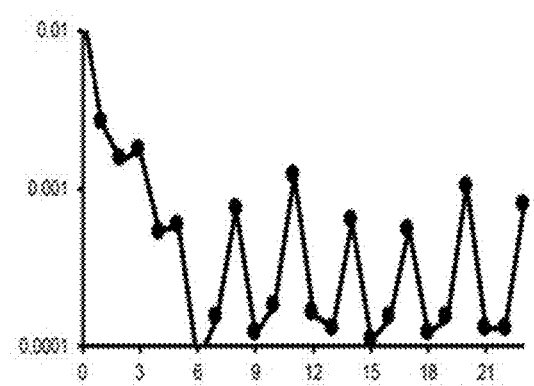

Mutual information allows statistical linkages to be discovered that are not otherwise apparent. FIGS. 58A-58B illustrate a codon structure revealed in the *V. cholera* genome by mutual information between nucleotides in the genomic sequence when evaluated for different gap sizes. Mutual information between nucleotides in genomic data when different gap sizes considered between the nucleotides is shown in FIG. 58A. When the MI for different gap sizes is evaluated, as shown in FIG. 58B, a highly anomalous long-range statistical linkage is seen, consistent with a three-element encoding scheme (the codon structure is thereby revealed).

Once codon groupings are revealed, a frequency analysis on codons can be done, and the 'stop' codons are found to be rare. Focusing on the stop codons it is easily found that the gaps between stop codons can be quite anomalous compared to the gaps between other codons. Open reading frames ("ORFs") are regions that have no stop codon {(uaa),(uag),(uga)} when traversing with a particular codon framing. The restriction to larger ORFs is due to their highly anomalous occurrences and likely biological encoding origin, e.g., the long ORFs give a strong indication of containing the coding region of a gene. By restricting to transcripts with ORFs>=300 in length, a resulting pool of transcripts that are mostly true coding transcripts is obtained.

Figure 59:
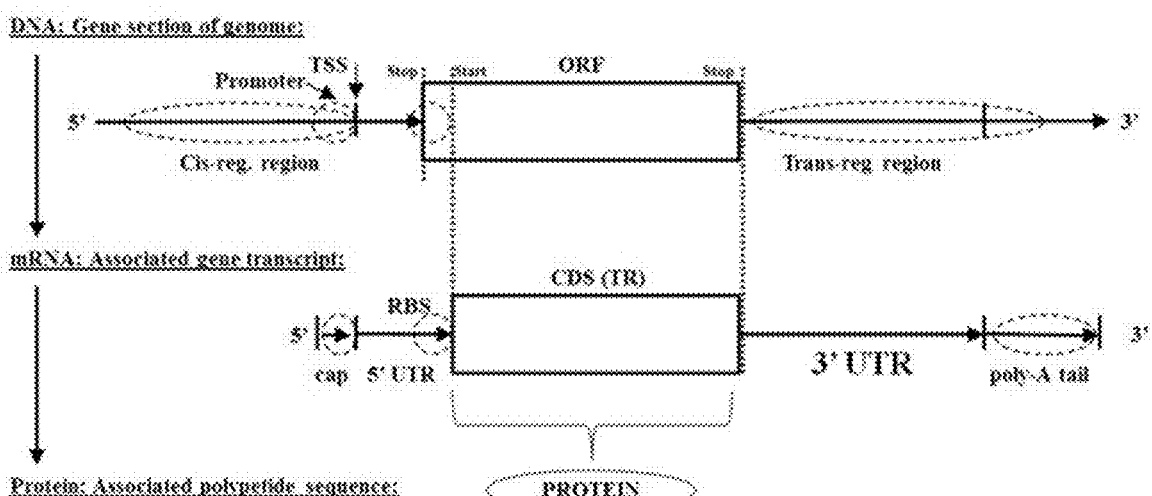
FIG. 59 illustrates the cis- and trans-regulatory regions.

Once the anomalous ORF structure is identified, nearby associated encoding anomalies are discovered (which in turn serve as validators), such as transcription start site recognition, in case of genomic sequence, or start/end of coding region recognition, in case of genomic or transcriptomic sequence information. FIG. 59 illustrates the cis- and trans-regulatory regions, with cis-regulation via protein transcription factors dominating for DNA→mRNA regulation, and miRNA template strand recognition (via RNAi) regulation dominating mRNA→protein processing.

A transcriptome-wide study is done on numerous species of fish. For a given species, the length distribution on their 3'UTR regions is examined, with specific plots shown for three species of fish, where the selection of >300 ORF and >200 3'UTR is made in the initial data handling (as summarized in Table 4 below).

Computational Methods

Figure 60:
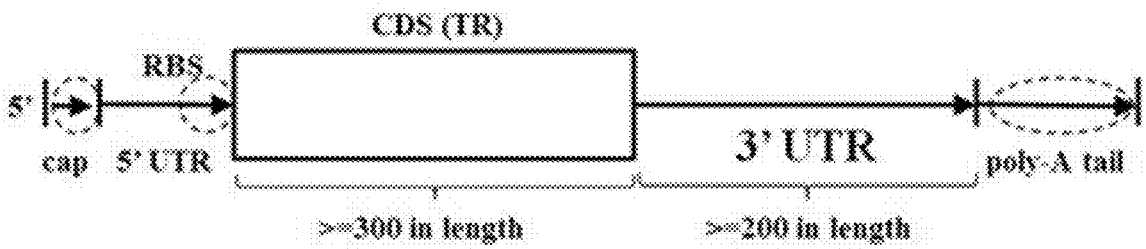
FIG. 60 illustrates transcript selection: >=300 length ORF region and >=200 length 3'UTR region.

Embodiments focus on data presented at the transcriptome level, particularly that from EST processing. This allows analysis to be done at the earliest opportunity since EST generation is an essential first step in genome construction, SNP discovery, and microarray design. Assuming the collection of transcripts has already been filtered such that each transcript has at least one ORF length greater than or equal to 300 nucleotides, can further filter according to retaining those transcripts with 3'UTR regions 200 nucleotides in length or greater (as shown in FIG. 60), with results as shown in Table 4 below. FIG. 60 illustrates transcript selection: >=300 length ORF region and >=200 length 3'UTR region.

TABLE 4

| Species | Genbank ESTs | uniq_ORF >= 300 | 3UTR >= 200 |
|---|---|---|---|
| Tuna | 10,163 | 5,366 | 1,739 |
| Salmon | 498,523 | 232,014 | 96,084 |
| Cod | 257,255 | 117,443 | 41,673 |
| Catfish | 139,475 | 60,094 | 24,558 |
| Pufferfish | 26,069 | 11,274 | 2,599 |
| Cyprinus | 47,738 | 26,579 | 10,166 |
| Dicentrarchus | 55,837 | 25,929 | 9,904 |
| Disso | 37,104 | 17,371 | 4,803 |
| Hippoglossus | 20,836 | 15,066 | 5,659 |
| Osmerus | 36,788 | 28,693 | 16,040 |
| Sparus | 29,216 | 38,034 | 8,710 |
| Zebrafish | 1,488,339* | 121,554 | 44,253 |
| Astyanax | 189,864 | 118,036 | 43,094 |

Referring to Salmon from Table 4 as an example: there are 498,523 EST transcripts from Genbank that are validated via a high-confidence BLAST score alignment to a Genbank-annotated protein coding mRNA. These EST transcripts are scanned with six ORF-finder passes: three ORF passes in the forward direction, for the three positive strand ORF frame-passes, and three ORF frame-passes on the reverse-compliment strand for the negative DNA strand genes. There are three frame passes because the codon encoding element is three bases long, such that a tiling over the sequence with codons is possible with three different codon 'frame' conventions. Transcripts are restricted for which at least one ORF>=300 bases in length is found according to any of the six aforementioned frame-passes. Of the ORF>=300 sequence, further restrictions are to those having 3'UTR regions greater than 200 bases.

Figures 61A, 61B, 61C:
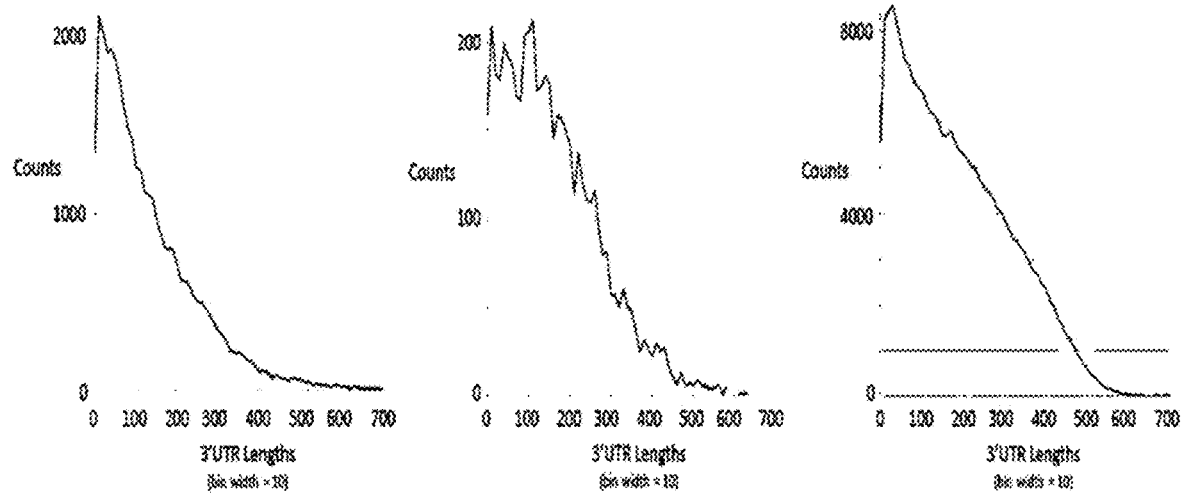
FIGS. 61A-C illustrate the 3'UTR length histograms for three species of fish.

The cutoff of >=200 3'UTR length is justified on a similar basis to the ORF cut-off that is typically used (disclosed above). As with the ORF length distribution, the 3'UTR distributions reveal a clear deviation from geometric fall-off on length (as might be expected from a random process), and if sufficiently far into the heavy tail region (with non-zero counts), where the geometric distribution fit would indicate a zero count, then all such instances have a high likelihood of pertaining to a biological encoding. FIGS. 61A-C illustrate the 3'UTR length histograms for three species of fish. FIG. 61A illustrates tuna, FIG. 61B illustrates salmon, and FIG. 61C illustrates cod.

In each instance in FIGS. 61A-C, a fit to a geometric distribution can be based on the short 3'UTR lengths (just as with short ORF lengths) to estimate the random approximately geometric distribution, from which the deviation of the actual length distribution is can be estimated. For the species shown in FIGS. 61A-C and also listed in Table 4, the deviation is notable for lengths >=200, thus the choice of cut-off. What is perhaps even more notable is that species-wide uniformity in the maximal 3'UTR lengths. Note in FIGS. 61A-C that there are no 3'UTR regions greater than 600 bases, with very few greater than 400 bases. The same is also found to hold for the other fish in Table 4, and for human, mouse and a number of other organisms (not shown). A heavy tail 3'UTR distribution with strict fall-off to zero at 600 length or longer serves as a further validation on acquisition as well, since it appears to be a universal.

Results

As disclosed above, Genbank mRNA/EST data is downloaded, filtered, and rudimentary validation is done. In this process all of the fish 3'UTR regions shared similar meta-statistical features as already mentioned. Table 5 below shows further transcriptome-wide processing for the fish species described in Table 4. The first column describes the transcripts obtained after the aforementioned ORF>=300 and 3'UTR>=200 filters, plus the added filter of requiring that the first 35 bases in a 3'UTR region be unique (otherwise take the longer transcript and discard the other). The transcripts meeting the various filters indicated are then passed through a prokaryotic gene-finding program that does three ORF passes in the forward direction then three ORF passes on the reverse complement read of the sequence. The six ORF passes filter according to the ORF>=300, 3'UTR>=200 and '35uniq', and their overlap topology is noted. If a transcript has both forward and reverse encoding, each of which meets the strict filtering criteria (ORF>=300, etc.) then the transcript is referred to as 'dual' in Table 5. The extent of dual encoding revealed at this stage of the transcriptome-wide validation process is surprising result. A universal amount of 'duality' appears to occur in the 7%-15% range (and this is seen to hold for human and mouse and other transcriptomes as well). The amount of same read direction overlap encoding is also significant, and also typically falls in a range (between 11% and 18%) that can serve to validate acquisition.

TABLE 5

| Species | # of Genbank mRNA/EST sequences with ORF >= 300, 3UTR >= 200, & uniq35start | % column1 mRNA/EST sequences that are dual | % ORFs from column1 sequences that are in (loosely filtered) operons | % ORFs from column1 overlapping with same read direction: |
|---|---|---|---|---|
| Bluefin Tuna Thunnus thynnus | 1541 | 9.5 | 0.63 | 11.8 |
| Atlantic Salmon Salmo Salar | 82007 | 8.0 | 0.86 | 13.5 |
| Atlantic Cod Gadus Morhua | 34069 | 10.1 | 1.17 | 17.0 |
| Blue Catfish Ictalurus Furcatus | 20727 | 8.7 | 2.06 | 13.7 |
| Japanese Pufferfish Takifugu Rubripes | 2313 | 6.5 | 0.19 | 12.2 |

TABLE 5-continued

| Species | # of Genbank mRNA/EST sequences with ORF >= 300, 3UTR >= 200, & uniq35start | % column1 mRNA/EST sequences that are dual | % ORFs from column1 sequences that are in (loosely filtered) operons | % ORFs from column1 overlapping with same read direction: |
|---|---|---|---|---|
| Carp *Cyprinus Carpio* | 8275 | 12.4 | 1.50 | 14.6 |
| European Bass *Dicentrarchus Labrax* | 8372 | 9.8 | 0.97 | 13.1 |
| Antarctic Toothfish *Dissostichus mawsoni* | 4151 | 7.1 | 0.40 | 14.2 |
| Atlantic Halibut *H. Hippoglossus* | 4579 | 10.9 | 0.51 | 14.7 |
| Rainbow Smelt *Osmerus Mordax* | 12409 | 14.3 | 2.03 | 17.9 |
| Gilt-head Bream *Sparus Aurata* | 13830 | 9.8 | 1.15 | 12.7 |
| Zebrafish *Danio Rerio* | 37844 | 7.4 | 0.62 | 13.9 |
| Blind Cave Fish *Astyanax Mexicanus* | 37,695 | 7.2 | 0.23 | 12.8 |

Perhaps the most concerning 3'UTR acquisition validation statistic in Table 5 is the percentage of ORFs recognized as being part of an operon. As disclosed, there is no direct handling on operon structure (if present) with the simple algorithm used. Rather, operon handling is done via the iterative bootstrap process mentioned earlier. In the fish analysis a crude operon recognition was done for any transcript that had multiple ORFs non-overlapping, where those ORFs would all be considered part of a single operon, for which a single 3'UTR region is indicated (to the right of the rightmost ORF in the operon). An operon is a cluster of coding regions under common cis-regulation, where the ORFs enclosing those coding regions may overlap to a small extent, such that the operon construction algorithm based on sets of disjoint ORFs (with results shown in Table 6 below) only captures part of the operon structure (providing an estimate). In practice, tuning on allowed overlap amounts reveals an upper bound on percentage of operon structure that is roughly twice that shown in Table 5, for most species, but less than 3% for all. Since the upper bound on operon structure is 3% of the filtered data obtained thus far, this means that we have at most a 3% source of count errors in the 3'UTR 7mer motif analysis. This level of error can be tolerated with the motif-type signal analysis that follows, given the cutoffs that are employed, so further efforts to deal with the operons will be left to when it is necessary.

TABLE 6

| | 7mer_counts | | | | | | | |
|---|---|---|---|---|---|---|---|---|
| Species | μ | σ | σ/μ | #>μ+3σ | #>μ+1σ | % '>μ+1σ' with no4 | 7A-mer counts | #7A/μ |
| Bluefin Tuna *Thunnus thynnus* | 30.6 | 22.87 | 0.745 | 177 | 2005 | 42.3 | 920 | 30 |
| Atlantic Salmon *Salmo Salar* | 1820 | 1280 | 0.703 | 172 | 2211 | 45.7 | 28940 | 16 |
| Atlantic Cod *Gadus Morhua* | 794 | 919 | 1.157 | 70 | 767 | 15.0 | 88430 | 111 |
| Blue Catfish *Ictalurus Furcatus* | 478 | 442 | 0.925 | 107 | 1348 | 32.3 | 30647 | 64 |
| Japanese Pufferfish *Takifugu Rubripes* | 43 | 38 | 0.883 | 247 | 1673 | 55.9 | 1796 | 42 |
| Carp *Cyprinus Carpio* | 202 | 170 | 0.842 | 114 | 1684 | 40.6 | 12078 | 60 |
| European Bass *Dicentrarchus Labrax* | 190 | 152 | 0.800 | 143 | 2047 | 44.9 | 6152 | 32 |
| Antarctic Toothfish *Dissostichus mawsoni* | 86.5 | 87.7 | 1.014 | 118 | 1497 | 38.3 | 6830 | 79 |
| Atlantic Halibut *H. Hippoglossus* | 104.1 | 72.8 | 0.699 | 233 | 2320 | 58.6 | 913 | 9 |
| Rainbow Smelt *Osmerus Mordax* | 348.6 | 234.0 | 0.671 | 191 | 2238 | 47.1 | 3554 | 10 |
| Gilt-head Bream *Sparus Aurata* | 329.6 | 308.3 | 0.935 | 107 | 1628 | 42.1 | 22283 | 68 |
| Zebrafish *Danio Rerio* | 816 | 1249 | 1.531 | 61 | 652 | 28.4 | 133791 | 164 |
| Blind Cave Fish *Astyanax Mexicanus* | 753.0 | 680.5 | 0.904 | 185 | 1778 | 44.3 | 26716 | 35 |

At this point, a set of transcriptome-wide 3'UTR extracts for several species of fish that is highly vetted has been obtained. These sets of 3'UTR regions for their 7mer count statistics can now be examined at a meta-statistical level (see Table 6), without reference to specific sequence information, and then at a direct statistical level as relates to particular signaling motifs that have been identified. Table 6 shows the transcriptome-wide 3'UTR 7mer count statistics, including the mean count and standard deviation on counts, etc., for each species.

If σ/µ<1.0 more of a Gaussian structure is emerging for k-mer count distributions, with easily identifiable "heavy-tail" statistical anomalies, while σ/µ>1.0 indicates a more uniform distribution. The σ/µ>1.0 of the Cod 7mer distribution is partly an artifact of the high poly-A 7mer counts distorting the count statistics, however, as other species transcriptome data with σ/µ>1.0 also had high #7 A/u. So σ/µ>1.0 is not a distinguishing characteristic. If the types of motifs are further examined, however, the high-count 7mers are found to typically fall into two categories: 4 or more bases the same, or no more than 3 bases the same ("no4"). If the percentage of high-count anomalous 7mer with no more than 3 bases of the same type is considered, Atlantic Cod is singled out. If the list of high-count sequences is further looked into, there is a group of 4-or-mor-bases-the-same motifs missing as well, many of them variants of the CstF motif. Thus Atlantic Cod has a notably reduced TF binding site strength for CstF and is lacking a large number of "no4" 7mer miRNA targets. The main result is seen here in the statistics. In these results a trans-regulation diversity biomarker (that is meta-statistics based) is sought and the no4 statistic appears to suffice in this role by singling out Atlantic cod where fishery collapse has occurred from numerous other species not suffering from such as drastic niche failure.

In summary, first recall the typical eukaryotic 3'UTR signaling (starting with the stop codon at the left):

---|TAA-------(T-rich)-----(*)-----AATAAA-----(poly-A site)----(T/GT rich)----

So, it is expected to see in the list of most frequent 7mers in the 3'UTR:

(1) 7mers that are T-rich: ttttttt, ttatttt, tttattt, etc.
(2) 7mers that are A-rich and poly-A with very high counts,
(3) 7mers that have 'AATAAA'
(4) 7mers that are GT-rich for alt-polyA via (*)=(GT rich) signal All of which is seen. Note how all of the 3'UTR signaling related to mRNA production processing have multi-target repeat type signals.

Atlantic Cod, however, is found to have significantly less 'diffuse GT' motif than other species of fish (not shown), the motif involved in CstF recruitment and related poly-A cleavage site selection: e.g., g(tg)(tg)(tg) motifs are seen in cod, but not c(tg)c(tg) or c(tg)tc(tg). Damaged CstF activity is associated with disease and enhanced (detrimental) sensitivity to environmental stimulus—yeast cells with reduced levels of CstF display an enhanced sensitivity to UV treatment, for example.

Discussion

7mers with high frequencies is expected when associated with miRNA binding sites. It is known that many miRNA 7mer binding sites are controlled with high-specificity (i.e., the 7mer-target has no repeating elements that would allow multiple targeting miRNAs), while other miRNA targeting is meant for multiple binding sites (with 7mer binding sites with repeats). High-specificity miRNA signaling can be 'lock' onto by focusing on 7mers with low motif-pattern repetition—this is accomplished by focusing on 7mers that have no more than three bases of the same type (the 'no4' 7mers). The notably less informed (Shannon entropy greater) 7mer count distribution for Cod is hypothesized to relate to a reduced complexity in 7mer-based miRNA/RNAi regulatory capabilities.

If Cod has less trans-regulatory capabilities, resulting in a less diverse selection of phenotypes needed in order to robustly respond to environmental change, then it will become endangered as a species from much more minor environmental changes, as appears to be the case since the collapse of the Cod fisheries in the Northeast. The loss of trans-regulatory diversity may provide a new indicator of overfishing and environmental strain (due to shift in feeding areas further from spawning areas for example), and may provide an early transcriptome-based indicator of fishing stock damage for commercial fisheries.

Atlantic Cod appears to have significantly less 'diffuse GT' motif in its 3'UTR transcripts, indicative of compromised CstF recruitment. Damaged CstF activity is associated with disease and enhanced (detrimental) sensitivity to environmental stimulus—enhanced sensitivity to UV for example. Atlantic Cod also appears to have significantly less trans-regulatory high-specificity ('no4') miRNA complexity than other fish. Less trans-regulatory complexity will lead to less diverse mRNA trans-regulation control of phenotypes, leading to less robust response to environmental change. These results identify a meta-statistical transcriptome-based stock assessment biomarker for potential or occurring ecotype collapse. The biomarker correctly identifies Atlantic Cod as a species at risk from a set including twelve other fish species not thought to be at risk.

Analysis of Axolotl Blastema Regeneration

The following is a description of an investigation into transcriptome switches, and associated phenotype expression ability, of axolotl. This is done by first analyzing the complexity of miRNA/RNAi 7mer-based regulatory motif footprints in the 3' untranslated region (3'UTR) of protein coding transcripts for blastemal and non-blastema cells. The transcriptome/EST data analysis is done using on ORF-finder program written in Perl. EST 3'UTRs are identified, wherein anomalously recurring 7-base sequences, known as "7mers," are sought.

Figure 62:
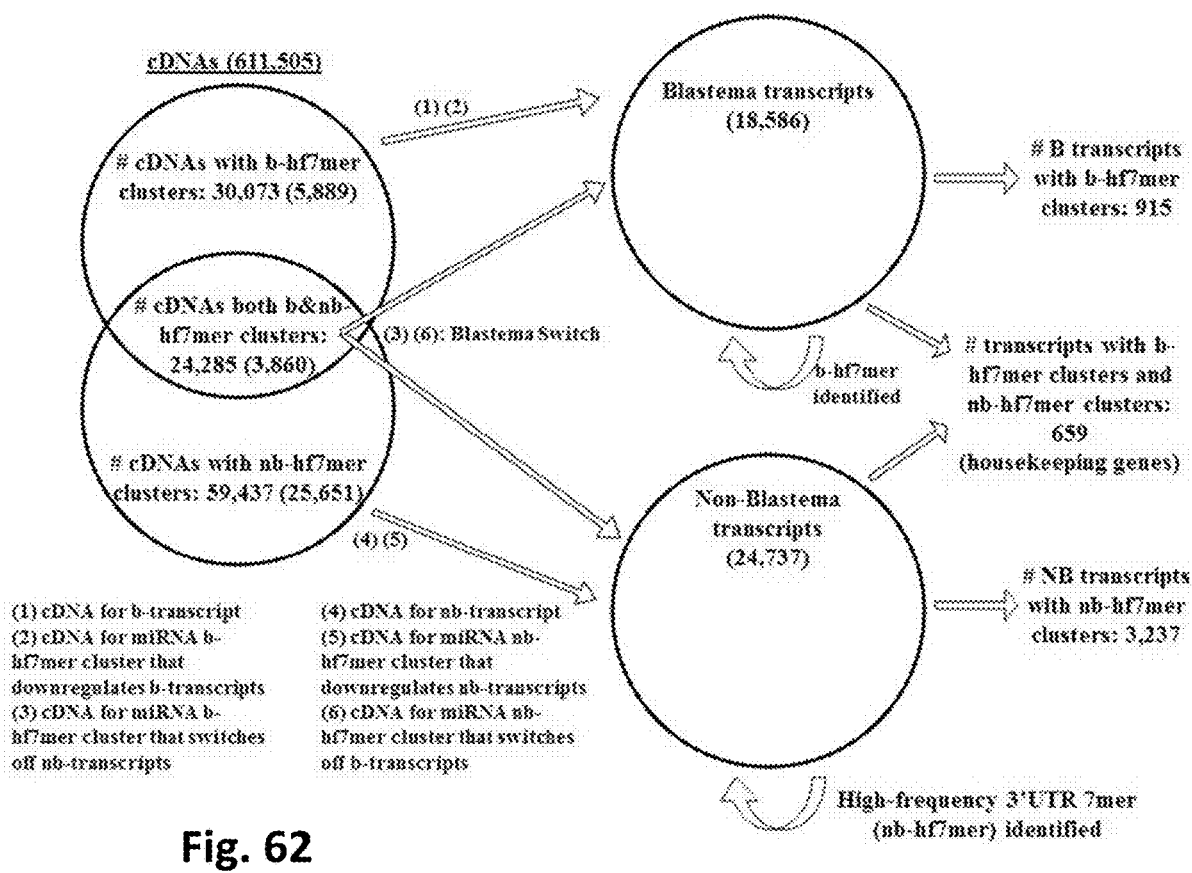
FIG. 62 illustrates a map of high-frequency 7mer clusters.
Figure 63:
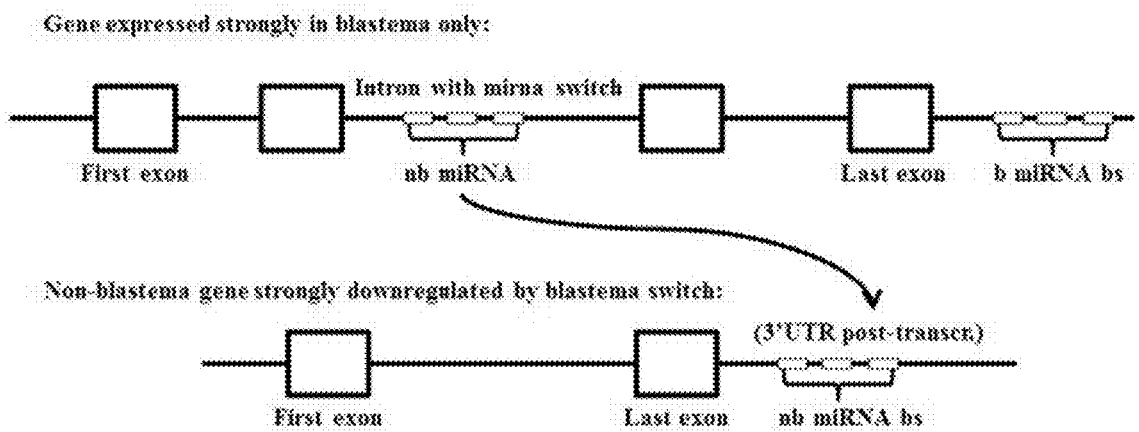
FIG. 63 illustrates a blastema switch.

The 7mer miRNA 3'UTR binding-sites are found to come in clusters and different clusters dominate for the blastema and non-blastema cells. FIG. 62 illustrates a map of high-frequency 7mer clusters, including analysis performed with 18,586 blastema transcripts, 24,737 non-blastema transcripts, and 611,505 cDNA transcripts. The blastema high-frequency 3'UTR 7mers (b-hf7mers) are identified, then the non-blastema high-frequency 3'UTR 7mers (nb-hf7mers). Occurrences of three or more of the high-frequency motifs, referred to as clusters, are sought on transcripts. Results requiring larger clusters are shown in parenthesis for the cDNA data where there was a large sample size. The miRNA 7mer motifs (identified from 3'UTR) also have clusters strongly split between blastema and non-blastema groups—consistent with (1) a feedback loops for blastema-active cDNA gene containing a cluster of blastema mRNA down-regulation targets (normal); and (2) a bistable switch where blastema-active cDNA gene contains a cluster of non-blastema mRNA down-regulation targets, and vice versa. FIG. 63 illustrates a blastema switch in which a blastema transcript encodes a cluster of high-frequency miRNA 7mer binding site seeds for non-blastema transcript. Vice versa for non-blastema cell's being "on". Establishing a biomolecular switch as seen in protein-based transcription factors involved in viral latency in FIG. 63. The added complexity might explain why axolotl genes have introns five times larger than normal—the bistable switch requires the added switch info to reside in the gene, and an overlap with encoding regions to have a miRNA is complex enough to do once, but to get multiple times as needed for the clusters of 7mers seen it is likely its adoption is via haplotype cluster adoption/growth in the intronic regions. FIG. 64 illustrates results of high-frequency motif UC Painter on EST and noisy genomic cDNA data. Highly noisy cDNA genomic data as shown in FIG. 64 is accessible to the 7mer analysis method due to its motif sub-sampling robustness for identifying anomalous statistical events, allowing for preliminary analyses.

Cannabinoid Profiling

As disclosed embodiments use NTD to profile cannabinoids. Embodiments include first the generation/selection of a reporter molecule that will mix into a sample and bind to its designated target, and then be drawn out due to its significantly negative charge. In a similar manner, the DNA in an obviously contaminated blood drop on the floor is all that is needed to identify the owner of the blood drop—their DNA can be extracted from the mix of crud. The negative charge of the *Cannabis* nucleic acid based reporter molecules can easily be enhanced for greater negativity as needed.

Second, consider a cannabinoid X1 that has two features, (A,B), that have been successfully targeted via aptamers or monoclonal antibodies. Consider a second cannabinoid X2 that has features (A,C,D) each, separately, also targeted by its own monoclonal antibody or aptamer. Embodiments can perform an experiment of unknown sample of X1 and X2 where reporter molecules can be tested on the A, B, C, and D, target features. The biosensing on the different molecular features which of the two is present can then be determined. Upon calibration, the relative abundances of both X1 and X2 present if they are presented as a mixture can then be determined. This then extends to other cannabinoids or molecules of inters with binding sites E, F, G, etc.

Third, embodiments afford a reasonable amount of multiplexing to resolve mixtures of reporter molecules. Examples have been shown on 5 molecular species of probes, so 10 reporter species resolution can be accomplished. If there are hundreds of cannabinoids and terpenes and terpenoids, an issue is how to resolve all of this when the universal problem is that a mixture of them is present and there is a need to know that mixture. If a separate reporter molecule was needed for each cannabinoid, and other molecule of interest, then approximately 1000 reporter molecules would be needed in a mixture to fully multiplex detect on an arbitrary mixture populations, which would be difficult. Therefore, embodiments use the feature based detection disclosed above, where the 1000 or so molecules to detect (denoted X1 to X1000 to be consistent with the above) would share amongst themselves the binding sites A, B, C . . . , up to a 10th binding site, therefore requiring only 10 reporter molecules instead of 1000. This can be done with embodiments of the NTD or Nanoscope, which allows a universal assay to be done cheaply and quickly.

Fourth, recall molecule X1 with two successfully targeted binding sites A and B. This molecule can be denoted X1(A,B). Similarly there is X2(A,C,D) from the above. Now introduce a dual-aptamer (one that binds two, different, targets), or a chimeric antibody that is similarly dual. A dual reporter molecule with binding sites (A,B) will allow for agglomeration when binding to X1(A,B) in the manner in which it can chain together with other X1(A,B):

X1(A,B)—binds via B to—reporter(A,B)—binds via A to—X1(A,B)—repeating n times more . . . .

This agglomeration effect will manifest in a number of ways on the Nanoscope, including via observation of reporter sequestration effects alone, so will allow the presence of X1(A,B) when X2(A,C,D) is also present, to be easily discerned, where the mono-aptamer detection on A alone would not be discriminating. With a collection of 10 or so mono-aptamers, and a few dual aptamers, a manageable, scalable, multiplexing detection can be done on the NTD platform disclosed herein.

Several embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:

1. A method for profiling cannabinoids using a nanopore detector, the method comprising:
   using an applied potential to electrophoretically draw a nanopore blockade reporter molecule into a nanopore channel to establish an electrophoretic molecular channel-capture for the reporter molecule;
   wherein the reporter molecule comprises one of an aptamer or a monoclonal antibody and has a specific binding to at least one of: a specific cannabinoid, a particular cannabinoid isoform; or a specific cannabinoid family;
   receiving a blockade channel current signal in response to a nanoscale membrane channel of the nanopore detector being partially blockaded by a presence of the reporter molecule non-covalently bonded to the membrane channel;
   receiving a blockade signal for the reporter molecule that is toggling between more than one level;
   using applied potential polarity-reversals to eject reporter blockades with channel blockade analysis to generate at least one of an open-channel reset process or a solution sampling process;
   using the applied potential to establish a reporter capture state with an electrophoretic restoring force that is tuned to obtain blockade states having stationary statistics over observation periods;
   using the nanopore blockade reporter molecule to transduce molecular state and track molecular state;
   transducing binding and conformational states of the reporter molecule into electrical signals;
   classifying the electrically signals automatically by use of a stochastic carrier wave signal method for identifying information in sequential data that has phases of stationary signal;
   exposing the channel to a test solution during ionic current flow while extracting from the blockaded channel current signal a set of at least one pattern feature to establish over a period of time at least one of a blockaded channel current signal pattern and a change in the blockaded channel current signal pattern;
   having a test condition comprising an introduction of test molecules to a conductive medium and having at least one test molecule specifically bound by the reporter molecule, and upon specific binding of at least one test molecule to the reporter molecule a toggling signal is altered from one pattern to another pattern, having at least one of different rates of toggle between blockade levels and different blockade levels; and
   using the blockade signals to analyze at least one of the reporter molecule, the test molecule, or the molecular complex comprising the test molecule bound to a reporter molecule;
   wherein the reporter molecule comprises a modulatory function separated from a sensing-moiety function by use of at least one of the following: a covalent linker between molecular functionalities; a nucleic-acid annealing based linker between these molecular functionalities; or a nucleic-acid annealing based complex that provides these molecular functionalities upon annealing; and the reporter molecule is a DNA hairpin modulator that is covalently linked to an aptamer-based sensing moiety.

2. The method of claim 1, further comprising:
   comparing the blockade channel current signal pattern to the blockade channel current signal pattern associated with at least one known condition and correlate the blockade channel current signal pattern with at least one known test condition.

3. The method of claim 2 wherein the known condition comprises the presence of a known molecule.

4. The method of claim 3 further comprising correlating the blockade channel current signal pattern with a characteristic of interaction between the test molecule and the reporter molecule.

5. The method of claim 1, further comprising using at least one of chaotropes, viscosity agents, or injected laser modulations from a low-power laser beam directed at the channel with a beam chopper at a tunable frequency.

6. The method of claim 5 wherein the viscosity agents comprise polyethylene glycol (PEG).

7. The method of claim 5 wherein the laser modulations comprise a laser-tweezer tugging on a magnetic bead attached to the reporter molecule.

8. The method of claim 7 wherein the magnetic bead is attached to the reporter molecule using a streptavidin-coated magnetic bead and a biotinylated variant of the reporter molecule that together provides a streptavidin-biotin linkage between modulator and binding functions.

9. The method of claim 1 further comprising using at LNA/DNA chimeras to generate at least one of: longer transducer lifetime; choice of twist mode event transmission with the most discernible modulatory states; or choice of modulator states with the most discernibly different modulations with stationary signal statistics over long time periods.

10. The method of claim 1, wherein a collection of reporter molecules with specific binding to different molecules is used to perform multiplex analysis of a molecular profile by differentiating the reporter molecules according to their different channel modulation signals.

11. The method of claim 1, wherein a collection of reporter molecules with specific binding to different cannabinoids is used to perform multiplex analysis of the cannabinoid profile by differentiating the reporter molecules according to their different channel modulation signals.

12. The method of claim 1, the classifying the electrically signals comprising:
   identifying signal regions in stochastic sequential data using at least one of Hidden Markov model (HMM)-based methods or Finite State Automata (FSA)-based methods, and using the signal region identification in later stages of signal processing to focus more intense computational efforts on only the regions indicated;

identifying sub-states and features in the signal regions using at least one of an FSA; an HMM; an HMM with Emission Variance Amplification (EVA) filtering; an HMM with Duration (HMMD);

using identified signal sub-states and features to define a feature vector with a fixed number of parameters regardless of the duration and type of signal region examined so as to provide a standard feature vector extraction for use by Support Vector Machine (SVM) processing;

extracting feature vectors from the identified signal regions using at least one of an FSA, an HMM, a generalized clique HMM (meta-HMM), a gap-interpolated Markov model, a hash-interpolated Markov model, and an HMM-with-binned-duration model (HMMBD);

using generalized SVM-based methods for signal learning in at least one of three contexts: (1) classifying the extracted feature vectors using labeled training data; (2) clustering the extracted features in instances where there is no labeled training data to reference, using external SVM-based clustering methods; and (3) classifying some of the extracted features in instances where there is incomplete label information on the signal classes, using SVM-based projection-classification methods;

using the trained (from signal learning) generalized SVM-based method to accomplish at least one of two learning tasks: signal region classification and signal region clustering, to thereby establish known channel current signal patterns.

13. A method for profiling cannabinoids using a nanopore detector, the method comprising:

using an applied potential to electrophoretically draw a nanopore blockade reporter molecule into a nanopore channel to establish an electrophoretic molecular channel-capture for the reporter molecule;

wherein the reporter molecule comprises one of an aptamer or a monoclonal antibody and has a specific binding to at least one of: a specific cannabinoid, a particular cannabinoid isoform; or a specific cannabinoid family;

receiving a blockade channel current signal in response to a nanoscale membrane channel of the nanopore detector being partially blockaded by a presence of the reporter molecule non-covalently bonded to the membrane channel;

receiving a blockade signal for the reporter molecule that is toggling between more than one level;

using applied potential polarity-reversals to eject reporter blockades with channel blockade analysis to generate at least one of an open-channel reset process or a solution sampling process;

using the applied potential to establish a reporter capture state with an electrophoretic restoring force that is tuned to obtain blockade states having stationary statistics over observation periods;

using the nanopore blockade reporter molecule to transduce molecular state and track molecular state;

transducing binding and conformational states of the reporter molecule into electrical signals;

classifying the electrically signals automatically by use of a stochastic carrier wave signal method for identifying information in sequential data that has phases of stationary signal;

exposing the channel to a test solution during ionic current flow while extracting from the blockaded channel current signal a set of at least one pattern feature to establish over a period of time at least one of a blockaded channel current signal pattern and a change in the blockaded channel current signal pattern;

having a test condition comprising an introduction of test molecules to a conductive medium and having at least one test molecule specifically bound by the reporter molecule, and upon specific binding of at least one test molecule to the reporter molecule a toggling signal is altered from one pattern to another pattern, having at least one of different rates of toggle between blockade levels and different blockade levels;

using the blockade signals to analyze at least one of the reporter molecule, the test molecule, or the molecular complex comprising the test molecule bound to a reporter molecule; and using LNA/DNA chimeras to generate at least one of: longer transducer lifetime; choice of twist mode event transmission with the most discernible modulatory states; or choice of modulator states with the most discernibly different modulations with stationary signal statistics over long time periods.

14. The method of claim 13, further comprising:

comparing the blockade channel current signal pattern to the blockade channel current signal pattern associated with at least one known condition and correlate the blockade channel current signal pattern with at least one known test condition.

15. The method of claim 14 wherein the known condition comprises the presence of a known molecule, further comprising correlating the blockade channel current signal pattern with a characteristic of interaction between the test molecule and the reporter molecule.

16. The method of claim 13, further comprising using at least one of chaotropes, viscosity agents, or injected laser modulations from a low-power laser beam directed at the channel with a beam chopper at a tunable frequency.

17. The method of claim 13, wherein a collection of reporter molecules with specific binding to different cannabinoids is used to perform multiplex analysis of the cannabinoid profile by differentiating the reporter molecules according to their different channel modulation signals.

18. The method of claim 13, the classifying the electrically signals comprising:

identifying signal regions in stochastic sequential data using at least one of Hidden Markov model (HMM)-based methods or Finite State Automata (FSA)-based methods, and using the signal region identification in later stages of signal processing to focus more intense computational efforts on only the regions indicated;

identifying sub-states and features in the signal regions using at least one of an FSA; an HMM; an HMM with Emission Variance Amplification (EVA) filtering; an HMM with Duration (HMMD);

using identified signal sub-states and features to define a feature vector with a fixed number of parameters regardless of the duration and type of signal region examined so as to provide a standard feature vector extraction for use by Support Vector Machine (SVM) processing;

extracting feature vectors from the identified signal regions using at least one of an FSA, an HMM, a generalized clique HMM (meta-HMM), a gap-interpolated Markov model, a hash-interpolated Markov model, and an HMM-with-binned-duration model (HMMBD);

using generalized SVM-based methods for signal learning in at least one of three contexts: (1) classifying the extracted feature vectors using labeled training data; (2) clustering the extracted features in instances where there is no labeled training data to reference, using external SVM-based clustering methods; and (3) classifying some of the extracted features in instances where there is incomplete label information on the signal classes, using SVM-based projection-classification methods;

using the trained (from signal learning) generalized SVM-based method to accomplish at least one of two learning tasks: signal region classification and signal region clustering, to thereby establish known channel current signal patterns.

* * * * *

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caagcttggt ttcgataggt a                                              21

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 2
atcgtttcca agcttg                                                      16

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gttcgaacgt tttcgttcga ac                                               22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtcgaacgtt ttcgttcgac                                                  20

<210> SEQ ID NO 5
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctccgtcgac gagtttatag acttttgtct ataaactcgc agtcatgctt ttgcatgact      60
gcgtcgacgg ag                                                          72

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
gtcgaacgtt tttcgttcga c                                                21

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
gttcgaacgt ttttcgttcg aac                                              23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 8
gcttgaacgt tttcgttcaa gc                                                22

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gttcgaacgg gtgagggcgc ttttgcgccc tcacccgttc gaac                         44

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gttcgaacgg gtgagggcgc tttttgcgcc ctcacccgtt cgaac                        45

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gttgaacgtt ttcgttcaac                                                   20

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctccgaacct tgttatcca tatggataac tttggttcgg ag                           42

<210> SEQ ID NO 13
<211> LENGTH: 846
<212> TYPE: DNA
<213> ORGANISM: Ambystoma mexicanum

<400> SEQUENCE: 13
ggcctcctca gactttgaaa ttgtgccagc agatgagagt gaaaggaggg agaaagggtg        60
ctcgcctggc agtgggaaat tggacctgga gccccctcaa tacccgaaga atgctgacag       120
cgctctgctc cttcagctgc agcgcctgga gagctcactc agtgattttg cagaggaacc       180
agaccggaac cagctcttca cacaccttgg gcgaatggcc ctggagttca accggctggc       240
agccaaagtg cacaagaacg agcagaagac ctctgttctg cagaccctct gtgagcagct       300
gcgcaaggag aacgaggatc tgaggaagaa ccttgagaag gatctggagc agagaagtca       360
tgacactgag aacctaaggg tggagaacat ggagctgaag cgcaaggtca cccttgctgg       420
aaaagatatc cttaggaaag tggatatgga tttgaacggt gaatgtccag gaagtggtga       480

```
tggaatggcg ctggaacgta tacagctgca gcagactggc aagttggcag agaatgtgac        540
ggtgaaagat gttctggggg taacggagaa gaaagtaaag gccttggagc atcagaggaa        600
tgagttgctg gaggtgaata agcagtggga caaacatttc cgctccatga agcagcaata        660
cgaacagaag ataacctcac tgcgccagaa gctgtctgac tcccagaaac ttgtcactga        720
cttggaagca gagcgggaac agaaacagag ggactttgaa cgcaagctgc ttcttgccaa        780
gtccaaaatt gagactgaag agggtgagaa gaaagtgctg gaagttgaag tgcaggaact        840
tattca                                                                     846

<210> SEQ ID NO 14
<211> LENGTH: 498
<212> TYPE: DNA
<213> ORGANISM: Ambystoma mexicanum
<220> FEATURE:
<221> NAME/KEY: modified_base
<222> LOCATION: (101)..(232)
<223> OTHER INFORMATION: a, c, t, g, unknown or other
<220> FEATURE:
<221> NAME/KEY: modified_base
<222> LOCATION: (301)..(464)
<223> OTHER INFORMATION: a, c, t, g, unknown or other

<400> SEQUENCE: 14
gggcttggat gcatgggtaa aaaacatccc acaagccccc cgtcttgtga tggccattct         60
tatcttttac tgatggcact cacaagatct gggatgttcg nnnnnnnnnn nnnnnnnnnn        120
nnnnnnnnnn nnnnnnnnnn nnnnnnnnnn nnnnnnnnnn nnnnnnnnnn nnnnnnnnnn        180
nnnnnnnnnn nnnnnnnnnn nnnnnnnnnn nnnnnnnnnn nnnnnnnnnn nnccttcttc        240
cgattccgca gttgacaaag ttcagcaact tttccttcat cagggtggat cgatcggttc        300
nnnnnnnnnn nnnnnnnnnn nnnnnnnnnn nnnnnnnnnn nnnnnnnnnn nnnnnnnnnn        360
nnnnnnnnnn nnnnnnnnnn nnnnnnnnnn nnnnnnnnnn nnnnnnnnnn nnnnnnnnnn        420
nnnnnnnnnn nnnnnnnnnn nnnnnnnnnn nnnnnnnnnn nnnnttcgtc ttccgtggtc        480
agtctccagg ttttctttt                                                      498

<210> SEQ ID NO 15
<211> LENGTH: 307
<212> TYPE: DNA
<213> ORGANISM: Ambystoma mexicanum
<220> FEATURE:
<221> NAME/KEY: modified_base
<222> LOCATION: (101)..(260)
<223> OTHER INFORMATION: a, c, t, g, unknown or other

<400> SEQUENCE: 15
tgaccatcat atttgccaaa ggagagaggc atatgggcta aatcgcctct ttcttcattc         60
cgtactgcag cctgctgctt aagtacggca ttttccgctt nnnnnnnnnn nnnnnnnnnn        120
nnnnnnnnnn nnnnnnnnnn nnnnnnnnnn nnnnnnnnnn nnnnnnnnnn nnnnnnnnnn        180
nnnnnnnnnn nnnnnnnnnn nnnnnnnnnn nnnnnnnnnn nnnnnnnnnn nnnnnnnnnn        240
nnnnnnnnnn nnnnnnnnnn tattctgtca cgcctagaca atcccgggga aatctcctat        300
gaccccc                                                                   307

<210> SEQ ID NO 16
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      probe

<400> SEQUENCE: 16
gtcgaacgtt tttcgttcga c                                              21
```